United States Patent
Bayyouk et al.

(10) Patent No.: US 10,436,766 B1
(45) Date of Patent: Oct. 8, 2019

(54) MONITORING LUBRICANT IN HYDRAULIC FRACTURING PUMP SYSTEM

(71) Applicant: S.P.M. Flow Control, Inc., Fort Worth, TX (US)

(72) Inventors: Jacob A. Bayyouk, Richardson, TX (US); Trever Stewart, Fort Worth, TX (US)

(73) Assignee: S.P.M. Flow Control, Inc., Fort Worth, TX (US)

( * ) Notice: Subject to any disclaimer, the term of this patent is extended or adjusted under 35 U.S.C. 154(b) by 324 days.

(21) Appl. No.: 15/289,462

(22) Filed: Oct. 10, 2016

Related U.S. Application Data

(60) Provisional application No. 62/240,224, filed on Oct. 12, 2015.

(51) Int. Cl.
  *G01N 33/30* (2006.01)
  *G01N 33/28* (2006.01)
  (Continued)

(52) U.S. Cl.
  CPC ......... *G01N 33/2888* (2013.01); *E21B 43/26* (2013.01); *E21B 47/00* (2013.01);
  (Continued)

(58) Field of Classification Search
  CPC ............................ G01N 33/2888; F04B 53/18
  See application file for complete search history.

(56) References Cited

U.S. PATENT DOCUMENTS

| 364,627 A | 6/1887 | Arnold |
| 879,560 A | 2/1908 | Lepley |

(Continued)

FOREIGN PATENT DOCUMENTS

| BR | 8700642 A | 8/1988 |
| CA | 2686204 A1 | 5/2010 |

(Continued)

OTHER PUBLICATIONS

"Advisory Action dated Apr. 7, 2009, by the USPTO, re U.S. Appl. No. 10/833,921".

(Continued)

*Primary Examiner* — Hongmin Fan
(74) *Attorney, Agent, or Firm* — Foley & Lardner LLP

(57) ABSTRACT

A monitoring apparatus is adapted to monitor lubricant in a hydraulic fracturing pump system, and includes a gateway and one or more sensors configured to be in communication with the gateway. The one or more sensors are configured to measure quality of the lubricant, a pressure of the lubricant, and a temperature of the lubricant. The gateway is configured to receive sensor data associated with the quality of the lubricant, the pressure of the lubricant, and the temperature of the lubricant. To monitor the lubricant, the gateway is configured to: store the sensor data on the non-transitory computer readable medium; transmit to another computing device the sensor data and/or representative data based on the sensor data; visually indicate a status of the quality of the lubricant; visually indicate a status of the pressure of the lubricant; visually indicate a status of the temperature of the lubricant; or any combination thereof.

20 Claims, 24 Drawing Sheets

(51) Int. Cl.
*E21B 43/26* (2006.01)
*E21B 47/00* (2012.01)
*F04B 17/05* (2006.01)
*F04B 47/02* (2006.01)
*F04B 53/18* (2006.01)
*F04B 51/00* (2006.01)

(52) U.S. Cl.
CPC .............. *F04B 17/05* (2013.01); *F04B 47/02* (2013.01); *F04B 51/00* (2013.01); *F04B 53/18* (2013.01)

(56) References Cited

U.S. PATENT DOCUMENTS

| | | | |
|---|---|---|---|
| 1,418,202 A | 5/1922 | Parsons | |
| 1,707,228 A | 4/1929 | Knapp | |
| 1,867,585 A | 7/1932 | Moore | |
| 1,890,428 A | 12/1932 | Ferris et al. | |
| 1,926,925 A | 9/1933 | Wescott | |
| 2,056,622 A | 10/1936 | Schaer | |
| 2,420,779 A | 5/1947 | Holmes | |
| 2,428,602 A | 10/1947 | Yingling | |
| 2,443,332 A | 6/1948 | Summers | |
| 2,665,555 A | 1/1954 | Martinsson | |
| 2,682,433 A | 6/1954 | Maier | |
| 2,755,739 A | 7/1956 | Euwe | |
| 2,766,701 A | 10/1956 | Giraudeau | |
| 2,823,085 A | 2/1958 | Keylwert | |
| 2,828,931 A | 4/1958 | Harvey | |
| 2,878,990 A | 3/1959 | Zurcher | |
| 2,991,003 A | 7/1961 | Petersen | |
| 3,039,317 A | 6/1962 | Wilson | |
| 3,049,082 A | 8/1962 | Barry | |
| 3,137,179 A | 6/1964 | Moorhead | |
| 3,158,211 A | 11/1964 | McCue et al. | |
| 3,163,474 A | 12/1964 | Wilson | |
| 3,168,665 A | 2/1965 | Holper | |
| 3,179,451 A | 4/1965 | Blank, Sr. | |
| 3,206,242 A | 9/1965 | Fensin | |
| 3,207,142 A | 9/1965 | Gorissen et al. | |
| 3,236,315 A | 2/1966 | Lora | |
| 3,356,036 A | 12/1967 | Repp | |
| 3,358,352 A | 12/1967 | Wilcox | |
| 3,487,892 A | 1/1970 | Kiefer | |
| 3,595,101 A | 7/1971 | Cooper, Jr. | |
| 3,757,149 A | 9/1973 | Holper | |
| 3,760,694 A | 9/1973 | Lieb | |
| 3,883,941 A | 5/1975 | Coil | |
| 3,967,542 A | 7/1976 | Hall et al. | |
| 4,013,057 A | 3/1977 | Guenther | |
| 4,048,909 A | 9/1977 | Jepsen | |
| 4,099,447 A | 7/1978 | Ogles | |
| 4,140,442 A | 2/1979 | Mulvey | |
| 4,191,238 A | 3/1980 | Pichl | |
| 4,210,399 A | 7/1980 | Jain | |
| 4,211,190 A | 7/1980 | Indech | |
| 4,246,908 A | 1/1981 | Inagaki et al. | |
| 4,269,569 A | 5/1981 | Hoover | |
| 4,338,054 A | 7/1982 | Dahl | |
| 4,381,179 A | 4/1983 | Pareja | |
| 4,388,837 A | 6/1983 | Bender | |
| 4,476,772 A | 10/1984 | Gorman et al. | |
| 4,477,237 A | 10/1984 | Grable | |
| 4,494,415 A | 1/1985 | Elliston | |
| 4,512,694 A | 4/1985 | Foran et al. | |
| 4,553,298 A | 11/1985 | Grable | |
| 4,606,709 A | 8/1986 | Chisolm | |
| 4,667,627 A | 5/1987 | Matsui et al. | |
| 4,705,459 A | 11/1987 | Buisine et al. | |
| 4,729,249 A | 3/1988 | Besic | |
| 4,762,051 A | 8/1988 | Besic et al. | |
| 4,771,801 A | 9/1988 | Crump et al. | |
| 4,803,964 A | 2/1989 | Kurek et al. | |
| 4,809,646 A | 3/1989 | Paul et al. | |
| 4,824,342 A | 4/1989 | Buck | |
| 4,842,039 A | 6/1989 | Kelm | |
| 4,876,947 A | 10/1989 | Rhodes | |
| 4,887,518 A | 12/1989 | Hayakawa | |
| 4,939,984 A | 7/1990 | Fletcher-Jones | |
| 4,950,145 A | 8/1990 | Zanetos et al. | |
| 4,966,109 A | 10/1990 | Pusic et al. | |
| 5,031,512 A | 7/1991 | Graziani | |
| 5,060,603 A | 10/1991 | Williams | |
| 5,063,775 A | 11/1991 | Walker, Sr. et al. | |
| 5,076,220 A | 12/1991 | Evans et al. | |
| 5,078,580 A | 1/1992 | Miller et al. | |
| 5,080,319 A | 1/1992 | Nielsen | |
| 5,115,725 A | 5/1992 | Horiuchi | |
| 5,135,031 A | 8/1992 | Burgess et al. | |
| 5,156,534 A | 10/1992 | Burgy et al. | |
| 5,216,943 A | 6/1993 | Adler et al. | |
| 5,246,355 A | 9/1993 | Matzner et al. | |
| 5,247,873 A | 9/1993 | Owens et al. | |
| 5,287,612 A | 2/1994 | Paddock et al. | |
| 5,313,061 A | 5/1994 | Drew et al. | |
| 5,337,612 A | 8/1994 | Evans | |
| 5,370,093 A | 12/1994 | Hayes | |
| 5,425,306 A | 6/1995 | Binford | |
| 5,560,332 A | 10/1996 | Chang | |
| 5,594,665 A | 1/1997 | Walter et al. | |
| 5,658,250 A | 8/1997 | Blomquist et al. | |
| 5,671,655 A | 9/1997 | Vollrath | |
| 5,673,666 A | 10/1997 | Beardmore et al. | |
| 5,772,403 A | 6/1998 | Allison et al. | |
| 5,839,888 A | 11/1998 | Harrison | |
| 5,846,056 A | 12/1998 | Dhindsa et al. | |
| 5,855,397 A | 1/1999 | Black et al. | |
| 5,984,645 A | 11/1999 | Cummings | |
| 6,260,004 B1 | 7/2001 | Hays et al. | |
| 6,286,363 B1 * | 9/2001 | Discenzo | G01N 11/16 340/631 |
| 6,330,525 B1 | 12/2001 | Hays et al. | |
| 6,419,459 B1 | 7/2002 | Sibbing | |
| 6,557,457 B1 | 5/2003 | Hart et al. | |
| 6,663,349 B1 | 12/2003 | Discenzo et al. | |
| 6,697,741 B2 | 2/2004 | Yu et al. | |
| 6,718,955 B1 | 4/2004 | Knight | |
| D495,342 S | 8/2004 | Tojo et al. | |
| D496,670 S | 9/2004 | Ohnishi | |
| 6,853,110 B1 | 2/2005 | Durham et al. | |
| 6,859,740 B2 | 2/2005 | Stephenson et al. | |
| 6,873,267 B1 | 3/2005 | Tubel et al. | |
| 6,882,960 B2 | 4/2005 | Miller | |
| 7,111,604 B1 | 9/2006 | Hellenbroich et al. | |
| D538,824 S | 3/2007 | Tojo | |
| 7,219,594 B2 | 5/2007 | Kugelev et al. | |
| 7,220,119 B1 | 5/2007 | Kirchmer et al. | |
| 7,272,533 B2 | 9/2007 | Schlosser et al. | |
| 7,364,412 B2 | 4/2008 | Kugelev et al. | |
| 7,374,005 B2 | 5/2008 | Gray et al. | |
| 7,404,704 B2 | 7/2008 | Kugelev et al. | |
| D591,311 S | 4/2009 | Tojo | |
| 7,588,384 B2 | 9/2009 | Yokohara | |
| 7,610,847 B2 | 11/2009 | McKelroy | |
| 7,621,179 B2 | 11/2009 | Ens et al. | |
| 7,623,986 B2 | 11/2009 | Miller et al. | |
| 7,866,153 B2 | 1/2011 | Sollie et al. | |
| 7,931,078 B2 | 4/2011 | Toporowski et al. | |
| 8,100,048 B2 | 1/2012 | Christopher | |
| 8,162,631 B2 | 4/2012 | Patel et al. | |
| D658,684 S | 5/2012 | Roman | |
| D668,266 S | 10/2012 | Ramirez, Jr. | |
| D670,312 S | 11/2012 | Alexander et al. | |
| D676,875 S | 2/2013 | Ramirez, Jr. | |
| 8,376,723 B2 | 2/2013 | Kugelev et al. | |
| D678,628 S | 3/2013 | Krueger | |
| D678,911 S | 3/2013 | Prevost | |
| D682,317 S | 5/2013 | Carruth et al. | |
| D685,393 S | 7/2013 | Prevost | |
| 8,529,230 B1 | 9/2013 | Colley, III et al. | |
| D692,026 S | 10/2013 | Alexander et al. | |
| D693,200 S | 11/2013 | Saunders | |
| D698,502 S | 1/2014 | Krueger | |
| D700,622 S | 3/2014 | Carruth et al. | |

(56) References Cited

U.S. PATENT DOCUMENTS

| | | | |
|---|---|---|---|
| 8,707,853 B1 | 4/2014 | Dille et al. | |
| D704,385 S | 5/2014 | Hoofman | |
| D708,401 S | 7/2014 | Krueger | |
| D713,101 S | 9/2014 | Bruno et al. | |
| 8,833,301 B2 | 9/2014 | Donegan et al. | |
| 8,833,302 B2 | 9/2014 | Donegan et al. | |
| 8,857,374 B1 | 10/2014 | Donegan et al. | |
| D759,728 S | 6/2016 | Byrne et al. | |
| 2001/0013247 A1* | 8/2001 | Wilson | G01N 33/2858 73/54.01 |
| 2002/0020460 A1 | 2/2002 | Viken | |
| 2002/0189587 A1 | 12/2002 | Hirano | |
| 2003/0024386 A1 | 2/2003 | Burke | |
| 2003/0079604 A1 | 5/2003 | Seo | |
| 2003/0118104 A1 | 6/2003 | Zaccarin | |
| 2004/0213677 A1 | 10/2004 | Matzner et al. | |
| 2004/0219040 A1 | 11/2004 | Kugelev et al. | |
| 2004/0244577 A1 | 12/2004 | Haughom | |
| 2006/0029502 A1 | 2/2006 | Kugelev et al. | |
| 2007/0041847 A1 | 2/2007 | Inoue et al. | |
| 2007/0041849 A1 | 2/2007 | Allen | |
| 2007/0099746 A1 | 5/2007 | Hahlbeck | |
| 2007/0144842 A1 | 6/2007 | Zhou | |
| 2008/0006089 A1* | 1/2008 | Adnan | F04B 51/00 73/587 |
| 2008/0006148 A1 | 1/2008 | McKelroy | |
| 2008/0078583 A1 | 4/2008 | Cummins | |
| 2008/0213115 A1 | 9/2008 | Hilger et al. | |
| 2008/0271562 A1 | 11/2008 | Yasuhara et al. | |
| 2009/0084260 A1 | 4/2009 | Christopher | |
| 2009/0092510 A1 | 4/2009 | Williams et al. | |
| 2010/0044028 A1 | 2/2010 | Brooks | |
| 2010/0129245 A1 | 5/2010 | Patel et al. | |
| 2010/0129249 A1 | 5/2010 | Bianchi et al. | |
| 2010/0158726 A1 | 6/2010 | Donald et al. | |
| 2010/0160710 A1 | 6/2010 | Strickland | |
| 2010/0172778 A1 | 7/2010 | Kugelev et al. | |
| 2010/0242720 A1 | 9/2010 | Matzner et al. | |
| 2010/0260631 A1 | 10/2010 | Kugelev et al. | |
| 2010/0310403 A1* | 12/2010 | Szepesy | F01C 21/0809 418/248 |
| 2010/0322802 A1 | 12/2010 | Kugelev | |
| 2012/0084019 A1* | 4/2012 | Khonsari | C22C 38/00 702/35 |
| 2012/0141305 A1 | 6/2012 | Landers et al. | |
| 2012/0144995 A1 | 6/2012 | Bayyouk et al. | |
| 2012/0148430 A1 | 6/2012 | Hubenschmidt et al. | |
| 2012/0167759 A1 | 7/2012 | Chinthan et al. | |
| 2013/0064696 A1 | 3/2013 | McCormick et al. | |
| 2013/0206108 A1 | 8/2013 | Schuele et al. | |
| 2013/0233165 A1 | 9/2013 | Matzner et al. | |
| 2013/0290066 A1* | 10/2013 | Altamirano | G06Q 10/0633 705/7.27 |
| 2014/0196570 A1 | 7/2014 | Small et al. | |
| 2015/0377318 A1 | 12/2015 | Byrne | |
| 2016/0025082 A1 | 1/2016 | Byrne et al. | |
| 2016/0025088 A1 | 1/2016 | Byrne et al. | |
| 2016/0025089 A1 | 1/2016 | Kumar et al. | |
| 2016/0025090 A1 | 1/2016 | Bayyouk et al. | |
| 2016/0335465 A1* | 11/2016 | LeBlanc | H04L 12/2854 |
| 2017/0211569 A1* | 7/2017 | Urdaneta | F04B 49/065 |
| 2017/0363529 A1* | 12/2017 | Ture | G01N 15/0656 |

FOREIGN PATENT DOCUMENTS

| | | |
|---|---|---|
| CA | 2749110 A1 | 7/2010 |
| CA | 2486126 C | 1/2013 |
| CA | 153846 | 9/2014 |
| CN | 2436688 Y | 6/2001 |
| CN | 2612816 Y | 4/2004 |
| CN | 2926584 Y | 7/2007 |
| CN | 201092955 Y | 7/2008 |
| CN | 101476558 A | 7/2009 |
| CN | 102439314 A | 5/2012 |
| CN | 103403351 A | 11/2013 |
| CN | ZL2009100265839 | 4/2014 |
| CN | 105264275 A | 1/2016 |
| DE | 3234504 A1 | 4/1983 |
| DE | 3441508 A1 | 5/1986 |
| DE | 3802714 A1 | 8/1988 |
| DE | 4416120 A1 | 11/1995 |
| EP | 0300905 A1 | 1/1989 |
| FR | 2618509 A1 | 1/1989 |
| GB | 2342421 B | 3/2003 |
| GB | 2419671 A | 5/2006 |
| GB | 2482786 B | 1/2015 |
| JP | 60175753 A | 9/1985 |
| JP | 194453 | 7/1990 |
| JP | 10288086 A | 10/1998 |
| JP | 2920004 B2 | 7/1999 |
| JP | 11200947 A | 7/1999 |
| JP | 3974386 B2 | 9/2007 |
| JP | 2008539364 A | 11/2008 |
| KR | 100275877 B1 | 12/2000 |
| KR | 100287572 | 6/2001 |
| KR | 1020010065249 | 7/2001 |
| KR | 100302886 | 11/2001 |
| KR | 1020010108223 | 12/2001 |
| RU | 2037700 C1 | 6/1995 |
| WO | WO-2008137515 A1 | 11/2008 |
| WO | WO-2010080961 A2 | 7/2010 |
| WO | WO-2010080963 A2 | 7/2010 |
| WO | WO-2011005571 A2 | 1/2011 |
| WO | WO-2012092452 A2 | 7/2012 |
| WO | WO-2014143094 | 9/2014 |
| WO | WO-2016014967 A1 | 1/2016 |
| WO | WO-2016014988 A1 | 1/2016 |
| WO | WO-2016015006 A1 | 1/2016 |
| WO | WO-2016015012 A1 | 1/2016 |
| WO | WO-2015200810 A3 | 2/2016 |

OTHER PUBLICATIONS

"Australia Exam Report, dated Feb. 9, 2015, by IP Australia, re App No. 2011352095".

"Canada Exam Report dated Aug. 18, 2016, by the CPO, re App No. 2905809".

"Canada Exam Report dated Jan. 11, 2016, by the CIPO, re App No. 2749110".

"Canada Exam Report, dated Oct. 22, 2015, by the CIPO, re App No. 2686204".

"Canadian Exam Report, dated Oct. 8, 2014, by CIPO, re App No. 2823213".

"Canadian Examiner's Report, by CIPO, dated May 13, 2014, re App No. 153846".

"Canadian Office Action dated May 17, 2011, re App No. 2486126".

"Chinese Office Action, dated Sep. 2, 2014, by SIPO, re App No. 201080008236.X".

"Chinese Office Action dated Oct. 29, 2013, re App No. 201080008236X".

"Decision on Appeal mailed Feb. 20, 2013, by USPTO, re U.S. Appl. No. 10/831,467".

"Dirk Guth et al., "New Technology for a High Dynamical MRF-Clutch for Safe and Energy-Efficient Use in Powertrain," FISITA 2012 World Automotive Congress, Beijing, China, Nov. 27-30, 2012, 31 pages".

"Election Requirement, dated Nov. 18, 2014, by the USPTO, re U.S. Appl. No. 29/455,618".

*Estee Lauder Inc.* v. *L'Oreal*, USA. 129 F.3d 588, 44 U.S.P.Q.2d 1610, No. 96-1512, United States Court of Appeals, Federal Circuit, Decided Nov. 3, 1997.

"Examiner's Answer mailed Jan. 29, 2010, by USPTO, re U.S. Appl. No. 10/831,467".

"Examiner Interview Summary dated Apr. 10, 2008, by the USPTO, re U.S. Appl. No. 10/833,921".

"Examiner Interview Summary dated Jul. 17, 2008, by the USPTO, re U.S. Appl. No. 10/831,467".

"Gardner Denver Well Servicing Pump Model C-2500Q Power End Parts List, Feb. 2009".

(56) References Cited

OTHER PUBLICATIONS

"Simatec Smart Technologies, "Simatool Bearing Handling Tool BHT", Dec. 19, 2013".
"International Preliminary Report on Patentability, by the IPEA/US, dated Aug. 23, 2016 re PCT/US2015/042043".
"International Preliminary Report on Patentability, by the IPEA/US, dated Mar. 9, 2015, re PCT/US2013/040106".
"International Preliminary Report on Patentability for Application No. PCT/US2015/42104 dated Sep. 16, 2016".
"International Preliminary Report on Patentability dated Jan. 4, 2012, regarding PCT/US2010/039651".
"International Preliminary Report on Patentability dated Jul. 12, 2011, regarding PCT/US2010/020445".
"International Preliminary Report on Patentability dated Jul. 12, 2011, regarding PCT/US2010/020447".
"International Search Report and Written Opinion, by the ISA/US, dated Mar. 4, 2015, re PCT/US2014/069567".
International Search Report and Written Opinion for Application No. PCT/US2010/020445 dated Aug. 3, 2010, 7 pages.
International Search Report and Written Opinion for Application No. PCT/US2010/020447 dated Aug. 3, 2010, 7 pages.
International Search Report and Written Opinion for Application No. PCT/US2010/039651 dated Feb. 24, 2011, 7 pages.
International Search Report and Written Opinion for Application No. PCT/US2011/067770 dated Aug. 28, 2012, 8 pages.
"International Search Report and Written Opinion dated Dec. 28, 2015, by the ISA/US, re PCT/US2015/042043".
"International Search Report and Written Opinion dated Dec. 4, 2015, by the ISA/US, re PCT/US2015/042078".
"International Search Report and Written Opinion dated Dec. 4, 2015, by the ISA/US, re PCT/US2015/042111".
"International Search Report and Written Opinion dated Jun. 29, 2015, by the ISA/US, re PCT/US2015/014898".
"International Search Report and Written Opinion, dated Nov. 27, 2015, by the ISA/US, re PCT/US2015/038008".
"International Search Report and Written Opinion dated Oct. 19, 2015, by the ISA/US, re PCT/US2015/042104".
"International Search Report and Written Opinion, dated Oct. 19, 2015, by the ISA/US, re PCT/US2015/042119".
"International Search Report and Written Opinion dated Sep. 5, 2013, by the ISA/US, re PCT/US2013/040106".
"Metaldyne, Torsional Vibration Dampers, Brochure".
"MSI/Dixie Iron Works, Ltd., Technical Manual for 600 HP Triplex MSI TI-600 Pump, Rev. P, 102 pages, date unknown".
"MSI/Dixie Iron Works, Ltd., Technical Manual for MSI Hybrid Well Service Pump Triplex and Quintuplex Models, Rev. D, 91 pages, date unknown".
"Notice of Allowance dated Dec. 23, 2011, by the USPTO, re U.S. Appl. No. 12/277,849".
"Notice of Allowance dated Feb. 12, 2016, by the USPTO, re U.S. Appl. No. 29/534,091".
"Notice of Allowance, dated Jan. 28, 2015, by the USPTO, re U.S. Appl. No. 29/455,618".
"Notice of Allowance dated Oct. 12, 2012, by the USPTO, re U.S. Appl. No. 12/683,804".
"Office Action / Restriction dated Mar. 29, 2016, by the USPTO, re U.S. Appl. No. 14/565,962".
"Office Action dated Apr. 19, 2012, by the USPTO, re U.S. Appl. No. 12/821,863".
"Office Action dated Jan. 18, 2013, by the USPTO, re U.S. Appl. No. 12/748,127".
"Office Action dated Jan. 2, 2014, by the USPTO, re U.S. Appl. No. 13/866,121".
"Office Action dated Jan. 21, 2009, by the USPTO, re U.S. Appl. No. 10/833,921".
"Office Action dated Jan. 27, 2012, by the USPTO, re U.S. Appl. No. 12/683,804".
"Office Action dated Jul. 16, 2007, by the USPTO, re U.S. Appl. No. 10/831,467".
"Office Action dated Jul. 16, 2012, by the USPTO, re U.S. Appl. No. 12/683,804".
"Office Action dated Jul. 28, 2008, by the USPTO, re U.S. Appl. No. 10/833,921".
"Office Action dated Jun. 1, 2016, by the USPTO, re U.S. Appl. No. 14/565,962".
"Office Action dated Jun. 24, 2009, by the USPTO, re U.S. Appl. No. 10/831,467".
"Office Action dated Mar. 8, 2012, by the USPTO, re U.S. Appl. No. 14/262,880".
"Office Action dated Mar. 9, 2016, by the USPTO, re U.S. Appl. No. 12/821,663".
"Office Action dated May 23, 2013, by the USPTO, re U.S. Appl. No. 12/683,900".
"Office Action dated May 29, 2007, by the USPTO, re U.S. Appl. No. 10/833,921".
"Office Action dated May 7, 2008, by the USPTO, re U.S. Appl. No. 10/831,467".
"Office Action dated Nov. 14, 2008, by the USPTO, re U.S. Appl. No. 10/831,467".
"Office Action dated Oct. 11, 2011, by the USPTO, re U.S. Appl. No. 12/277,849".
"Office Action dated Oct. 7, 2013, by the USPTO, re U.S. Appl. No. 13/843,525".
"Office Action dated Sep. 18, 2007, by the USPTO, re U.S. Appl. No. 10/833,921".
"Office Action dated Sep. 29, 2014, by the USPTO, re U.S. Appl. No. 13/339,640".
"SPM QEM2500 GL Well Service Plunger Pump, Generic Operation Instruction and Service Manual, May 8, 2010".
"Suction Requirements for Reciprocating Power Pumps, p. 59, Figure 3.4 Composite Pump Dynamics".
"Supplemental Notice of Allowance dated Mar. 21, 2012, by the USPTO, re U.S. Appl. No. 12/277,849".

* cited by examiner

MONITORING LUBRICANT IN HYDRAULIC FRACTURING PUMP SYSTEM

CROSS-REFERENCE TO RELATED APPLICATION

This application claims priority to, and the benefit of the filing date of, U.S. patent application No. 62/240,224, filed Oct. 12, 2015, the entire disclosure of which is hereby incorporated herein by reference.

TECHNICAL FIELD

This disclosure relates in general to hydraulic fracturing pump systems and, in particular, to monitoring hydraulic fracturing pump systems.

BACKGROUND OF THE DISCLOSURE

Several systems may be used to facilitate oil and gas exploration and production operations. One example is a hydraulic fracturing pump system, which pumps fluid to a wellhead for the purpose of, for example, propagating fractures in a formation through which a wellbore extends, the wellhead being the surface termination of the wellbore. The hydraulic fracturing pump system may include an engine, a transmission operably coupled to the engine, and a reciprocating pump assembly operably coupled to the transmission, with the engine driving the reciprocating pump assembly via the transmission. However, different aspects associated with the operation of the hydraulic fracturing pump system may not be able to be sufficiently monitored or controlled, remotely or otherwise. For example, lubrication conditions associated with the operation of the reciprocating pump assembly may not be able to be sufficiently monitored or controlled, increasing the risk of pump failure resulting from poor or otherwise unsatisfactory lubrication conditions. For another example, engine or transmission conditions associated with the operation of the hydraulic fracturing pump system may not be able to be sufficiently monitored or controlled, reducing efficiencies and/or decreasing the operational lives of one or more of the engine, transmission, and reciprocating pump assembly. Therefore, what is needed is a system, method, or apparatus that addresses one or more of these issues, and/or other issue(s).

SUMMARY

In a first aspect, there is provided a monitoring system configured to monitor a hydraulic fracturing pump system, the hydraulic fracturing pump system including an engine, a transmission operably coupled to the engine, and a reciprocating pump assembly operably coupled to the transmission so that the engine is configured to drive the reciprocating pump assembly via the transmission, the monitoring system including: a gateway, the gateway including one or more processors and a non-transitory computer readable medium operably coupled thereto; one or more sensors configured to: be operably coupled to the reciprocating pump assembly; measure respective physical properties associated with the reciprocating pump assembly; be in communication with the gateway; and transmit to the gateway sensor data associated with the respective physical properties configured to be measured by the one or more sensors; and one or more antennas configured to be operably coupled to the gateway and to transmit the sensor data and/or representative data based on the sensor data; wherein the gateway is configured to be in communication with at least one of the engine and the transmission via a controller area network (CAN) bus.

In an exemplary embodiment, the CAN bus uses J1939 protocol.

In another exemplary embodiment, the gateway is configured to be in communication with the at least one of the engine and the transmission so that the gateway is configured to receive, via the CAN bus, a message from the at least one of the engine and the transmission.

In yet another exemplary embodiment, the gateway is configured to be in communication with the at least one of the engine and the transmission so that the gateway is configured to send, via the CAN bus, a message to the at least one of the engine and the transmission.

In certain exemplary embodiments, the message sent by the gateway contains the sensor data measured by the one or more sensors and/or representative data based on the sensor data measured by the one or more sensors.

In an exemplary embodiment, the gateway further includes a plurality of instructions stored on the non-transitory computer readable medium and executable by the one or more processors; wherein the plurality of instructions, when executed by the one or more processors, configure the gateway to be in communication with the at least one of the engine and the transmission via the CAN bus.

In another exemplary embodiment, the hydraulic fracturing pump system includes first and second configuration files stored on the non-transitory computer readable medium; wherein the first configuration file configures the gateway to receive a message, via the CAN bus, from the at least one of the engine and the transmission; and wherein the second configuration file configures the gateway to send a message, via the CAN bus, to the at least one of the engine and the transmission.

In yet another exemplary embodiment, the one or more antennas are configured to transmit the sensor data, and/or representative data based the sensor data, to an application server; and wherein the gateway is configured to receive, via the one or more antennas, a message from the application server.

In a second aspect, there is provided a monitorable hydraulic fracturing pump system that includes an engine; a transmission operably coupled to the engine; a reciprocating pump assembly operably coupled to the transmission so that the reciprocating pump assembly is configured to be driven by the engine via the transmission; one or more sensors operably coupled to the reciprocating pump assembly and configured to measure respective physical properties of the reciprocating pump assembly during its operation; a gateway configured to be in communication with the one or more sensors to receive sensor data associated with respective physical properties; and a controller area network (CAN) bus with which each of the engine, the transmission, and the gateway is configured to be in communication; wherein the gateway is configured to be in communication with each of the engine and the transmission, via the CAN bus, so that the engine and the transmission may be monitored using the gateway.

In an exemplary embodiment, the CAN bus uses J1939 protocol.

In another exemplary embodiment, the gateway is configured to be in communication with each of the engine and the transmission so that the gateway is configured to receive, via the CAN bus, respective messages from the engine and the transmission.

In yet another exemplary embodiment, the gateway is configured to be in communication with each of the engine and the transmission so that the gateway is configured to send, via the CAN bus, respective messages to the engine and the transmission to control the respective operations thereof.

In certain exemplary embodiments, the respective messages sent by the gateway contain the sensor data measured by the one or more sensors and/or representative data based on the sensor data measured by the one or more sensors.

In an exemplary embodiment, the gateway further includes a plurality of instructions stored on the non-transitory computer readable medium and executable by the one or more processors; wherein the plurality of instructions, when executed by the one or more processors, configure the gateway to be in communication with each of the engine and the transmission via the CAN bus.

In another exemplary embodiment, the monitorable hydraulic fracturing pump system includes first and second configuration files stored on the non-transitory computer readable medium; wherein the first configuration file configures the gateway to receive a message, via the CAN bus, from at least one of the engine and the transmission; and wherein the second configuration file configures the gateway to send a message, via the CAN bus, to the at least one of the engine and the transmission.

In a third aspect, there is provided a method of monitoring a hydraulic fracturing pump system, the hydraulic fracturing pump system including an engine, a transmission operably coupled to the engine, and a reciprocating pump assembly operably coupled to the transmission so that the engine is configured to drive the reciprocating pump assembly via the transmission, the method including: receiving, using a gateway, sensor data associated with respective physical properties of the reciprocating pump assembly; receiving, using the gateway, a first message from either the engine or the transmission; and monitoring, using the gateway, one or more of the engine, the transmission, and the reciprocating pump assembly, including at least one of: determining one or more alarms to be activated based on at least one of the sensor data and the first message received from either the engine or the transmission; and determining one or more adjustments to the operation of the hydraulic fracturing pump system based on at least one of the sensor data and the first message received from either the engine or the transmission.

In an exemplary embodiment, the first message is received from either the engine or the transmission via a controller area network (CAN) bus with which each of the gateway, the engine, and the transmission is in communication.

In another exemplary embodiment, the CAN bus uses J1939 protocol.

In yet another exemplary embodiment, the method includes sending, using the gateway, a second message to either the engine or the transmission.

In certain exemplary embodiments, the second message contains the sensor data and/or representative data based on the sensor data.

In an exemplary embodiment, the first message is received from either the engine or the transmission via a controller area network (CAN) bus with which each of the gateway, the engine, and the transmission is in communication; and wherein the second message is sent to either the engine or the transmission via the CAN bus with which each of the gateway, the engine, and the transmission is in communication.

In another exemplary embodiment, the method includes configuring CAN message reception and transmission via first and second configuration files, respectively.

In yet another exemplary embodiment, the second message is sent to either engine or the transmission to adjust the operation thereof.

In certain exemplary embodiments, the method includes sending, using the gateway, a second message to a computing device; wherein the second message is sent to the computing device via a network; and wherein the second message contains the sensor data and/or representative data based on the sensor data.

In a fourth aspect, there is provided a monitoring apparatus adapted to monitor lubricant in a hydraulic fracturing pump system, the apparatus including: a gateway, including one or more processors and a non-transitory computer readable medium operably coupled thereto; and one or more sensors configured to be in communication with the gateway; wherein the one or more sensors are configured to measure: a quality of the lubricant; a pressure of the lubricant; and a temperature of the lubricant; wherein the gateway is configured to receive, from the one or more sensors, sensor data associated with the quality of the lubricant, the pressure of the lubricant, and the temperature of the lubricant; and wherein, to monitor the lubricant, the gateway is configured to: store the sensor data on the non-transitory computer readable medium; transmit to another computing device the sensor data and/or representative data based on the sensor data; visually indicate a status of the quality of the lubricant; visually indicate a status of the pressure of the lubricant; visually indicate a status of the temperature of the lubricant; or any combination thereof.

In an exemplary embodiment, the hydraulic fracturing pump system includes a reciprocating pump assembly, a lubricant source, and a fluid line via which the reciprocating pump assembly is in fluid communication with the lubricant source; and wherein the quality, pressure, and temperature of the lubricant is the quality, pressure, and temperature, respectively, of the lubricant when the lubricant is in the fluid line.

In another exemplary embodiment, the one or more sensors include: a first sensor configured to measure the quality of the lubricant; a second sensor configured to measure the pressure of the lubricant; and a third sensor configured to measure the temperature of the lubricant; wherein each of the first, second, and third sensors is configured to be in communication with the gateway.

In yet another exemplary embodiment, the apparatus further includes a sensor connector, the sensor connector including: a body, the body defining a longitudinally-extending flow passage through which the lubricant is configured to flow; and a plurality of radially-extending openings formed in the body; wherein the first, second, and third sensors are configured to be connected to the body via respective ones of the radially-extending openings.

In certain exemplary embodiments, the hydraulic fracturing pump system includes an engine, a transmission operably coupled to the engine, and a reciprocating pump assembly operably coupled to the transmission, the reciprocating pump assembly including a crankshaft via which the transmission is operably coupled to the reciprocating pump so that the engine is configured to rotate the crankshaft, via the transmission, to drive the reciprocating pump assembly; wherein the apparatus further includes a crankshaft rotation sensor configured to be in communication with the gateway; and wherein the crankshaft rotation sensor is configured to count the number of times the crankshaft rotates.

In an exemplary embodiment, the crankshaft rotation sensor includes a proximity sensor.

In another exemplary embodiment, the apparatus includes an element configured to rotate along with the crankshaft; wherein the proximity sensor includes a distal end configured to be proximate the element when the element rotates along with the crankshaft.

In yet another exemplary embodiment, the element defines first and second outer-diameter transition regions; wherein the first and second outer-diameter transition regions are circumferentially spaced; and wherein the proximity sensor is configured to detect each of the two outer-diameter transition regions as it rotates past the distal end of the proximity sensor.

In certain exemplary embodiments, the element includes a collar, the collar including first and second arcuate sections defining first and second outer diameters, respectively; wherein the first and second diameters are different in that the first outer diameter is greater than the second outer diameter; and wherein the difference between the first and second outer diameters defines the first and second outer-diameter transition regions.

In an exemplary embodiment, the collar is configured to be operably coupled to a rotary union of the reciprocating pump assembly.

In another exemplary embodiment, the first and second outer-diameter transition regions are circumferentially spaced by about 180 degrees.

In yet another exemplary embodiment, the apparatus includes a GPS antenna configured to be operably coupled to the gateway; and one or more antennas configured to be operably coupled to the gateway; wherein the gateway is configured to: interpret GPS location coordinates received via the GPS antenna; and send information identifying the location of the hydraulic fracturing pump system to another computing device via the one or more other antennas.

In certain exemplary embodiments, the one or more antennas include at least one of a cellular antenna and a satellite antenna.

In an exemplary embodiment, to monitor the lubricant, the gateway is configured to: store the sensor data on the non-transitory computer readable medium; transmit to the another computing device the sensor data and/or the representative data based on the sensor data; visually indicate the status of the quality of the lubricant; visually indicate the status of the pressure of the lubricant; and visually indicate the status of the temperature of the lubricant.

In another exemplary embodiment, the gateway is configured to visually indicate the status of the quality of the lubricant by activating one of a plurality of LED states.

In a fifth aspect, there is provided a method of monitoring lubricant in a hydraulic fracturing pump system positioned at a location, the hydraulic fracturing pump system including a reciprocating pump assembly, the method including: detecting, using a gateway, one or more events associated with the lubricant in the hydraulic fracturing pump system, wherein the detected one or more events include at least one of the following: a temperature of the lubricant has exceeded a first threshold; the temperature of the lubricant has not reached a second threshold; a pressure of the lubricant pressure has exceeded a third threshold; the pressure of the lubricant has not reached a fourth threshold; and the quality of the lubricant has changed; identifying, using a GPS antenna operably coupled to the gateway, the location of the hydraulic fracturing pump system; and activating, using the gateway and/or a computing device in communication therewith, one or more alarms to indicate the existence of the detected one or more events and the location thereof.

In an exemplary embodiment, detecting the one or more events includes: measuring, using one or more sensors operably coupled to the gateway, one or more physical properties associated with the reciprocating pump assembly; sending sensor data associated with the one or more physical properties from the one or more sensors to the gateway; and comparing, using the gateway or a computing device in communication therewith, the sensor data or representative data based thereon with one or more thresholds.

In another exemplary embodiment, identifying the location of the hydraulic fracturing pump system includes: interpreting, using the gateway, GPS location coordinates received via the GPS antenna; and sending information identifying the location of the hydraulic fracturing pump system to another computing device via one or more other antennas that are operably coupled to the gateway.

In yet another exemplary embodiment, the one or more other antennas include at least one of a cellular antenna and a satellite antenna.

In certain exemplary embodiments, the hydraulic fracturing pump system includes a reciprocating pump assembly, a lubricant source, and a fluid line via which the reciprocating pump assembly is in fluid communication with the lubricant source; and wherein the quality, pressure, and temperature of the lubricant is the quality, pressure, and temperature, respectively, of the lubricant when the lubricant is in the fluid line.

In an exemplary embodiment, detecting the one or more events includes: connecting a sensor connector to the fluid line so that the sensor connector is in fluid communication with the fluid line; connecting one or more sensors to the sensor connector, wherein the one or more sensors include at least one of the following: a pressure sensor, a temperature sensor, and an oil quality sensor; wherein the one or more sensors are in communication with the gateway.

In another exemplary embodiment, the detected one or more events include at least one of the following: the reciprocating pump assembly has become active; the reciprocating pump assembly has become inactive; and the operational life of the reciprocating pump assembly has reached or exceeded a fifth threshold.

In a sixth aspect, there is provided a monitoring apparatus adapted to monitor lubricant in a hydraulic fracturing pump system, the hydraulic fracturing pump system comprising: an engine; a transmission operably coupled to the engine; a reciprocating pump assembly operably coupled to the transmission, the reciprocating pump assembly comprising a crankshaft via which the transmission is operably coupled to the reciprocating pump so that the engine is configured to rotate the crankshaft, via the transmission, to drive the reciprocating pump assembly; a lubricant source; and a fluid line via which the reciprocating pump assembly is in fluid communication with the lubricant source, wherein the monitoring apparatus comprises: a gateway, comprising one or more processors and a non-transitory computer readable medium operably coupled thereto; a plurality of sensors configured to be in communication with the gateway, the plurality of sensors comprising: a first sensor configured to measure a quality of the lubricant when the lubricant is in the fluid line; a second sensor configured to measure a pressure of the lubricant when the lubricant is in the fluid line; a third sensor configured to measure a temperature of the lubricant when the lubricant is in the fluid line; and a crankshaft rotation sensor configured to be in communication with the gateway, wherein the crankshaft rotation sensor is configured to count the number of times the crankshaft rotates; a GPS antenna configured to be operably coupled to the gateway; and one or more antennas configured to be operably coupled to the gateway; wherein the gateway is configured to receive, from the plurality of sensors, sensor data associated with the quality of the lubricant, the pressure of the lubricant, and the temperature of the lubricant; wherein the gateway is configured to: store the sensor data on the non-transitory computer readable medium, visually indicate a status of the quality of the lubricant by activating one of a plurality of LED states, visually indicate a status of the pressure of the lubricant, and visually indicate a status of the temperature of the lubricant, so that a need for inspection of, and/or corrective action with respect to, the hydraulic fracturing pump system is able to be communicated to personnel located at the hydraulic fracturing pump system; and wherein the gateway is further configured to: transmit to another computing device the sensor data and/or representative data based on the sensor data, interpret GPS location coordinates received via the GPS antenna, and transmit information identifying the location of the hydraulic fracturing pump system to the another computing device via the one or more other antennas, so that (i) the need for the inspection of, and/or the corrective action with respect to, the hydraulic fracturing pump system, and (ii) the location of the hydraulic fracturing pump system, are able to be communicated to the another computing device in order to alert a user of the another computing device of the need for the inspection and/or corrective action and the location of that need.

Other aspects, features, and advantages will become apparent from the following detailed description when taken in conjunction with the accompanying drawings, which are a part of this disclosure and which illustrate, by way of example, principles of the inventions disclosed.

DESCRIPTION OF FIGURES

The accompanying drawings facilitate an understanding of the various embodiments.

DETAILED DESCRIPTION

Figure 1:
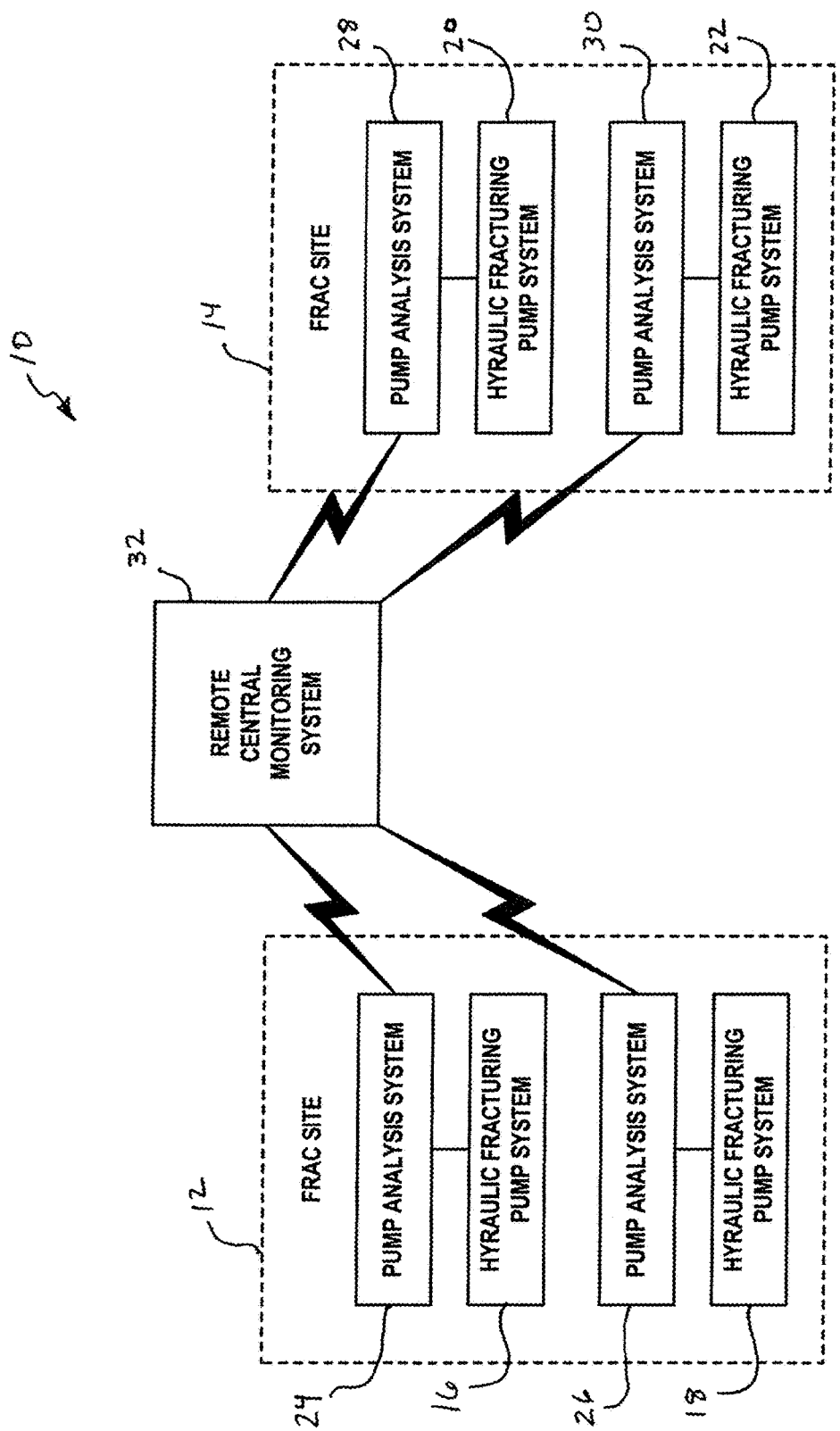
FIG. 1 is a diagrammatic illustration of a system for monitoring different hydraulic fracturing pump systems located at different frac sites according to an exemplary embodiment, the system including a remote central monitoring system and different pump analysis systems, each of which is operably coupled to a corresponding hydraulic fracturing pump system.

In an exemplary embodiment, as illustrated in FIG. 1, a system for monitoring hydraulic fracturing pump systems is generally referred to by the reference numeral 10 and includes different frac sites 12 and 14. Hydraulic fracturing pump systems 16 and 18 are located at the frac site 12. Likewise, hydraulic fracturing pump systems 20 and 22 are located at the frac site 14. Each of the frac sites 12 and 14 may be used in oil and gas exploration and production operations. In addition to the hydraulic fracturing pump systems 16 and 18, or 20 and 22, each of the frac sites 12 and 14 includes other components and systems such as, for example, water trucks, sand trucks, chemicals, manifold assemblies and trailers, blenders, etc. Each of the hydraulic fracturing pump systems 16, 18, 20, and 22 is adapted to be in fluid communication with a manifold assembly (not shown), receiving fracturing slurry or fluid at a relatively low pressure and discharging the fracturing slurry or fluid at a relatively high pressure (up to 15,000-30,000 psi); the pressurized fracturing slurry or fluid is then directed from the manifold assembly to a wellhead, at which a wellbore terminates, in order to hydraulically fracture a subterranean formation that is penetrated by the wellbore. In several exemplary embodiments, instead of, or in addition to, the hydraulic fracturing pump systems 16 and 18, one or more other hydraulic fracturing pump systems are located at the frac site 12. Likewise, instead of, or in addition to, the hydraulic fracturing pump systems 20 and 22, one or more other hydraulic fracturing pump systems are located at the frac site 14.

Pump monitoring systems 24 and 26 are located at the frac site 12, and are operably coupled to the hydraulic fracturing pump systems 16 and 18, respectively. Similarly, pump monitoring systems 28 and 30 are located at the frac site 14, and are operably coupled to the hydraulic fracturing pump systems 20 and 22, respectively. A remote central monitoring system 32 is in communication with each of the pump monitoring systems 24, 26, 28, and 30. In several exemplary embodiments, the remote central monitoring system 32 is located at a central location, which is remotely located from the frac sites 12 and 14. In several exemplary embodiments, the remote central monitoring system 32 is located at one or more locations, which are remotely located from the frac sites 12 and 14. In several exemplary embodiments, the remote central monitoring system 32, or at least a portion thereof, is located at the frac site 12, the frac site 14, or both of the frac sites 12 and 14. In several exemplary embodiments, the remote central monitoring system 32 is located within a control van, which is located at the frac site 12 or 14. In several exemplary embodiments, the remote central monitoring system 32, or at least a portion thereof, is, includes, or is part of, one or more of the pump analysis systems 24, 26, 28, and 30.

In several exemplary embodiments, the remote central monitoring system 32 is in communication with each of the pump analysis systems 24, 26, 28, and 30 via a network (not shown); in several exemplary embodiments, the network includes the Internet, one or more local area networks, one or more wide area networks, one or more cellular networks, one or more wireless networks, one or more voice networks, one or more data networks, a GPS network, one or more Wi-Fi networks, one or more satellite networks, one or more communication systems, and/or any combination thereof.

Figure 2:
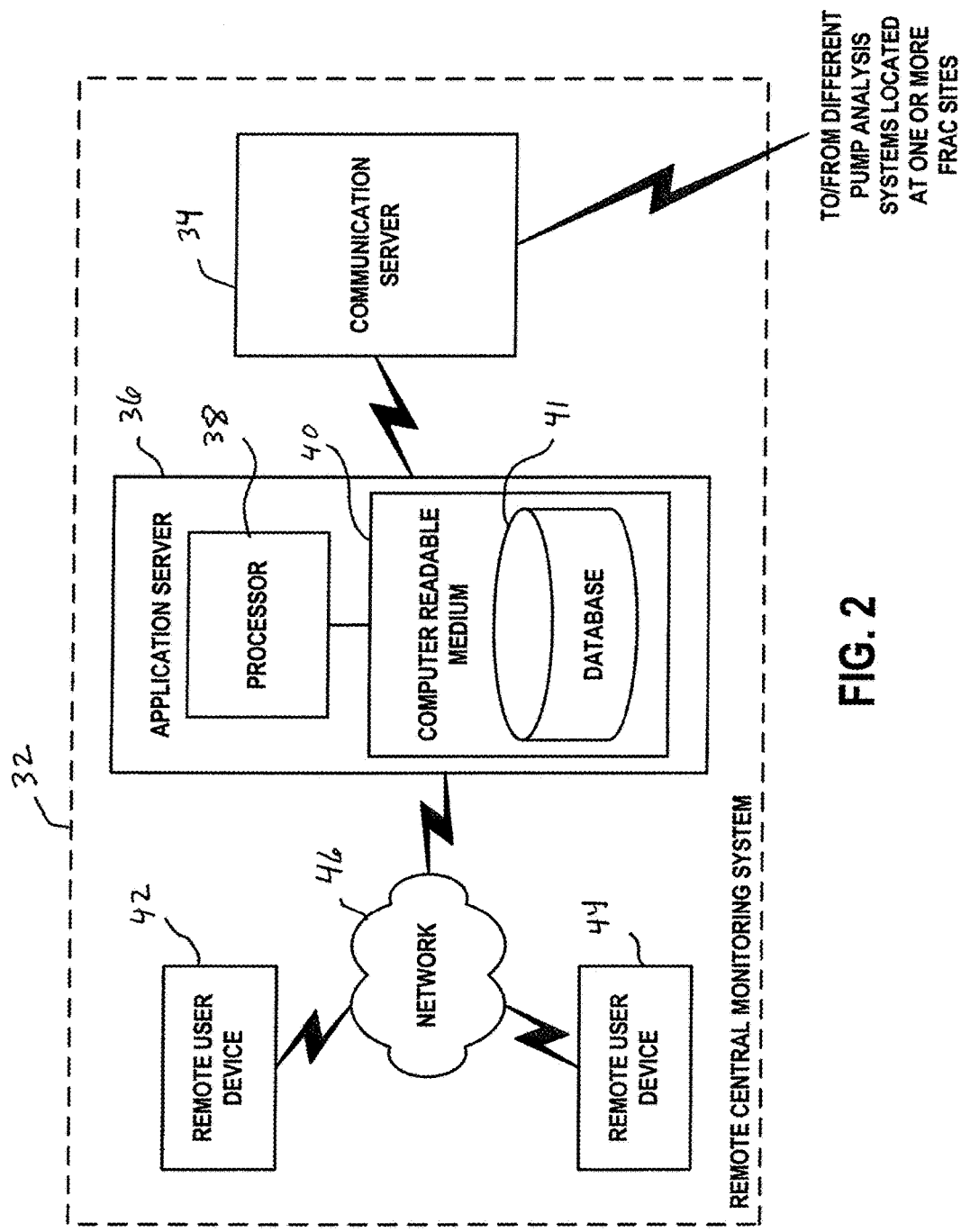
FIG. 2 is a diagrammatic illustration of the remote central monitoring system of FIG. 1, according to an exemplary embodiment.

In an exemplary embodiment, as illustrated in FIG. 2 with continuing reference to FIG. 1, the remote central monitoring system 32 includes a communication server 34, which is in communication with each of the pump analysis systems 24, 26, 28, and 30. An application server 36 is in communication with the communication server 34. The application server 36 includes one or more computer processors 38 and a non-transitory computer readable medium 40 operably coupled thereto; a plurality of instructions are stored on the non-transitory computer readable medium 40, the instructions being accessible to, and executable by, the one or more computer processors 38. In an exemplary embodiment, the communication server 34 and the application server 36 are combined. The computer readable medium 40 includes a database 41. Remote user devices 42 and 44 are in communication with the application server 36 via a network 46. In several exemplary embodiments, each of the remote user devices 42 and 44 is a personal computer, PDA, smartphone, cell phone, or other type of computing device. In several exemplary embodiments, one or both of the remote user devices 42 and 44 are remotely located from the communication server 34 and/or the application server 36.

In several exemplary embodiments, the network 46 includes the Internet, one or more local area networks, one or more wide area networks, one or more cellular networks, one or more wireless networks, one or more voice networks, one or more data networks, one or more communication systems, and/or any combination thereof. In several exemplary embodiments, the one or more computer processors 38, and/or the computer readable medium 40, are distributed between two or more of the communication server 34, the application server 36, and the remote user devices 42 and 44. In several exemplary embodiments, the remote central monitoring system 32 provides the infrastructure to allow global communication between users and each of the hydraulic fracturing pump systems 16, 18, 20, and 22, and/or other pump systems. In several exemplary embodiments, the remote central monitoring system 32 is cloud based and provides a global presence, allowing each of the pump analysis systems 24, 26, 28, and 30 to communicate back to a central communication endpoint.

Figure 3:
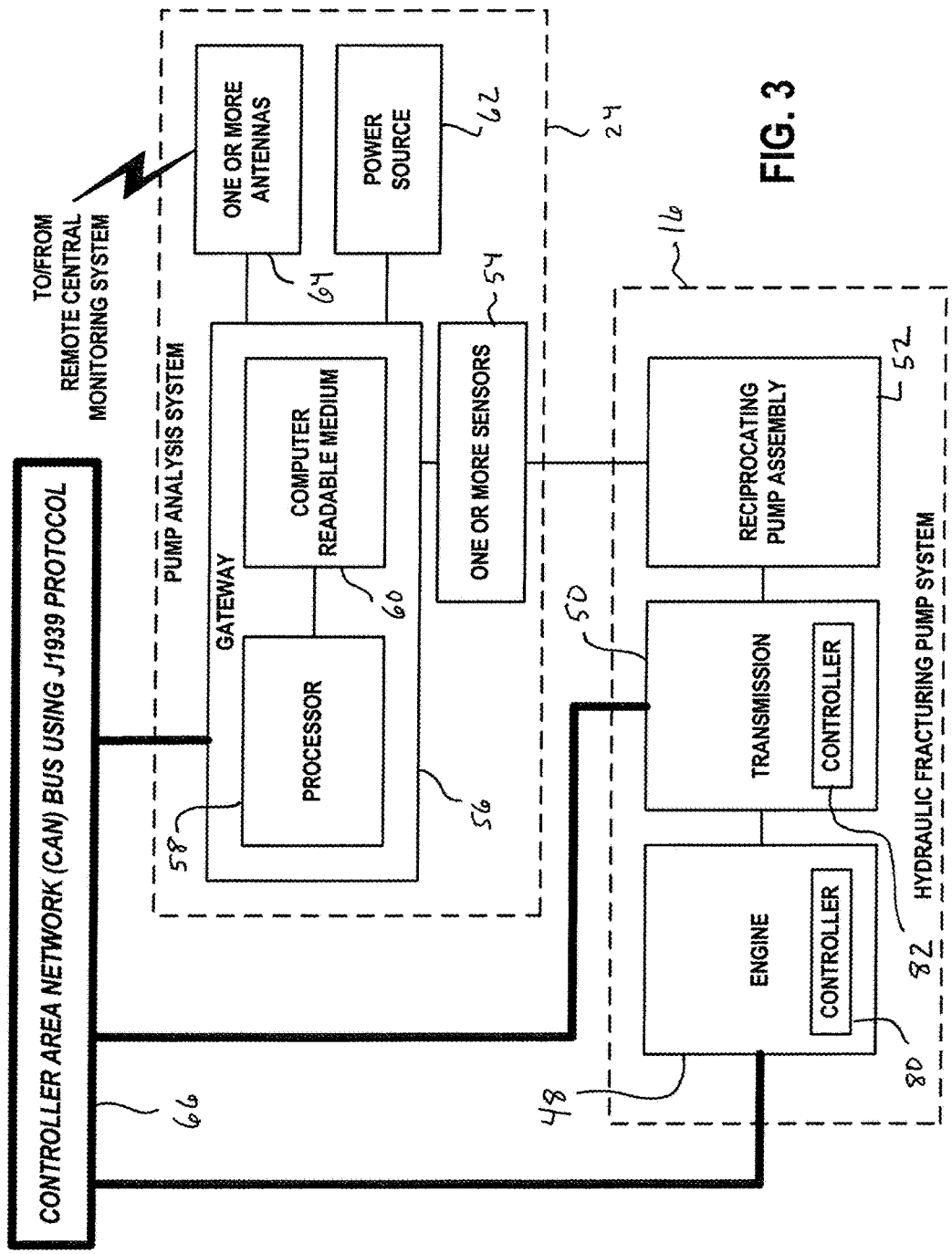
FIG. 3 is a diagrammatic illustration of one of the hydraulic fracturing pump systems of FIG. 1, and the corresponding one of the pump analysis systems of FIG. 1 operably coupled to the hydraulic fracturing pump system, according to an exemplary embodiment.

In an exemplary embodiment, as illustrated in FIG. 3 with continuing reference to FIGS. 1 and 2, the hydraulic fracturing pump system 16 includes an engine (or motor) 48, a transmission 50 operably coupled to the engine 48, and a reciprocating pump assembly 52 operably coupled to the transmission 50. The reciprocating pump assembly 52 includes a power end (not shown) including a crankshaft, via which the transmission 50 is operably coupled to the reciprocating pump assembly 52; the engine 48 is adapted to rotate or drive the crankshaft via the transmission 50, thereby driving the reciprocating pump assembly 52. When so driven, plungers (not shown) of the reciprocating pump assembly 52 reciprocate, thereby pressurizing fracturing slurry or fluid. In an exemplary embodiment, the engine 48 is, includes, or is part of, a diesel engine. In several exemplary embodiments, the engine 48 is, includes, or is part of, a motor. In several exemplary embodiments, the engine 48 is, includes, or is part of, an electric motor. In several exemplary embodiments, the engine 48 is, includes, or is part of, a turbine. In several exemplary embodiments, the engine 48 is, includes, or is part of, a hydraulic unit. In several exemplary embodiments, the transmission 50 is, includes, or is part of, a pump drivetrain, which may include one or more gear reducers, linkages, etc. In several exemplary embodiments, the transmission 50 is, includes, or is part of, a hydraulic unit.

As shown in FIG. 3, the pump analysis system 24 includes one or more sensors 54, which are operably coupled to the reciprocating pump assembly 52 and are adapted to measure one or more physical properties associated with the reciprocating pump assembly 52. In several exemplary embodiments, at least one of the one or more sensors 54 is connected to the reciprocating pump assembly 52. In several exemplary embodiments, at least one of the one or more sensors 54 is operably positioned, relative to the reciprocating pump assembly 52, so that the one or more physical properties associated with the reciprocating pump assembly 52 may be measured. In several exemplary embodiments, the one or more sensors 54 include one or more of the following types of sensors: position sensor, proximity sensor, inductive sensor, temperature sensor, pressure sensor, vibration sensor, and accelerometer. In several exemplary embodiments, the one or more sensors 54 include one or more different combinations of the foregoing types of sensors.

A gateway 56 is in communication with each of the one or more sensors 54. The gateway 56 includes one or more computer processors 58 and a non-transitory computer readable medium 60 operably coupled thereto; a plurality of instructions are stored on the non-transitory computer readable medium 60, the instructions being accessible to, and executable by, the one or more processors 58. In several exemplary embodiments, the gateway 56 is adapted to collect real-time sensor data from the one or more sensors 54, execute analysis algorithms using the sensor data, and report data back to the remote central monitoring system 32. In several exemplary embodiments, the gateway 56 includes a housing that is mounted on the reciprocating pump assembly 52. In several exemplary embodiments, the gateway 56 includes a housing that is mounted on at least one of the engine 48, the transmission 50, and the reciprocating pump assembly 52. In several exemplary embodiments, the gateway 56 includes additional components such as, for example, one or more data acquisition units, one or more transceivers, one or more transmitters, one or more receivers, one or more microcontrollers, or any combination thereof; in several exemplary embodiments, the one or more processors 58 and/or the non-transitory computer readable medium 60 are part of one or more of these additional components. In several exemplary embodiments, the gateway 56 includes an analytics engine for intelligent sensor analysis.

A power source 62 is operably coupled to the gateway 56 and is adapted to supply electrical power thereto; in several exemplary embodiments, the power source 62 also supplies electrical power to the one or more sensors 54. In an exemplary embodiment, the power source 62 is, or includes, one or more batteries. One or more antennas 64 are operably coupled to the gateway 56. As noted above, the pump analysis system 24 is in communication with the remote central monitoring system 32; in several exemplary embodiments, the gateway 56 is in communication with the communication server 34, via the one or more antennas 64, so that the pump analysis system 24 is in communication with the remote central monitoring system 32. In several exemplary embodiments, the one or more antennas 64 include one or more of a cellular antenna, a Wi-Fi antenna, a satellite antenna, and a GPS antenna. In several exemplary embodiments, the one or more antennas 64 form an antenna array, which is a transmission array used by the transceiver(s) of the gateway 56 for Wi-Fi communication, satellite communication, GPS communication, cellular communication, or any combination thereof.

With continuing reference to FIG. 3, in an exemplary embodiment, the hydraulic fracturing pump system 16 is in communication with the pump analysis system 24 via a controller area network (CAN) bus 66. More particularly, each of the engine 48, the transmission 50, and the gateway 56 is in communication with the CAN bus 66; in several exemplary embodiments, the CAN bus 66 uses J1939 protocol. As a result, in several exemplary embodiments, using the J1939 protocol, the engine 48 is configured to communicate with each of the gateway 56 and the transmission 50, directly and without the use of a go-between host computer. To so communicate, the engine 48 is configured, via the CAN bus, to receive messages from each of the gateway 56 and the transmission 50, and to send messages to each of the gateway 56 and the transmission 50. Likewise, in several exemplary embodiments, using the J1939 protocol, the transmission 50 is configured to communicate with each of the gateway 56 and the engine 48, directly and without the use of a go-between host computer. To so communicate, the transmission 50 is configured, via the CAN bus 66, to receive messages from each of the gateway 56 and the engine 48, and to send messages to each of the gateway 56 and the engine 48. Likewise, in several exemplary embodiments, using the J1939 protocol, the gateway 56 is configured to communicate with each of the transmission 50 and the engine 48, directly and without the use of a go-between host computer. To so communicate, the gateway 56 is configured, via the CAN bus 66, to receive messages from each of the transmission 50 and the engine 48, and to send messages to each of the transmission 50 and the engine 48.

In several exemplary embodiments, the hydraulic fracturing pump system 16, the pump analysis system 24, and the CAN bus 66 are all mounted on a single transportable unit such as, for example, a hydraulic fracturing truck, a skid, a skid that is mounted on a hydraulic fracturing truck, etc. As a result, in several exemplary embodiments, communication between the hydraulic fracturing pump system 16 and the pump analysis system 24 is not dependent upon a system or component located at the frac site 12 and external to the single transportable unit; for example, such communication is not dependent upon a control unit positioned within a control van located at the frac site 12 and external to the single transportable unit.

In several exemplary embodiments, the hydraulic fracturing pump system 16 includes the pump analysis system 24 and the CAN bus 66. In several exemplary embodiments, the hydraulic fracturing pump system 16 includes the pump analysis system 24 and the CAN bus 66, and the hydraulic fracturing pump system 16—including the pump analysis system 24—is mounted on a single transportable unit such as, for example, a hydraulic fracturing truck, a skid, a skid that is mounted on a hydraulic fracturing truck, etc. As a result, in several exemplary embodiments, communication between the gateway 56 and each of the engine 48 and the transmission 50 is not dependent upon a system or component located at the frac site 12 and external to the single transportable unit; for example, such communication is not dependent upon a control unit positioned within a control van located at the frac site 12 and external to the single transportable unit.

In operation, in several exemplary embodiments, the hydraulic fracturing pump system 16 operates in accordance with the foregoing. During this operation, the one or more sensors 54 of the pump analysis system 24 measure one or more physical properties associated with the reciprocating pump assembly 52. The gateway 56 of the pump analysis system 24 receives from the one or more sensors 54 sensor data associated with the one or more physical properties measured by the one or more sensors 54, thereby collecting the sensor data. In several exemplary embodiments, the one or more processors 58 analyze, condition, or otherwise process the sensor data to determine one or more operating parameters of the reciprocating pump assembly 52. In several exemplary embodiments, the sensor data as received, the sensor data as processed, the determined one or more operating parameters, or any combination thereof, are stored on the computer readable medium 60. In several exemplary embodiments, via the one or more antennas 64, the gateway 56 sends the sensor data as received, the sensor data as processed, the determined one or more operating parameters, or any combination thereof, to the remote central monitoring system 32. The application server 36 receives the sensor data as received, the sensor data as conditioned or otherwise processed, the determined one or more operating parameters, or any combination thereof, via the communication server 34, and stores this information in whole or in part on the computer readable medium 40 including, in several exemplary embodiments, in the database 41. Remote users access this information via the remote user devices 42 and/or 44 and the network 46, communicating with the application server 36 so that the information is displayed on the remote user devices 42 and/or 44, and/or stored thereon for later viewing. As a result, the operation, or status, of the reciprocating pump assembly 52 can be remotely monitored. In several exemplary embodiments, the remote central monitoring system 32 stores the data on the application server 34 for presentation to users using, for example, a web browser displayed on, for example, the remote user device 42 or 44.

In several exemplary embodiments, the reciprocating pump assembly 52 is remotely monitored, via the one or more antennas 64 using a system other than remote central monitoring system 32; for example, the reciprocating pump assembly 52 may be monitored from a control van located at the frac site 12, with a control unit located in the control van communicating with the gateway 56 via the one or more antennas 46.

In several exemplary embodiments, the pump analysis system 24 provides local data processing, collection, and analysis for the hydraulic fracturing pump system 16. In several exemplary embodiments, the gateway 56 collects and analyzes sensor data onsite in real-time to detect the status of the hydraulic fracturing pump system 16 including the reciprocating pump assembly 52, detect any failures of the hydraulic fracturing pump system 16 including the reciprocating pump assembly 52, predict failures of the hydraulic fracturing pump system 16 including the reciprocating pump assembly 52, and detect process anomalies of the hydraulic fracturing pump system 16 including the reciprocating pump assembly 52. In several exemplary embodiments, via the one or more antennas 46, the gateway 56 reports alarms, events, status, and history back to the remote central monitoring system 32, which then delivers the data to users via the network 46 and the remote user devices 42 and/or 44. In several exemplary embodiments, by monitoring the operation, or status, of the reciprocating pump assembly 52 using the system 10, an analyst may better predict and report potential failures based on the monitored information.

In several exemplary embodiments, the gateway 56 is programmed with CAN J1939 data transmission and receiving capability. In several exemplary embodiments, the gateway 56 is programmed to implement the J1939 protocol in the CAN transceiver. In several exemplary embodiments, the gateway 56 is programmed so that sensor data received from the one or more sensors 54, and/or data representative of, or based on, the received sensor data, is allowed to be transmitted via the CAN bus 66. In several exemplary embodiments, the gateway 56 is programmed to allow configuration of CAN message transmission via a transmission configuration file. In several exemplary embodiments, the gateway 56 is programmed to allow configuration of CAN message reception via a receive configuration file. In several exemplary embodiments, the gateway 56 is programmed to allow reception of CAN messages from other devices in communication with the CAN bus 66 such as, for example, the engine 48 and the transmission 50, and to permit parsing, scaling, tag mapping, alarming, data storage, data transmission, or any combination thereof. In several exemplary embodiments, the gateway 56 is programmed to allow sensor data received from the one or more sensors 54 and thus acquired by the gateway 56, and/or data representative of, or based on, the received/acquired sensor data, to be transmitted over the CAN transceiver in J1939 format; in several exemplary embodiments, this data allowed to be transmitted may include, for example, sensor values and/or other metric values. In several exemplary embodiments, the gateway 56 is programmed to allow data from other devices in communication with the CAN bus 66 such as, for example, the engine 48 and/or the transmission 50, to be read and stored on the gateway 56; in several exemplary embodiments, this data allowed to be transmitted can be used to activate alarm(s) and/or conduct post-analysis. In several exemplary embodiments, the gateway 56 is so programmed, in accordance with the foregoing, by storing a plurality of instructions on the computer readable medium 60, which instructions are accessible to, and executable by, the one or more computer processors 58 of the gateway.

In several exemplary embodiments, the hydraulic fracturing pump systems 18, 20, and 22 are in communication with the pump analysis systems 26, 28, and 30, respectively, via respective CAN buses, each of which is substantially identical to the CAN bus 66.

In several exemplary embodiments, each of the hydraulic fracturing pump systems 18, 20, and 22 is substantially identical to the above-described hydraulic fracturing pump system 16 and therefore will not be described in further detail. In several exemplary embodiments, the operation of each of the hydraulic fracturing pump systems 18, 20, and 22 is substantially identical to the above-described operation of the hydraulic fracturing pump system 16 and therefore will not be described in further detail. In several exemplary embodiments, each of the pump analysis systems 26, 28, and 30 is substantially identical to the above-described pump analysis system 24 and therefore will not be described in further detail. In several exemplary embodiments, the operation of each of the pump analysis systems 26, 28, and 30 is substantially identical to the above-described operation of the pump analysis system 24 and therefore will not be described in further detail.

Figure 4:
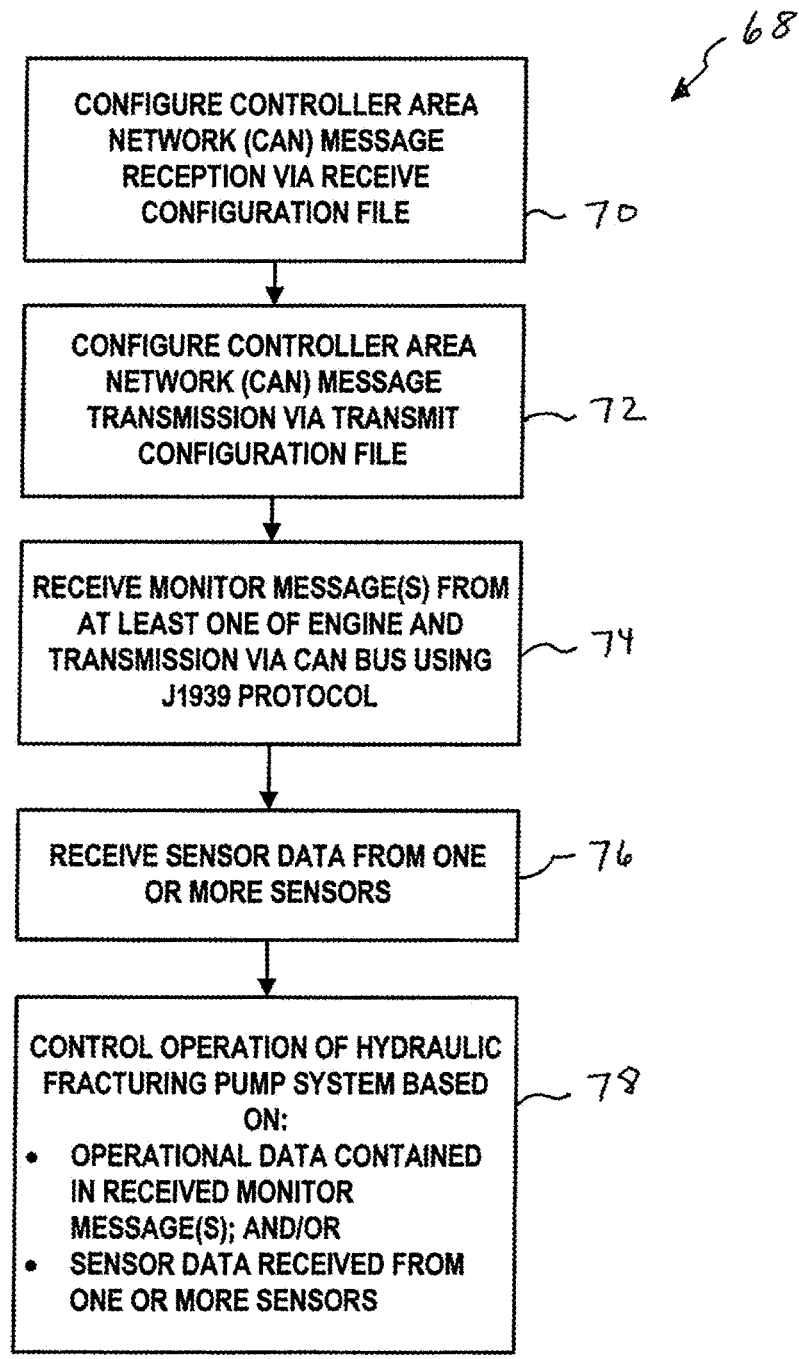
FIG. 4 is a flow chart illustration of a method of controlling the hydraulic fracturing system of FIG. 3, according to an exemplary embodiment.

In an exemplary embodiment, as illustrated in FIG. 4 with continuing reference to FIGS. 1-3, a method of controlling the hydraulic fracturing pump system 16 is generally referred to by the reference numeral 68. The method 68 is executed in whole or in part using the CAN bus 66 and/or the gateway 56 of the pump analysis system 24, and includes step 70 at which controller area network (CAN) message reception is configured via a receive configuration file. In an exemplary embodiment, the receive configuration file is a device configuration file (DCF). In an exemplary embodiment, the receive configuration file is a device configuration file in .dcf file format. In an exemplary embodiment, the receive configuration file is an XML device configuration in .xdc file format. At step 72, CAN message transmission is configured via a transmit configuration file. In an exemplary embodiment, the transmit configuration file is a device configuration file (DCF). In an exemplary embodiment, the transmit configuration file is a device configuration file in .dcf file format. In an exemplary embodiment, the receive configuration file is an XML device configuration in .xdc file format. At step 74, the gateway 56 receives monitor message(s) from at least one of the engine 48 and the transmission 50 via the CAN bus 66 using J1939 protocol. In an exemplary embodiment, the monitor message(s) received at the step 74 include operational data associated with operating parameter(s) of the engine 48 and/or the transmission 50. At step 76, the gateway 56 receives sensor data from the one or more sensors 54, in accordance with the foregoing description of the operation of the system 10. At step 78, the operation of the hydraulic fracturing pump system 16 is controlled based on operational data contained in the monitor message(s) received at the step 74 and/or the sensor data received from the one or more sensors 54 at the step 76.

In an exemplary embodiment, the step 78 includes step 78a, at which the gateway 56 collects, analyzes, conditions, processes, and/or stores the sensor data received from the one or more sensors 54 at the step 76. In several exemplary embodiments, at the step 78a, the gateway 56 uses the sensor data received at the step 76 to monitor the operation of at least the reciprocating pump assembly 52. At step 78b, the gateway 56 collects, analyzes, conditions, processes, and/or stores the monitor message(s) received via the CAN bus 66 at the step 74. In several exemplary embodiments, at the step 78b, the gateway 56 monitors the operation of at least the engine 48 and/or the transmission 50. At step 78c, the sensor data received at the step 76 is transmitted from the gateway 56 to the remote central monitoring system 32 for remote monitoring, in accordance with the foregoing description of the operation of the system 10. At step 78d, the monitor message(s) received at the step 74 and/or operational data associated therewith (e.g., the operational data contained in the monitor message(s) or data representative of, or based on, the received operational data) is transmitted from the gateway 56 to the remote central monitoring system 32, in accordance with the foregoing description of the operation of the system 10.

The step 78 further includes step 78e, at which the gateway 56, the application server 36, the remote user devices 42 and/or 44, or any combination thereof, determine alarm(s) and/or adjustments to the operation of the hydraulic fracturing pump system 16. In several exemplary embodiments, the determinations made at the step 78e are made based on the sensor data received at the step 76 and/or the operational data received at the step 74. For example, the sensor and/or operational data may indicate that: the speed of the engine 48 is too fast or too slow, the pressure upstream and/or downstream of the reciprocating pump assembly 52 is too high or too low, one or more temperatures associated with the pump system 16 are too high, etc. In an exemplary embodiment, the steps 78c and 78d are omitted and only the gateway 56 is used to monitor the hydraulic fracturing pump system 16, determining alarm(s) and/or adjustments to the operation of the hydraulic fracturing pump system 16.

At step 78f, control message(s) are transmitted from the remote control monitoring system 32 to the gateway 56, via the one or more antennas 64. In several exemplary embodiments, the control message(s) transmitted at the step 78f include information on alarms that should be activated at the frac site 12, and/or adjustments to the operation of the hydraulic fracturing pump system 16. At step 78g, alarm(s) are activated at the gateway 56 and/or are transmitted from the gateway 56 to a control van located at the frac site 12, and/or to one or more other locations. At the step 78g, in several exemplary embodiments, the alarm(s) that are activated may be those that are determined at the step 78e and/or those for which information is transmitted at the step 78f. In several exemplary embodiments, the step 78g is omitted. In several exemplary embodiments, the step 78g is omitted if no alarms are determined at the step 78e and/or the message transmitted at the step 78f does not contain alarm information. In several exemplary embodiments, activating alarm(s) at the step 78g controls the operation of the hydraulic fracturing pump system 16 because it causes operators to take action and adjust the operation of the pump system 16 including, in some cases, shutting down the operation of the pump system 16.

The step 78 further includes step 78h, at which control message(s) are transmitted, via the CAN bus 66, from the gateway 56 to at least one of the engine 48 and the transmission 50 to adjust the operation of the hydraulic fracturing pump system 16 based on the sensor data received from the one or more sensors 54 at the step 76 and/or the operational data contained in the monitor message(s) received at the step 74. As a result, the operation of the hydraulic fracturing pump system 16 is controlled at the step 78. In several exemplary embodiments, the control message(s) transmitted at the step 78h contain sensor data received from the one or more sensors 54 at the step 76, and/or data representative of, or based on, the sensor data received from the one or more sensors 54 at the step 76. In several exemplary embodiments, engine controller 80 adjusts the operation of the engine 48, and/or transmission controller 82 adjusts the operation of the transmission 50, based on the sensor data received at the step 54 and transmitted at the step 78h.

In several exemplary embodiments, one or more of the steps 70, 72, 74, and 76 are omitted from the method 68. In several exemplary embodiments, the steps 70, 72, and 74 are omitted from the method 68. In several exemplary embodiments, the steps 78b, 78d, 78f, 78g, and 78h are omitted from the step 78.

In several exemplary embodiments, although the method 68 has been described above in connection with controlling the hydraulic fracturing pump system 16 by employing the pump analysis system 24 and the CAN bus 66, the method 68 may also be executed without employing the CAN bus 66 and thus may omit some steps of the method 68 such as, for example, the steps 70, 72, 74, 78b, 78d, and 78h. In several exemplary embodiments, although the method 68 has been described above in connection with controlling the hydraulic fracturing pump system 16 by employing the pump analysis system 24 and optionally the CAN bus 66, the method 68 may also be executed to control the operation of any one of the hydraulic fracturing pump systems 18, 20, and 22 and thus may employ the corresponding one of the pump analysis systems 26, 28, and 30 operably coupled thereto, as well as optionally a CAN bus that is substantially identical to the CAN bus 66.

Figure 5:
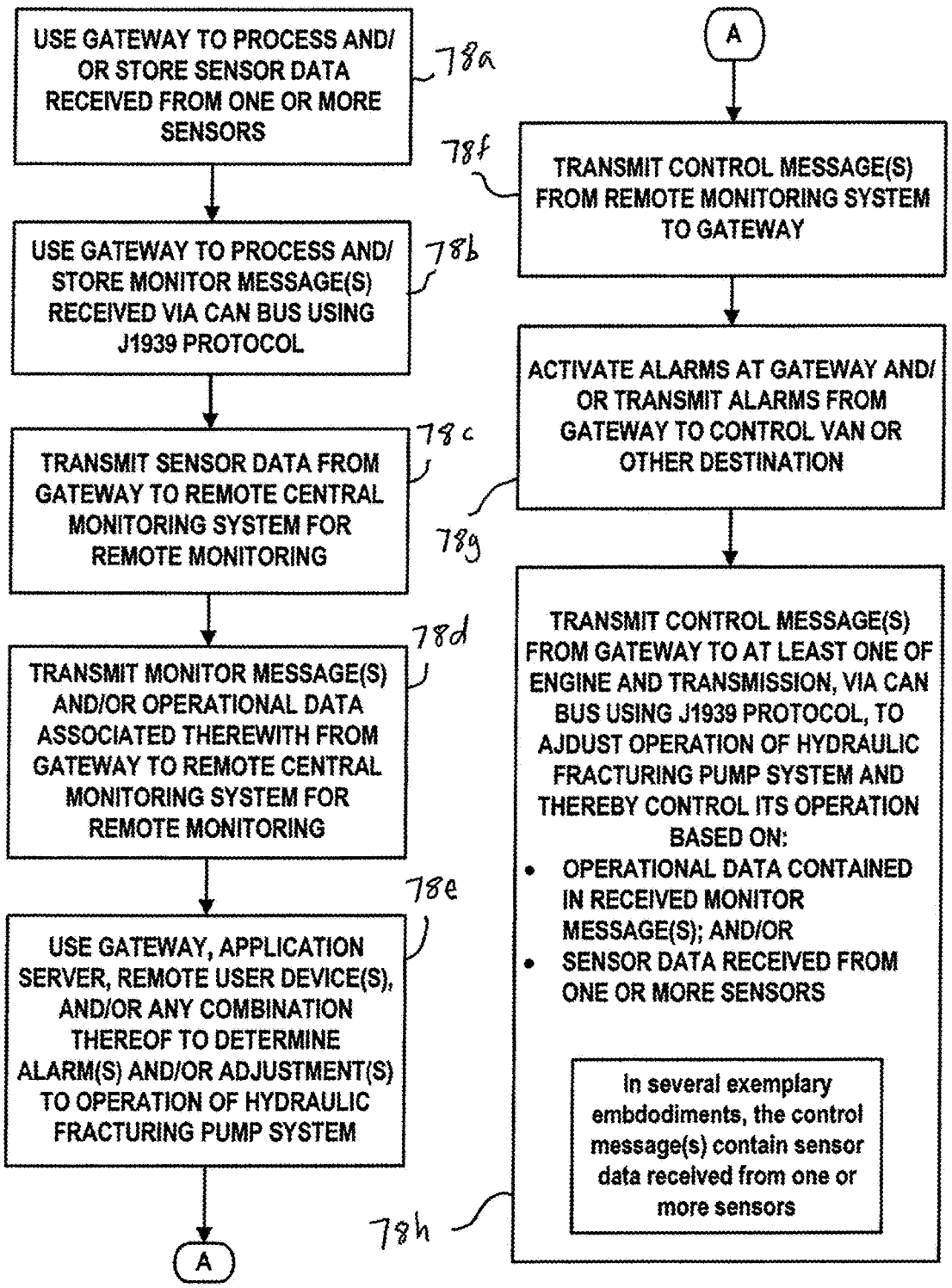
FIG. 5 is a flow chart illustration of a step of the method of FIG. 4, according to an exemplary embodiment.

In several exemplary embodiments, the exemplary embodiment illustrated in FIG. 3, including the hydraulic fracturing pump system 16, the pump analysis system 24, and the CAN bus 66, and the method 68 of FIGS. 4 and 5, provide autonomous operation of the hydraulic fracturing pump system 16 as a standalone unit. In several exemplary embodiments, the exemplary embodiment illustrated in FIG. 3, including the hydraulic fracturing pump system 16, the pump analysis system 24, and the CAN bus 66, and the method 68 of FIGS. 4 and 5, provide autonomous operation of the hydraulic fracturing pump system 16 as a standalone unit, and provide for integration for engine 48 controls through the CAN bus 66 per J1939 protocol. In several exemplary embodiments, the exemplary embodiment illustrated in FIG. 3, including the hydraulic fracturing pump system 16, the pump analysis system 24, and the CAN bus 66, and the method 68 of FIGS. 4 and 5, provide autonomous operation of the hydraulic fracturing pump system 16 as a standalone unit, with the steps 78c, 78d, and 78f being omitted, and at the step 78e only the gateway 56 determining adjustments to the operation of the hydraulic fracturing pump system 16.

Figure 6:
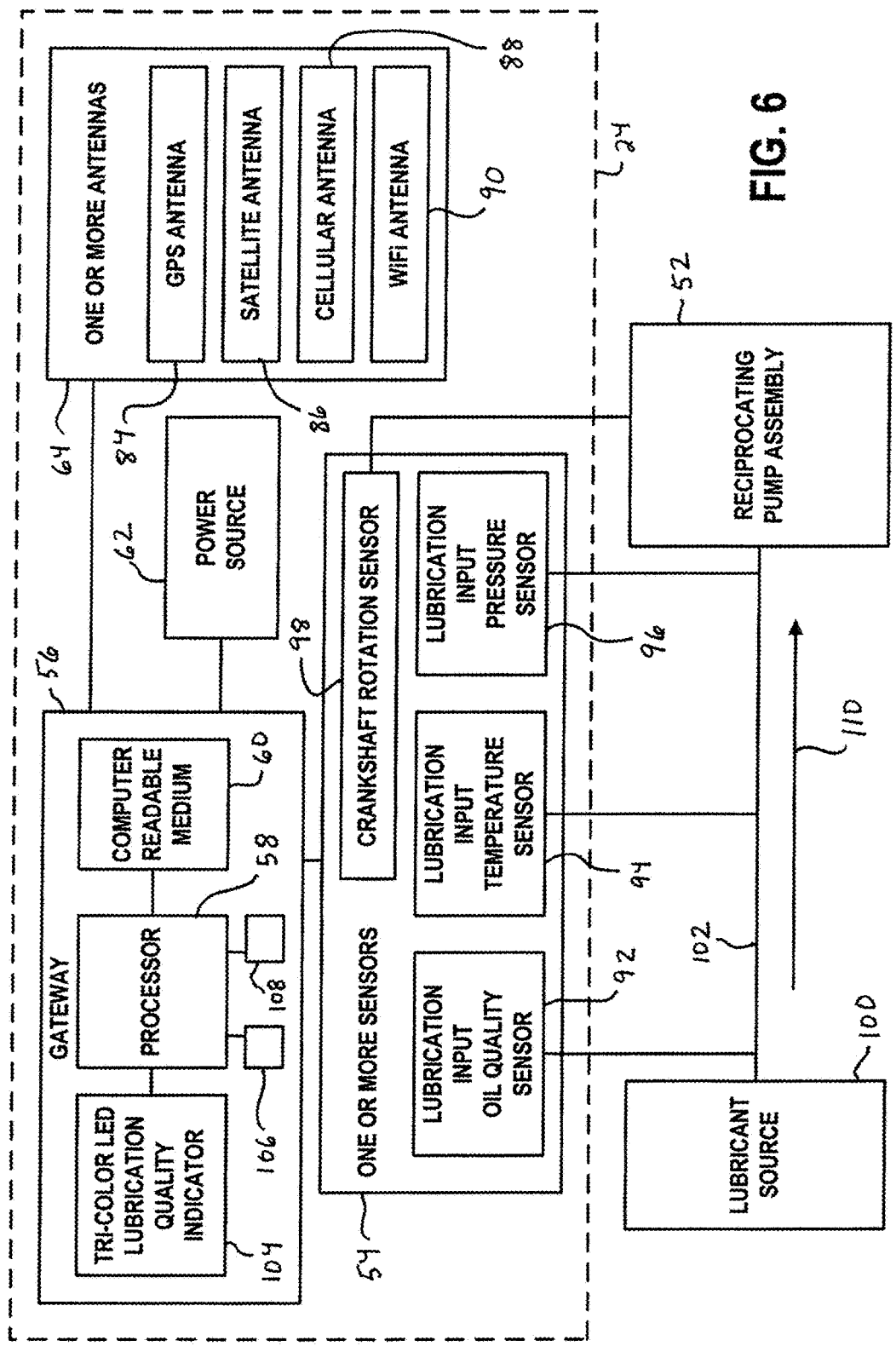
FIG. 6 is a diagrammatic illustration of a portion of one of the hydraulic fracturing pump systems of FIG. 1, and the corresponding one of the pump analysis systems of Figure operably coupled to the portion, according to an exemplary embodiment.

In an exemplary embodiment, as illustrated in FIG. 6 with continuing reference to FIGS. 1-5, the one or more antennas 64 include a GPS antenna 84, a satellite antenna 86, a cellular antenna 88, and a Wi-Fi antenna 90. The one or more sensors 54 include a lubrication input oil quality sensor 92, a lubrication input temperature sensor 94, a lubrication input pressure sensor 96, and a crankshaft position sensor 98. A lubricant source 100 is in fluid communication with the reciprocating pump assembly 52 via a lubrication input fluid line 102. In an exemplary embodiment, the lubricant source 100 is an oil tank. Each of the lubrication input oil quality sensor 92, the lubrication input temperature sensor 94, and the lubrication input pressure sensor 96 is operably coupled to the lubrication input fluid line 102. The crankshaft position sensor 98 is operably coupled to the reciprocating pump assembly 52.

In an exemplary embodiment, the lubrication input pressure sensor 96 includes a pressure transducer. In an exemplary embodiment, the crankshaft position sensor 98 is an inductive sensor. In an exemplary embodiment, the lubrication input oil quality sensor 92 is a dielectric sensor. In an exemplary embodiment, the lubrication input oil quality sensor 92 is an inductive/magnetic sensor. In several exemplary embodiments, two or more of the lubrication input oil quality sensor 92, the lubrication input temperature sensor 94, and the lubrication input pressure sensor 96 are combined in whole or in part.

The gateway 56 includes an indicator 104 configured to visually indicate or show the oil quality of the lubricant adapted to flow through the fluid line 102 and into the reciprocating pump assembly 52. In an exemplary embodiment, the indicator 104 is a multi-color indicator, with a plurality (at least two) color states, with the different color states indicating different oil qualities, respectively. In an exemplary embodiment, as show in FIG. 6, the indicator 54 is a tri-color LED indicator having three color states. The gateway 56 further includes a temperature indicator 106 and a pressure indicator 108 to visually indicate or show the temperature and the pressure, respectively, of the lubricant adapted to flow through the fluid line 102. In several exemplary embodiments, each of the indicators 106 and 108 is either a single-state LED indicator or a multi-state LED indicator.

In operation, in an exemplary embodiment, as illustrated in FIG. 6 with continuing reference to FIGS. 1-5, the hydraulic fracturing pump system 16 operates in accordance with the foregoing; consequently, the reciprocating pump assembly 52 operates in accordance with the foregoing. During the operation of the reciprocating pump assembly 52, lubricant flows, via the lubrication input fluid line 102, from the lubricant source 100 to the reciprocating pump assembly 52 for distribution to different systems/components therein. This lubricant flow is indicated by arrow 110 in FIG. 6.

During the operation of the reciprocating pump assembly 52, in an exemplary embodiment, the lubrication input oil quality sensor 92 measures the quality of the lubricant flowing through the fluid line 102 and into the reciprocating pump assembly 52. In an exemplary embodiment, to measure the quality of the lubricant, the lubrication input oil quality sensor 92 measures the contaminant level in the lubricant flowing through the line 102. In an exemplary embodiment, to measure the quality of the lubricant, the lubrication input oil quality sensor 92 measures the amount of contaminants within the lubricant as it flows through the flow line 102. In an exemplary embodiment, the gateway 56 receives from the lubrication oil input quality sensor 92 sensor data associated with the quality of the lubricant in the fluid line 102. In an exemplary embodiment, the lubrication input oil quality sensor 92 or the gateway 56 determines the lubricant quality or condition, degradation, and/or any combination thereof. In an exemplary embodiment, the lubrication input oil quality sensor 92 or the gateway 56 determines the lubricant quality or condition, degradation, and/or any combination thereof, based on historical values. In an exemplary embodiment, the lubrication input oil quality sensor 92 or the gateway 56 determines the lubricant quality or condition, degradation, and/or any combination thereof, based on historical values (ISO standard based).

In an exemplary embodiment, the lubrication input oil quality sensor 92 or the gateway 56 determines the lubricant quality or condition, degradation, and/or any combination thereof, and based on this determination the gateway 56 causes the indicator 104 to indicate the quality of the lubricant. In an exemplary embodiment, as shown in FIG. 6, the indicator 104 is a tri-color LED indicator having three color states; in several exemplary embodiments, the indicator 104 has a green color state when the lubricant quality is good, an amber color state when the lubricant quality is fair, and a red color state when lubricant quality is poor. As a result, the quality of the lubricant is able to be monitored by visual inspection of the indicator 104 of the gateway 56.

The lubrication input temperature sensor 94 measures the temperature of the lubricant flowing through the fluid line 102 and into the reciprocating pump assembly 52. In an exemplary embodiment, the gateway 56 receives from the lubrication input temperature sensor 94 sensor data associated with the temperature of the lubricant in the fluid line 102. The sensor 94 or the gateway 56 determines whether the lubricant temperature is too high or too low. In an exemplary embodiment, if the temperature is too high, the gateway 56 causes the indicator 106 to indicate that the temperature is too high by, for example, activating a first predetermined color state of the indicator 106. In an exemplary embodiment, if the temperature is too low, the gateway 56 causes the indicator 106 to indicate that the temperature is too low by, for example, activating a second predetermined color state of the indicator 106, the second predetermined color state being different from the first predetermined color state. In an exemplary embodiment, if the lubricant temperature is too high or too low, the gateway 56 causes the indicator 106 to activate a predetermined color state. As a result of any of the foregoing exemplary embodiments, the existence of an undesirable temperature condition at the reciprocating pump assembly 52 is able to be detected by visual inspection of the indicator 106 of the gateway 56. In an exemplary embodiment, the lubrication input temperature sensor 94 measures the temperature of the lubricant on the high pressure side, at the output of the lubricant source 100 which, in several exemplary embodiments, is the output from an oil tank drain. In several exemplary embodiments, the lubrication input temperature sensor 94 includes a plurality of sensors, which measure: (a) the temperature of the lubricant on the high pressure side, at the output of the lubricant source 100; (b) the temperature of the lubricant on the low pressure side, at the output from a heat exchanger; (c) the temperature of the lubricant at the output of a crankshaft drain; and (d) the temperature of the lubricant at the output of a gearbox drain.

The lubrication input pressure sensor 96 measures the pressure of the lubricant flowing through the fluid line 102 and into the reciprocating pump assembly 52. In an exemplary embodiment, the gateway 56 receives from the lubrication input pressure sensor 96 sensor data associated with the pressure of the lubricant in the fluid line 102. The sensor 96 or the gateway 56 determines whether the lubricant pressure is too high or too low. In an exemplary embodiment, if the pressure is too high, the gateway 56 causes the indicator 108 to indicate that the pressure is too high by, for example, activating a first predetermined color state of the indicator 108. In an exemplary embodiment, if the pressure is too low, the gateway 56 causes the indicator 108 to indicate that the pressure is too low by, for example, activating a second predetermined color state of the indicator 108, the second predetermined color state being different from the first predetermined color state. In an exemplary embodiment, if the lubricant pressure is too high or too low, the gateway 56 causes the indicator 108 to activate a predetermined color state. As a result of any of the foregoing exemplary embodiments, the existence of an undesirable pressure conditions at the reciprocating pump assembly 52 is able to be detected by visual inspection of the indicator 108 of the gateway 56. In an exemplary embodiment, the lubrication input pressure sensor 96 includes at least two input pressure sensors, with one pressure sensor measuring the lubricant pressure at the low pressure side and the other pressure sensor measuring the lubricant pressure at the high pressure side.

The crankshaft rotation sensor 98 counts the number of times the crankshaft of the reciprocating pump assembly 52 rotates. In an exemplary embodiment, the gateway 56 receives from the crankshaft rotation sensor 98 sensor data associated with the number of times the crankshaft of the reciprocating pump assembly 52 rotates. In several exemplary embodiments, the crankshaft rotation sensor 98 counts the number of times the crankshaft of the reciprocating pump assembly 52 rotates, and the crankshaft rotation sensor 58 or the gateway 56 compares the count to time to calculate the rotation speed of the crankshaft 25. In several exemplary embodiments, the crankshaft rotation sensor 98 or the gateway 56 senses when the reciprocating pump assembly 52 is active, as well as the amount of time that the reciprocating pump assembly 52 is active. In several exemplary embodiments, the crankshaft rotation sensor 98 or the gateway 56 is used to determine the overall total amount of time that the reciprocating pump assembly 52 has operated during its operational life.

During operation, in several exemplary embodiments, via the one or more antennas 64, the gateway 56 sends the sensor data as received, the sensor data as processed, the determined one or more operating parameters, or any combination thereof, to the remote central monitoring system 32. The application server 36 receives the sensor data as received, the sensor data as conditioned or otherwise processed, the determined one or more operating parameters, or any combination thereof, via the communication server 34, and stores this information in whole or in part on the computer readable medium 40 including, in several exemplary embodiments, in the database 41. In several exemplary embodiments, the gateway 56 sends data to the application server 36 via the satellite antenna 86. In several exemplary embodiments, the gateway 56 sends data to the application server 36 via one or more of the satellite antenna 86, the cellular antenna 88, and the Wi-Fi antenna 90.

During operation, in several exemplary embodiments, the gateway 56 or the application server 36 samples the crankshaft rotation sensor 98 to determine when the reciprocating pump assembly 52 is active. In an exemplary embodiment, the gateway 56 or the application server 36 flags an event if the reciprocating pump assembly 52 changes from an inactive state to an activate state, and vice versa. In an exemplary embodiment, the gateway 56 or the application server 36 flags an event if the lubricant temperature exceeds a set threshold. In an exemplary embodiment, the gateway 56 or the application server 36 flags an event if the lubricant temperature does not reach a set threshold. In an exemplary embodiment, the gateway 56 or the application server 36 flags an event if the lubricant pressure exceeds a set threshold. In an exemplary embodiment, the gateway 56 or the application server 36 flags an event if the lubricant pressure does not reach a set threshold. In an exemplary embodiment, the gateway 56 or the application server 36 flags an event when the quality or condition of the lubricant in the fluid line 102 changes from, for example, good to fair, fair to poor, etc.

As noted above, in several exemplary embodiments, the gateway 56 sends data to the application server 36 via one or more of the satellite antenna 86, the cellular antenna 88, and the Wi-Fi antenna 90. In several exemplary embodiments, in addition to the application server 36, the gateway 56 is configured to transmit data to another computer device via one or more of the satellite antenna 86, the cellular antenna 88, and the Wi-Fi antenna 90, or via a hardwired connection. In several exemplary embodiments, the gateway 56 sends data immediately to a computing device located at the frac site 12 via either a hardwired connection or the one or more antennas 64, as well as immediately to the application server 36 via the one or more of the satellite antenna 86, the cellular antenna 88, and the Wi-Fi antenna 90.

During operation, in several exemplary embodiments, the gateway 56 stores sensor data, and/or data based thereupon, on the non-transitory computer readable medium 60. In several exemplary embodiments, the gateway 56 so stores the data for holding the data when communication is unavailable, when transmitting blocks of data to the application server 36 at defined time intervals, when the application server 36 requests the data from the gateway 56, or any combination thereof.

During operation, in several exemplary embodiments, the gateway 56 includes a GPS receiver that receives GPS location coordinates via the GPS antenna 84; the gateway 56 interprets the GPS location coordinates and sends location information identifying the location of the hydraulic fracturing pump system 16, or at least the location of the frac site 12, to the application server 36. In an exemplary embodiment, the gateway 56 sends the location information to the application server 36 via the satellite antenna 86. In several exemplary embodiments, the gateway 56 sends the location information to the application server 36 via one or more of the satellite antenna 86, the cellular antenna 88, and the Wi-Fi antenna 90.

In several exemplary embodiments, although FIG. 6 illustrates an exemplary embodiment of the pump analysis system 24, each of the pump analysis systems 26, 28, and 30 may be substantially identical to the above-described pump analysis system 24 as illustrated in FIG. 6. In several exemplary embodiments, the operation of each of the pump analysis systems 26, 28, and 30 is substantially identical to the above-described operation of the pump analysis system 24 as illustrated in FIG. 6.

In several exemplary embodiments, at least one of the crankshaft rotation sensor 98, the gateway 56, and the application server 36 determines the revolutions per minute (RPM) of the crankshaft 25. In several exemplary embodiments, at least one of the crankshaft rotation sensor 98, the gateway 56, and the application server 36 establishes a relationship between lubricant pressure and pump RPM, a relationship between lubricant temperature and pump RPM, a relationship between pump RPM and lubricant pressure and temperature, or any combination thereof.

Figure 7:
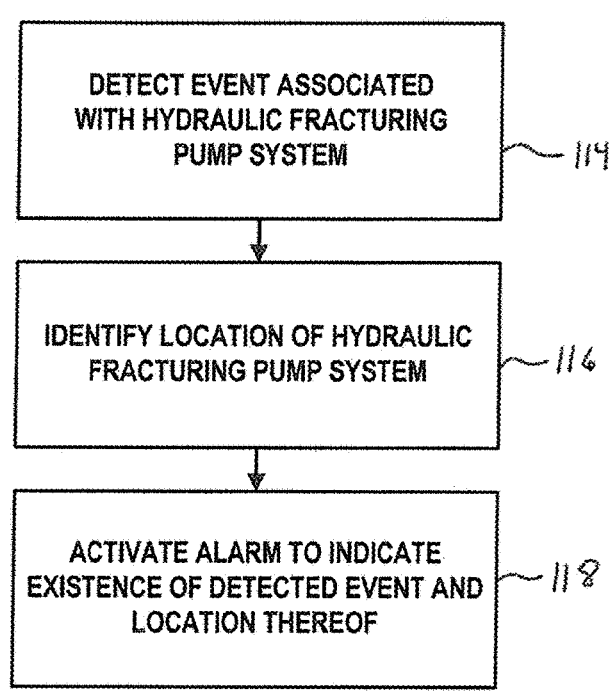
FIG. 7 is a flow chart illustration of a method employing the pump analysis system of FIG. 6, according to an exemplary embodiment.

In an exemplary embodiment, as illustrated in FIG. 7 with continuing reference to FIGS. 1-6, a method is generally referred to by the reference numeral 112 and includes detecting an event associated with the hydraulic fracturing pump system 16 at step 114, identifying the location of the hydraulic fracturing pump system 16 at step 116, and at step 118 activating an alarm to indicate the existence of the event and the location thereof.

In an exemplary embodiment, at the step 114, the gateway 56 or the application server 36 detects the event associated with the hydraulic fracturing pump system 16. In several exemplary embodiments, the event detected at the step 114 includes one or more of the following: the reciprocating pump assembly 52 has become active; the reciprocating pump assembly 52 has become inactive; the operational life of the reciprocating pump assembly 52 has reached or exceeded a set threshold and part(s) of the reciprocating pump assembly 52 should be inspected and/or replaced; the lubricant temperature in the fluid line 102 has exceeded a set threshold; the lubricant temperature in the fluid line 102 has not reached a set threshold; the lubricant pressure in the fluid line 102 has exceeded a set threshold; the lubricant pressure in the fluid line 102 has not reached a set threshold; the quality or condition of the lubricant in the fluid line 102 has changed from good to fair; and the quality or condition of the lubricant in the fluid line 102 has changed from fair to poor. In several exemplary embodiments, the step 114 includes: measuring, using the one or more sensors 54, one or more physical properties associated with the reciprocating pump assembly 52; sending sensor data associated with the one or more physical properties from the one or more sensors 54 to the gateway 56, optionally using the one or more processors 58 of the gateway 56 to analyze, condition, or otherwise process the sensor data to determine one or more operating parameters of the reciprocating pump assembly 52; optionally sending the sensor data as received, the sensor data as processed, the determined one or more operating parameters, or any combination thereof, from the gateway 56 to the application server 36; using the gateway 56 and/or the application server 36 to detect the event based on the sensor data as processed, the determined one or more operating parameters, or any combination thereof in several exemplary embodiments, the gateway 56 or the application server 36 compares the one or more operating parameters with one or more set thresholds.

In an exemplary embodiment, at the step 116, the GPS receiver of the gateway 56 receives, via the GPS antenna 84, the GPS location coordinates of the hydraulic fracturing pump system 16. The gateway 56 interprets the GPS location coordinates to determine the location of the hydraulic fracturing pump system 16, or at least the frac site 12. In an exemplary embodiment, at the step 116, the gateway 56 sends location information identifying the location of the hydraulic fracturing pump system 16, or at least the location of the frac site 12, to the application server 36. In an exemplary embodiment, the gateway 56 sends the location information to the application server 36 via the satellite antenna 86. In several exemplary embodiments, the gateway 56 sends the location information to the application server 36 via one or more of the satellite antenna 86, the cellular antenna 88, and the Wi-Fi antenna 90.

In an exemplary embodiment, the step 118 includes graphically depicting an alarm on the remote user devices 42 and/or 44, the alarm indicating the existence of the event and the location of the hydraulic fracturing pump system 16. As a result, the users of the remote user devices 42 and/or 44 are alerted to the existence of the event and the location thereof. In an exemplary embodiment, the step 118 includes graphically depicting an alarm on another output device that is in communication with the gateway 56 and/or the application server 36, such as a display screen in a control van located at the frac site 12. The alarm indicates the existence of the event and the location thereof. As a result, an operator in the control van is alerted to the existence of the event and the location thereof. In an exemplary embodiment, the step 118 includes the gateway 56, the application server 36, the remote user device 42, or the remote user device 44 sending one or more email messages, one or more text messages, one or more other messages, or any combination thereof; the one or messages indicate the existence of the event and the location thereof so that recipients of the messages are alerted to the existence of the event and the location thereof. In an exemplary embodiment, the step 118 includes the gateway 56, the application server 36, the remote user device 42, or the remote user device 44 flagging the event for immediate notification, and/or flagging the event and storing the flagging for notification at a later time such as, for example, when a report is generated at, for example, the conclusion of a predetermined time interval (1 day, 1 week, 1 month, etc.), with the flagging being the activation of an alarm. In several exemplary embodiments, the step 118 includes one or more of the following: showing the event of a change in oil quality of the lubricant using the indicator 104, the indicator 104 changing from one color state to another color state that is different from the one color state; showing the event of the lubricant temperature being either too high or too low using the temperature indicator 106; and showing the event of the lubricant pressure being either too high or too low using the pressure indicator 108.

In several exemplary embodiments, by providing the location of the hydraulic fracturing pump system 16, the step 118 enables the pump system 16 to be inspected at the frac site 12 to determine if one or more components need to be replaced (such as one or more valves, fluid lines, etc.), if the operation of the hydraulic fracturing pump system 16 needs to be adjusted or shut down, or if some other corrective action is required such as, for example, replacement of the lubricant.

In several exemplary embodiments, the step 116 is omitted from the method 112, and the step 118 does not include activating an alarm to alert the location of the hydraulic fracturing pump system 16; the step 118 continues to include activating the alarm to alert existence of the event detected at the step 114.

In several exemplary embodiments, although the method 112 has been described above in connection with the exemplary embodiment of the pump analysis system 24 illustrated in FIG. 6, the method 112 may also be executed using one of the pump analysis systems 26, 28, and 30, which pump analysis system may be substantially identical to the exemplary embodiment of the pump analysis system 24 illustrated in FIG. 6.

In several exemplary embodiments, the operation of the pump analysis system 24 of FIG. 6, or the execution of the method 112 of FIG. 7, determines real-time lubrication conditions for the purpose of alleviating any failures in the hydraulic fracturing pump system 16 resulting from lubrication issues.

In several exemplary embodiments, during the operation of the pump analysis system 24 of FIG. 6, or during the execution of the method 112 of FIG. 7, the remote user device 42 or 44, and/or another computing device located at, for example, in the control van at the frac site 12, displays or otherwise includes a web interface; in several exemplary embodiments, the web interface has one or more of the following functions: view GPS location coordinates of hydraulic fracturing pump system 16; view last connection update to the application server 36; view lubricant pressure value as measured by lubrication input pressure sensor 96; view lubricant temperature value as measured by lubrication input temperature sensor 94; view oil condition as measured by the lubrication input oil quality sensor 92; view sensor trends over one or more time intervals (e.g., 3-, 6-, 9-, and 12-month intervals); view pump hours, i.e., the number of hours that the hydraulic fracturing pump system 16 has operated over its life (as determined based on measurements by the crankshaft rotation sensor 98); set sensor threshold alarms; view information on the power source 62 (e.g., battery voltage); view satellite communication signal strengths (for satellite communication via the satellite antenna 86); view cellular signal strengths (for cellular communication via the cellular antenna 88); view connection status to the application server 36; view LAN, Wi-Fi, and cellular network and download usage trends on an interval (e.g., per day) and illustrated for a selected time period (e.g., a selected month); download stored sensor values to .csv file; and view equipment events.

In several exemplary embodiments, the system 10 monitors individual frac pumps (such as the hydraulic fracturing pump systems 16, 18, 20, and 22) during field operation, which monitoring includes the collection of runtime data. In several exemplary embodiments, the system 10 enables the detection and prediction of pump failures and malfunctions, greatly increasing operation uptime and avoiding pump downtime. In several exemplary embodiments, the system 10 allows centralized monitoring and data analysis of field-deployed frac pumps, such as the hydraulic fracturing pump systems 16, 18, 20, and 22. In several exemplary embodiments, the monitoring portion of the system 10 includes the monitoring of alarms and events, current pump locations via GPS, current sensor values, along with other relevant pump data points. In several exemplary embodiments, the analysis portion of the system 10 includes pump operation data points, which enable predictive event algorithms, failure analysis, and other types of analysis.

Figure 8:
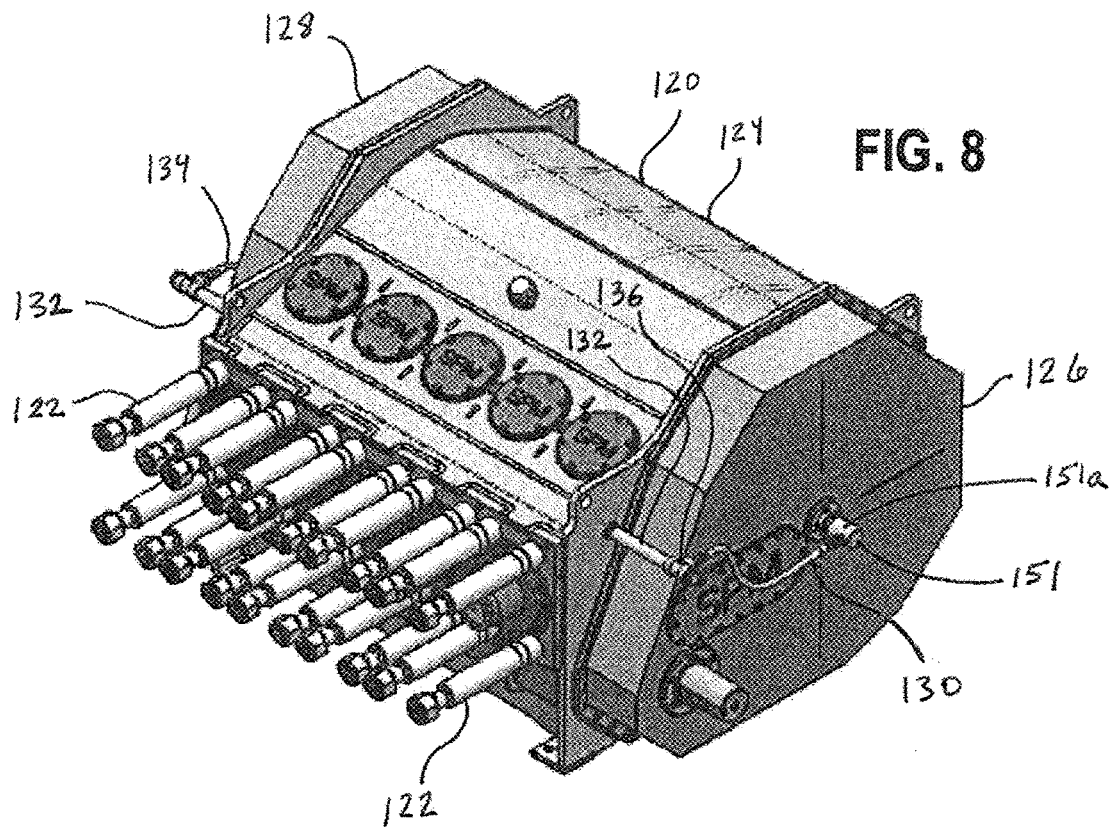
FIG. 8 is a perspective view of a power end of a reciprocating pump assembly of one of the hydraulic fracturing pump systems of FIG. 1, according to an exemplary embodiment.

In an exemplary embodiment, as illustrated in FIG. 8 with continuing reference to FIGS. 1-7, the reciprocating pump assembly 52 includes a power end 120. Stay rods 122 extend between the power end 120 and a fluid end (not shown) of the reciprocating pump assembly 52. The power end 120 includes a housing 124, in which the crankshaft (not shown) is housed; as described above, the transmission 50 is operably coupled to the reciprocating pump assembly 52 via the crankshaft, and the engine 48 is adapted to rotate or drive the crankshaft via the transmission 50, thereby driving the reciprocating pump assembly 52. Gear covers 126 and 128 are connected to opposing sides, respectively, of the housing 124. The power end 120 further includes a fluid line 130 configured to convey lubricant into the gear cover 126, a fluid line 132 configured to convey lubricant to pistons (not shown) enclosed by the housing 124, a fluid line 134 in fluid communication with the fluid line 132 and configured to convey lubricant into the gear cover 128, and a fitting 136 connected to the fluid lines 130 and 132. The fluid line 102 (not shown in FIG. 8) is configured to be connected to the fitting 136 so that the fluid line 102 is in fluid communication with each of the fluid lines 130, 132, and 134.

Figure 9A:
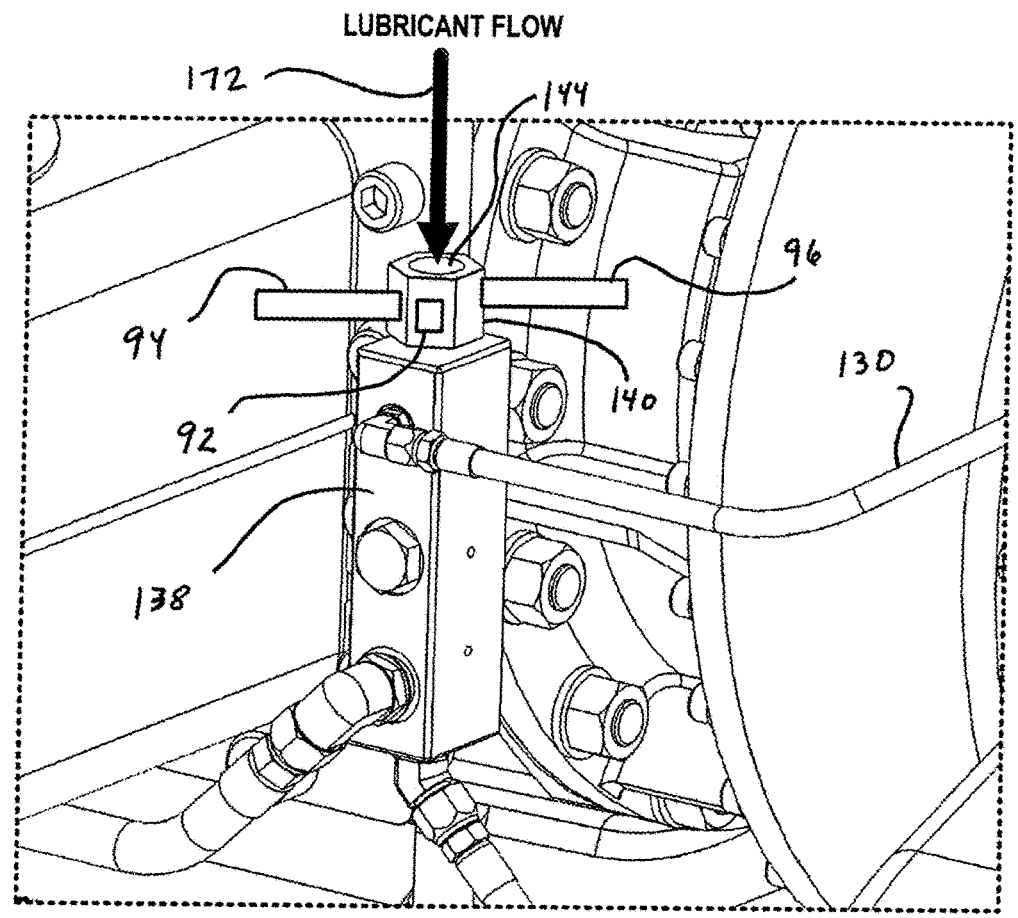
FIG. 9A is a portion of a power end of a reciprocating pump assembly of one of the hydraulic fracturing pump systems of FIG. 1, according to an exemplary embodiment.
Figure 9B:
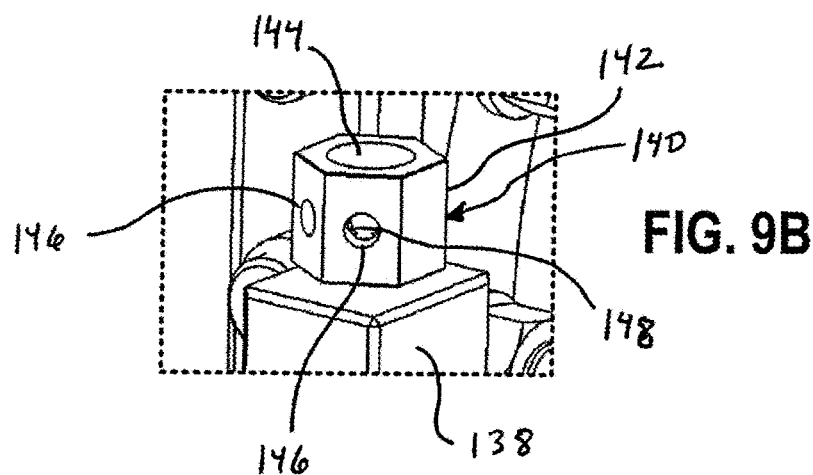
FIG. 9B is an enlarged view of a portion of FIG. 9A, but with components omitted for clarity.

In an exemplary embodiment, as illustrated in FIGS. 9A and 9B within continuing reference to FIGS. 1-8, the fitting 136 is omitted in favor of a distribution block 138, with which the fluid lines 130, 132, and 134 are in fluid communication (the gear cover 126 is omitted from view in FIGS. 9A and 9B, and the gearbox of the exemplary embodiment illustrated in FIGS. 9A and 9B is different from the gearbox of the exemplary embodiment illustrated in FIG. 8). A sensor connector 140 is connected to the distribution block 138 and includes a body 142, the body 142 defining a longitudinally-extending flow passage 144. The sensor connector 140 is in fluid communication with the distribution block 138. The fluid line 102 (shown in FIG. 6) is in fluid communication with sensor connector 140 and thus with the distribution block 138 and the fluid lines 130, 132, and 134. A plurality of radially-extending openings 146 are formed in the body 142 of the sensor connector 140 so that the openings 146 are in fluid communication with the longitudinally-extending flow passage 144. In an exemplary embodiment, the plurality of openings 146 includes at least three openings 146, two of which are shown in FIG. 9B. The lubrication input oil quality sensor 92, the lubrication input temperature sensor 94, and the lubrication input pressure sensor 96 are connected to the body 142 via respective ones of the openings 146.

In several exemplary embodiments, the body 142 includes an external threaded connection (not shown), which is threadably engaged with an internal threaded connection (not shown) formed in the distribution block 138, thereby connecting the sensor connector 140 to the distribution block 138. In several exemplary embodiments, each of the sensors 92, 94, and 96 includes an external threaded connection (not shown), which is threadably engaged with respective internal threaded connections 148 formed in the body 142 and circumscribing the openings 146, thereby connecting the sensors 92, 94, and 96 to the sensor connector 140. In several exemplary embodiments, the body 142 of the sensor connector 140 is, includes, or is part of, a hexagonal lube fitting. In several exemplary embodiments, two or more of the lubrication input oil quality sensor 92, the lubrication input temperature sensor 94, and the lubrication input pressure sensor 96 illustrated in FIG. 9A are combined in whole or in part.

In an exemplary embodiment, referring back to FIG. 8 with continuing reference to FIGS. 1-7, 9A, and 9B, the power end 120 of the reciprocating pump assembly 52 further includes a rotary union 151, which is operably coupled to the crankshaft of the power end 120 on the outside of the gear cover 126. The rotary union 151 includes a housing 151a, to which the fluid line 130 is connected.

Figure 10:
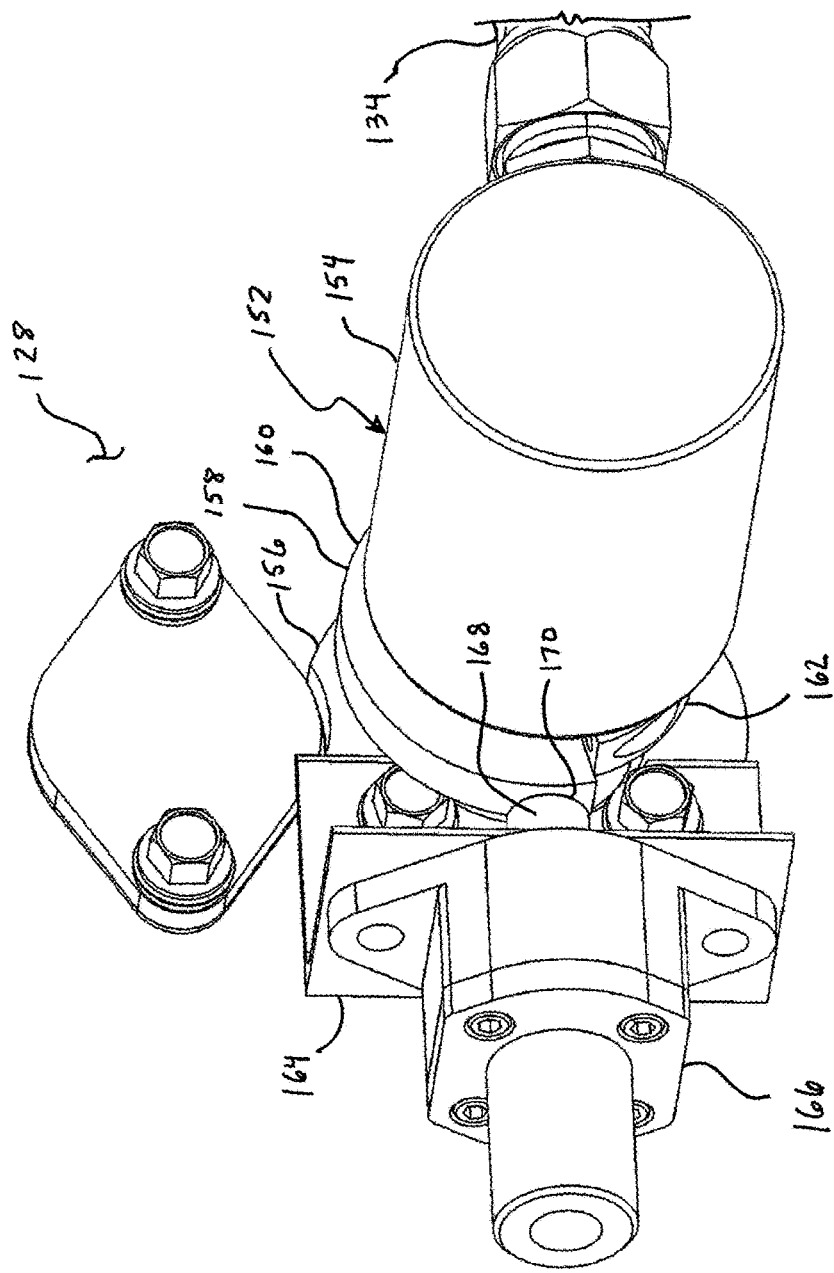
FIG. 10 is a perspective view of another portion of a power end of a reciprocating pump assembly of one of the hydraulic fracturing pump systems of FIG. 1, according to an exemplary embodiment.
Figure 11:
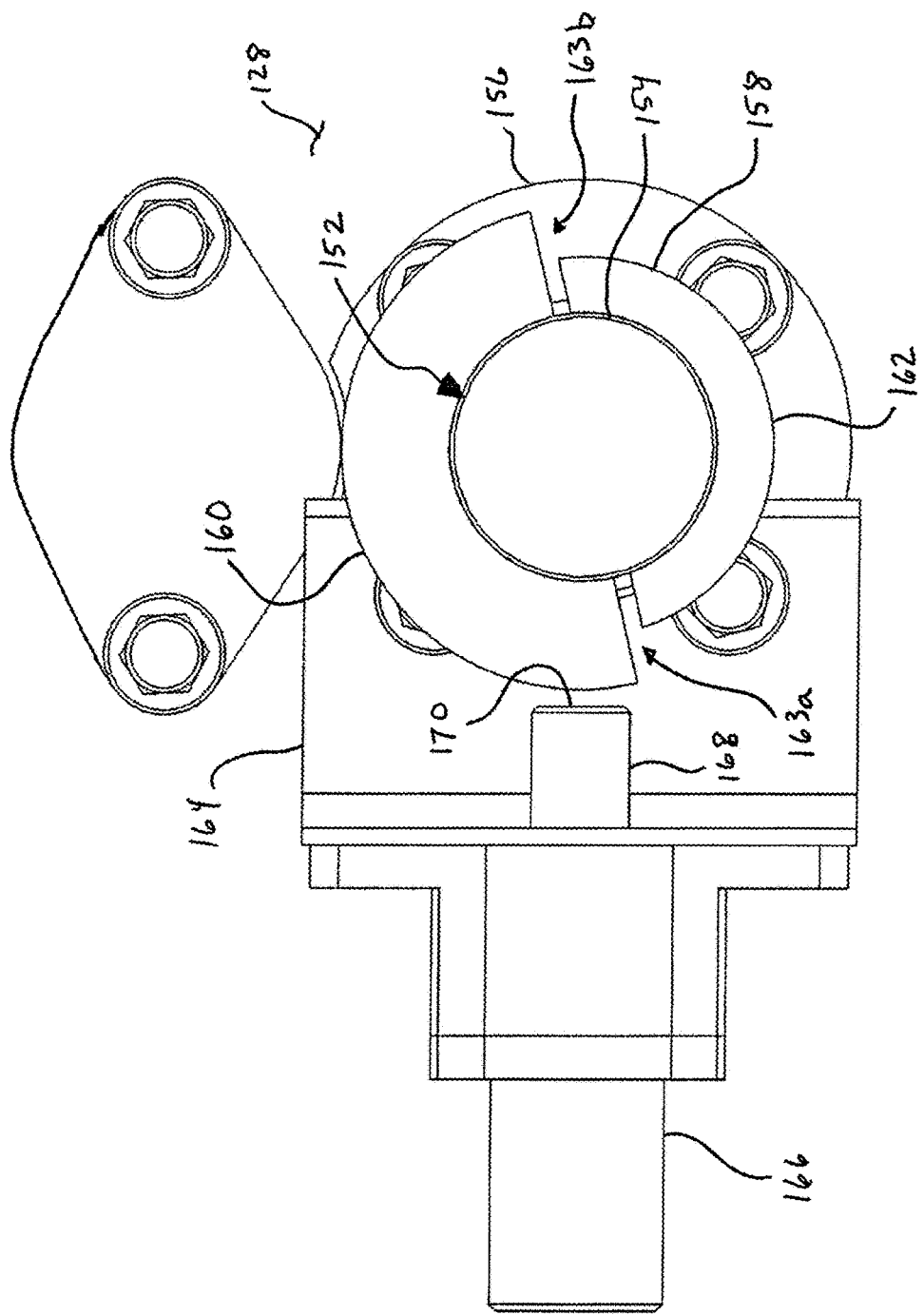
FIG. 11 is an elevational view of the portion of FIG. 10, according to an exemplary embodiment.

In an exemplary embodiment, as illustrated in FIGS. 10 and 11 with continuing reference to FIGS. 1-9B, a rotary union 152 is operably coupled the crankshaft of the power end 120 on the outside of the gear cover 128. The rotary union 152 opposes the rotary union 151. The rotary union 152 includes a housing 154 and a shaft (not shown) disposed therein, which shaft is adapted to rotate along with the crankshaft of the power end 120; in an exemplary embodiment, the shaft is adapted to rotate along with the crankshaft of the power end 120 at the same rotational speed as the crankshaft. The fluid line 134 is connected to the housing 154 of the rotary union 152. The fluid line 134 is shown in FIG. 10, but is omitted from FIG. 11. A seal housing 156 is connected to the gear cover 128. An element, such as a proximity sensor pick-up collar 158, is operably coupled to the rotary union 152 so that the proximity sensor pick-up collar 158 is adapted to rotate along with the shaft of the rotary union 152 and thus along with the crankshaft of the power end 120. The proximity sensor pick-up collar 158 includes arcuate sections 160 and 162. The outer diameter of the arcuate section 160 is greater than the outer diameter of the arcuate section 162, although the respective inner diameters of the arcuate sections 160 and 162 are substantially equal for operably coupling to the rotary union 152. The difference between the respective outer diameters of the arcuate sections 160 and 162 defines outer-diameter transition regions 163a and 163b, which are circumferentially spaced by about 180 degrees. A mounting bracket 164 is connected to the seal housing 156. The crankshaft rotation sensor 98 is connected to the mounting bracket 164. The crankshaft rotation sensor 98 includes a sensor housing 166 and a proximity sensor 168 housed within the sensor housing 166. The sensor housing 166 is connected to the mounting bracket 164 to connect the crankshaft rotation sensor 98 to the gear cover 128. A portion of the proximity sensor 168 extends out of the sensor housing 166 so that a distal end 170 of the proximity sensor is proximate the proximity sensor pick-up collar 158. In an exemplary embodiment, the proximity sensor 168 is an inductive sensor.

During the operation of the reciprocating pump assembly 52, in an exemplary embodiment, with continuing reference to FIGS. 8-11 as well as to FIGS. 1-9B, lubricant flows through the fluid line 102 (shown in FIG. 6) and through the sensor connector 140, as indicated by an arrow 172 in FIG. 9A. The lubricant then flows into the distribution block 138, and through at least the fluid lines 130, 132, and 134 to lubricate at least the power end 120 of the reciprocating pump assembly 52. During this lubricating operation, the pump analysis system 24 operates in accordance with the foregoing. Due to their respective connections with sensor connector 140, the sensors 92, 94, and 96 measure the quality, temperature, and pressure, respectively, of the lubricant in the fluid line 102, in accordance with the foregoing.

During the operation of the reciprocating pump assembly 52, in an exemplary embodiment, the crankshaft rotation sensor 98 counts the number of times the crankshaft of the reciprocating pump assembly 52 rotates. More particularly, the proximity sensor pick-up collar 158 rotates along with the crankshaft of the power end 120, and the proximity sensor 168 detects each time the outer-diameter transition regions 163a and 163b rotate past the distal end 170 of the proximity sensor 168. In an exemplary embodiment, the proximity sensor pick-up collar 158 rotates along with the crankshaft of the power end 120 so that the collar 158 and the crankshaft rotate at the same rotational speed. Sensor data based on the detections by the proximity sensor 168 are transmitted from the crankshaft rotation sensor 98 to the gateway 56. In several exemplary embodiments, based on the sensor data taken by the crankshaft rotation sensor 98, the crankshaft rotation sensor 98 or the gateway 56 determines the number of times the crankshaft of the reciprocating pump assembly 52 rotates, calculates the rotational speed of the crankshaft, makes other calculations, or any combination thereof.

In several exemplary embodiments, the use of the proximity sensor pick-up collar 158 increases the precision and accuracy of the counting by the proximity sensor 168. In several exemplary embodiments, the use of the proximity sensor pick-up collar 158 increases the precision and accuracy of the counting by the proximity sensor 168 by, for example, limiting the detection to two detections per revolution of the collar 158, with one detection detecting the outer-diameter transition region 163a and the other detection detecting the outer-diameter transition region 163b. In contrast, in several exemplary embodiments, if the proximity sensor 168 were to detect teeth as a gear, such as a bull gear, rotates, there would be more opportunities for detection errors (false detections, missed detections, etc.) because there are more teeth in the gear, and/or because there are more vibrations within the gear.

In several exemplary embodiments, instead of being operably coupled to the rotary union 152, the collar 158 is operably coupled to another component that rotates along with the crankshaft such as, for example, a bushing shaft (not shown) to which the rotary union 152 is connected. In several exemplary embodiments, instead of being operably coupled to the rotary union 152, the collar 158 is operably coupled to another component that rotates along with the crankshaft such as, for example, a bushing shaft (not shown) to which the rotary union 152 is operably coupled, and the collar 158 and the crankshaft position sensor 98 are positioned within the gear cover 128, rather than outside of the gear cover 128, so that the distal end 170 of the proximity sensor 168 may be positioned proximate the bushing shaft. In several exemplary embodiments, instead of the employing the collar 158, the proximity sensor 168 may be configured to detect outer-diameter transition region(s) formed in the crankshaft itself, or in another component that rotates along with the crankshaft; for example, two outer-diameter transition regions may be formed in the bushing shaft itself by, for example, making one circumferential half of the bushing shaft have an outer diameter that is less than the outer diameter of the other circumferential half of the bushing shaft.

Although the exemplary embodiments illustrated in FIGS. 8, 9A, 9B, 10, and 11 are described above in connection with the hydraulic fracturing pump system 16, each of the hydraulic fracturing pump systems 18, 20, and 22 may also include components that are substantially identical to the exemplary embodiments illustrated in FIGS. 8, 9A, 9B, 10, and 11.

Figure 12:
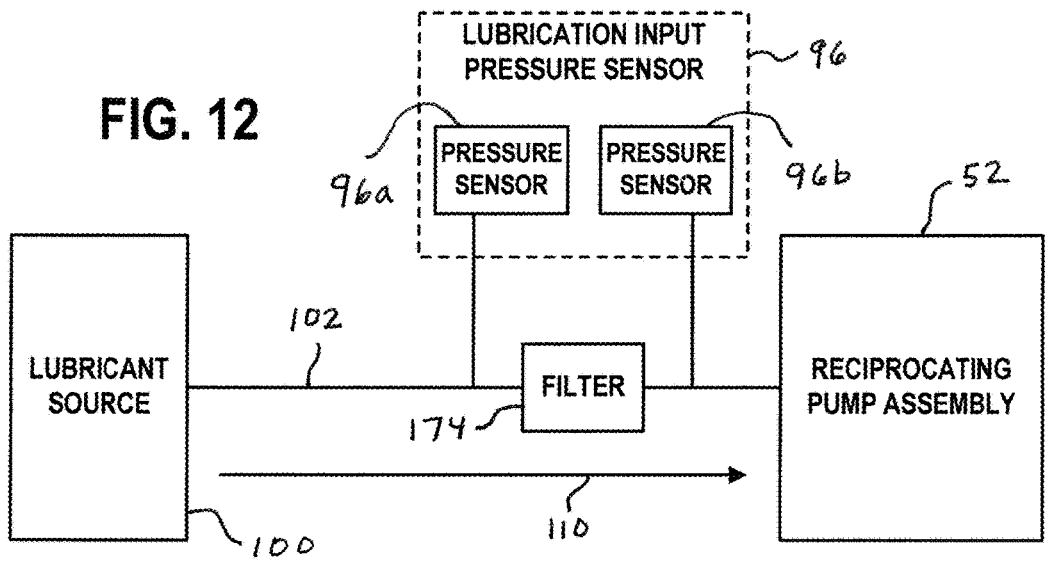
FIG. 12 is a diagrammatic view of a portion of the pump analysis system of FIG. 6, and the portion of the hydraulic fracturing pump system of FIG. 6, according to another exemplary embodiment.

In an exemplary embodiment, as illustrated in FIG. 12 with continuing reference to FIGS. 1, 2, 6, and 7, the pressure sensor 96 includes pressures sensors 96a and 96b, each of which is operably coupled to the lubrication input fluid line 102. A filter 174 is also operably coupled to the lubrication input fluid line 102 in an in-line configuration. The pressure sensor 96a is operably coupled to the lubrication input fluid line 102 at a position upstream of the filter 174. The pressure sensor 96b is operably coupled to the lubrication input fluid line 102 at a position downstream of the filter 174. In an exemplary embodiment, the pressure sensors 96a and 96b are combined into a single sensor.

Figure 13:
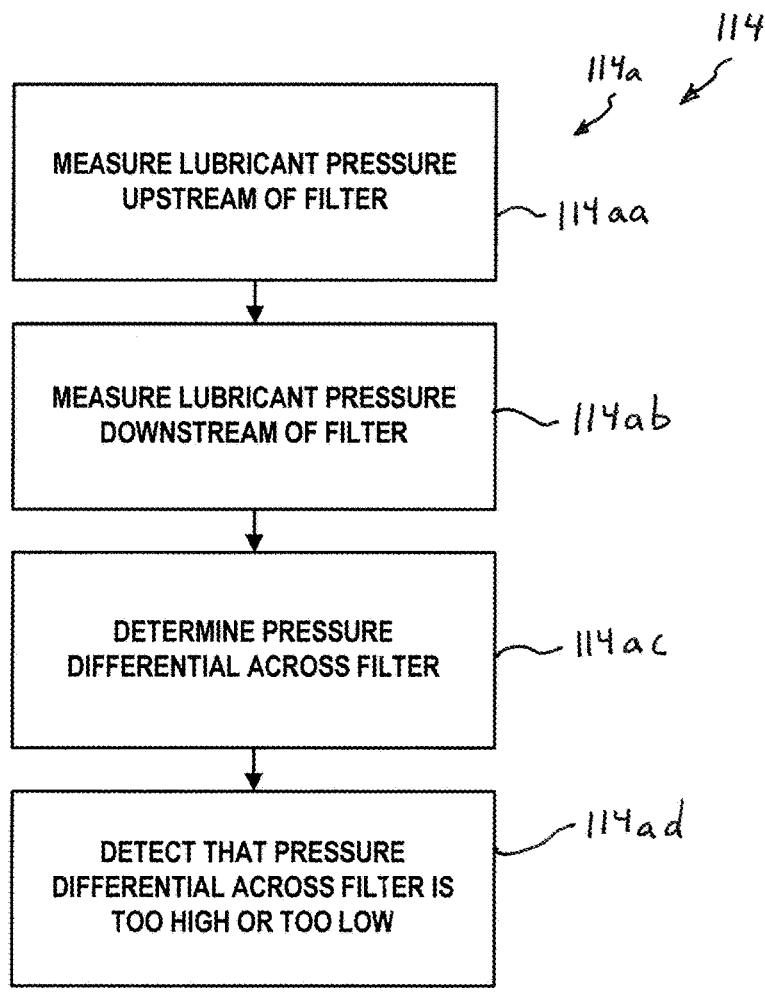
FIG. 13 is a flow chart illustration of a step of the method of FIG. 7 employing the portion of the pump analysis system of FIG. 12, according to an exemplary embodiment.

In an exemplary embodiment, as illustrated in FIG. 13 with continuing reference to FIGS. 1, 2, 6, 7, and 12, an exemplary embodiment of the step 114 of the method 112 of FIG. 7 is generally referred to by the reference numeral 114a. At the step 114a, the detected event is that the pressure differential across the filter 174 is too high or too low. The step 114a includes measuring the pressure of the lubricant upstream of the filter 174 at step 114aa, measuring the pressure of the lubricant downstream of the filter 174 at step 114ab, determining the pressure differential across the filter 174 at step 114ac, and detecting that the pressure differential across the filter 174 is too high or too low at step 114ad.

In an exemplary embodiment, the steps 114*aa* and 114*ab* are executed using the pressure sensors 96*a* and 96*b*, respectively. In an exemplary embodiment, the step 114*ac* includes using the one or more processors 58 of the gateway 56 to analyze, condition, or otherwise process the data from the sensors 96*a* and 96*b* and thereby determine the pressure differential across the filter 174. In an exemplary embodiment, the step 114*ac* includes sending the sensor data received from the sensor 96*a* and 96*b*, the sensor data as processed, the determined one or more operating parameters, and/or any combination thereof, from the gateway 56 to the application server 36, and using the gateway 56 and/or the application server 36 to determine the pressure differential across the filter 174. In an exemplary embodiment, at the step 114*ad*, the one or more processors 58 of the gateway 56 or the application server 36 compares the pressure differential across the filter 174 determined at the step 114*ac* with one or more set thresholds, thereby detecting whether the pressure differential across the filter 174 is too high or too low.

In an exemplary embodiment, at the step 114*ad*, the gateway 56 or the application server 36 compares the pressure differential across the filter 174 with one or more set thresholds and detects that the pressure differential is too high; in several exemplary embodiments, this too-high detection indicates that the filter 174 is clogged and needs to be inspected, replaced, or otherwise serviced.

In an exemplary embodiment, at the step 114*ad*, the gateway 56 or the application server 36 detects that the pressure differential across the filter 174 is too close to zero, or at zero; in several exemplary embodiments, this too-low detection indicates that the filter 174 is clogged or otherwise inoperable and the lubricant flowing in the fluid line 102 has entered a bypass mode in which the lubricant bypasses the filter 174; this bypass-mode detection indicates that the filter 174 needs to be inspected, replaced, or otherwise serviced.

In several exemplary embodiments, before, during, or after the step 114*ad*, the steps 116 and 118 of the method 112 are executed in accordance with the foregoing, with the step 118 including activating an alarm to indicate that the pressure differential across the filter 174 is too high or too low, and/or that the filter 174 needs to be inspected, replaced, or otherwise serviced.

In several exemplary embodiments, the filter 174 is positioned on, or within, the reciprocating pump assembly 52. In several exemplary embodiments, the filter 174 is on board the reciprocating pump assembly 52, providing on-board filtration. In several exemplary embodiments, the filter 174 is operably coupled to a lubricant return line (not shown), through which the lubricant flows back into the lubricant source 100. In several exemplary embodiments, the filter 174 and the sensors 96*a* and 96*b* are positioned on, or within, the reciprocating pump assembly 52. In several exemplary embodiments, the filter 174 and the sensors 96*a* and 96*b* are on board the reciprocating pump assembly 52, providing on-board filtration. In several exemplary embodiments, the filter 174 and the sensors 96*a* and 96*b* are operably coupled to a lubricant return line (not shown), through which the lubricant flows back into the lubricant source 100.

In several exemplary embodiments, the exemplary embodiments illustrated in at least FIGS. 6-13 and described in the foregoing paragraphs operate to protect hydraulic fracturing pumping systems from failures resulting from lubrication issues, providing the capability to monitor in real-time lubrication conditions of hydraulic fracturing pumping systems and the locations thereof.

Figure 14A:
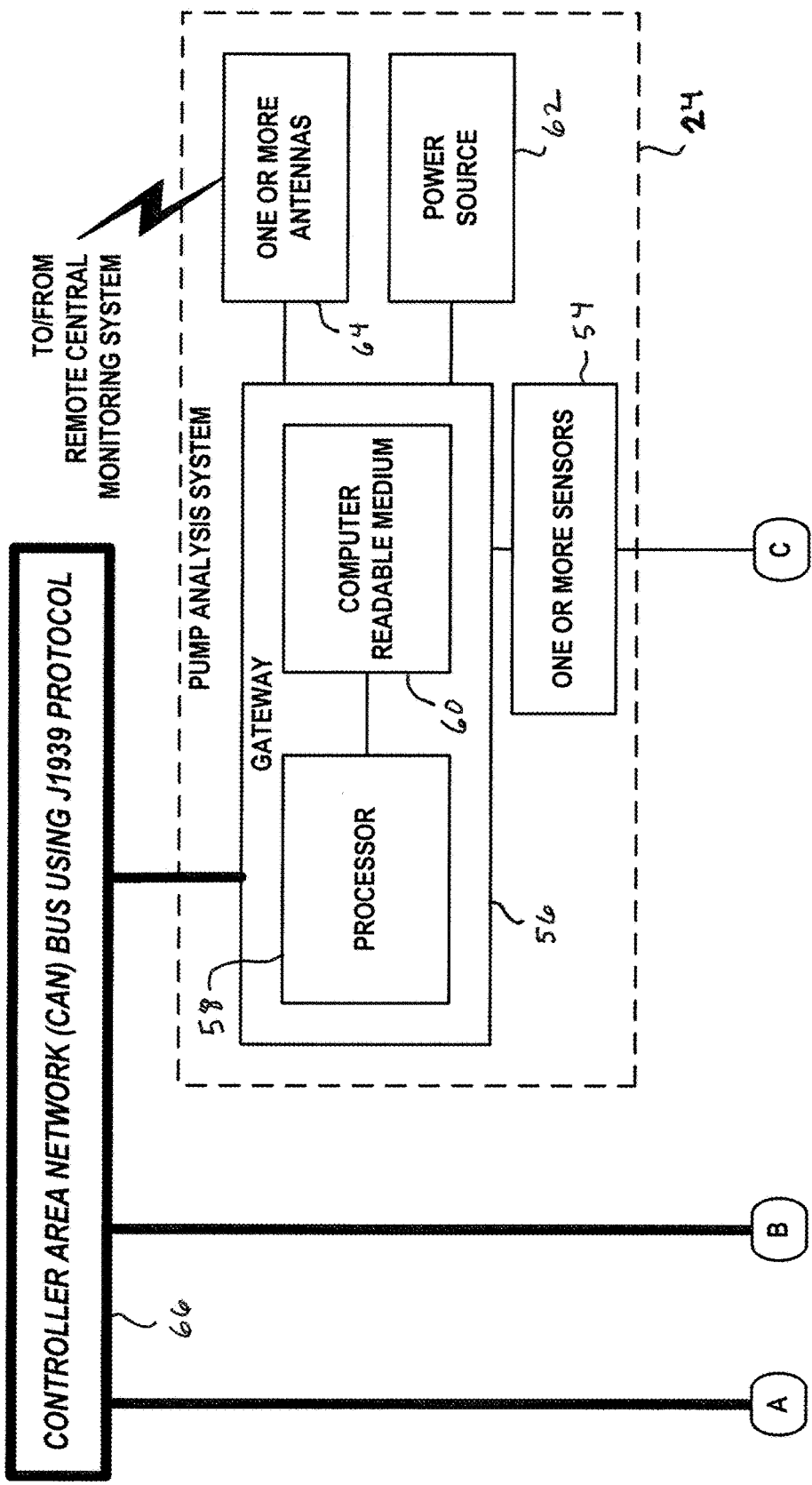
FIGS. 14A and 14B together form a diagrammatic illustration of the hydraulic fracturing pump system of FIG. 3, and the corresponding pump analysis system of FIG. 3 operably coupled thereto, according to an exemplary embodiment.
Figure 14B:
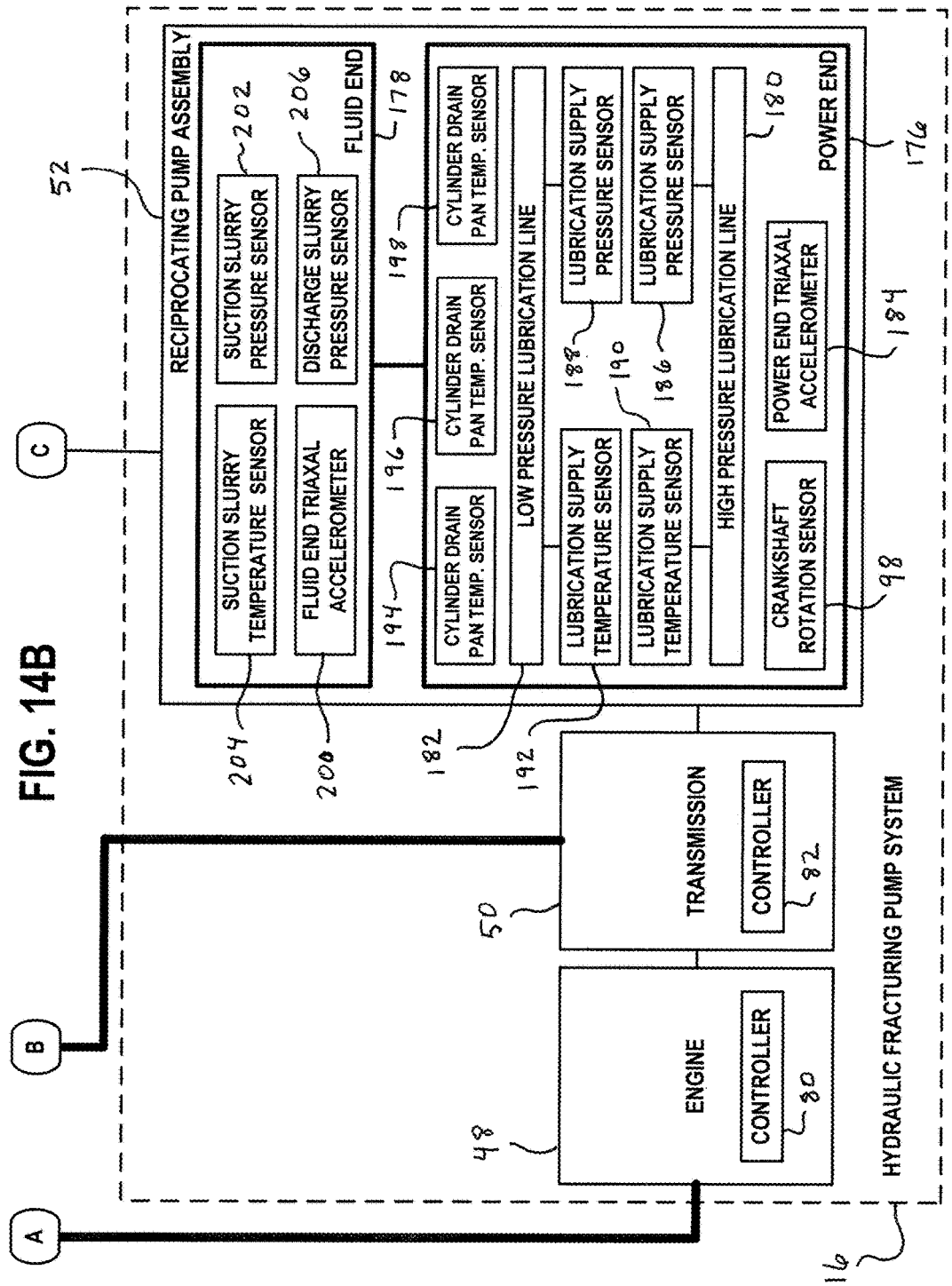

In an exemplary embodiment, as illustrated in FIGS. 14A and 14B with continuing reference to FIGS. 1-13, the reciprocating pump assembly 52 includes a power end 176 and a fluid end 178 operably coupled thereto. In an exemplary embodiment, the power end 176 includes a high pressure lubrication line 180 and a low pressure lubrication line 182.

As shown in FIG. 14B, in an exemplary embodiment, the one or more sensors 54 of the pump analysis system 24 include: the crankshaft rotation sensor 98, which is operably coupled to the power end 176; a power end triaxial accelerometer 184, which is mounted on, or otherwise operably coupled to, the power end 176; lubrication supply pressure sensors 186 and 188, which are operably coupled to the high pressure lubrication line 180 and the low pressure lubrication line 182, respectively; lubrication supply temperature sensors 190 and 192, which are operably coupled to the high pressure lubrication line 180 and the low pressure lubrication line 182, respectively; cylinder drain pan temperature sensors 194, 196, and 198, which are operably coupled to respective cylinder drain pans (not shown) of the power end 176; a fluid end triaxial accelerometer 200, which is mounted on, or otherwise operably coupled to, the fluid end 178; a suction slurry pressure sensor 202, which is operably coupled to the fluid end 178; a suction slurry temperature sensor 204, which is operably coupled to the fluid end 178; and a discharge slurry pressure sensor 206, which is operably coupled to the fluid end 178; in several exemplary embodiments, the one or more sensors 54 of the pump analysis system 24 further include the lubrication input oil quality sensor 92 (shown in FIG. 6), which is operably coupled to at least one of the high pressure lubrication line 180 and the low pressure lubrication line 182, and, in several exemplary embodiments, another lubrication input oil quality sensor (not shown) similar to that of the sensor 92 and operably coupled to the other of the high pressure lubrication line 180 and the low pressure lubrication line 182.

In an exemplary embodiment, instead of the power end triaxial accelerometer 184, the one or more sensors 54 include one or more power end uniaxial accelerometers, one or more power end biaxial accelerometers, a plurality of power end triaxial accelerometers, or any combination thereof. In an exemplary embodiment, instead of the fluid end triaxial accelerometer 200, the one or more sensors 54 include one or more fluid end uniaxial accelerometers, one or more fluid end biaxial accelerometers, a plurality of fluid end triaxial accelerometers, or any combination thereof.

In an exemplary embodiment, the three cylinder drain pan temperature sensors 194, 196, and 198 are for a triplex reciprocating pump assembly having three plungers and three cylinder drain pans. In an exemplary embodiment, the number of cylinder drain pan temperature sensors may be increased; for example, the reciprocating pump assembly 52 may be a quintuplex pump with five plungers and five cylinder drain pans, with the one or more sensors 54 including five cylinder drain pan temperature sensors, one for each cylinder drain pan.

In operation, in an exemplary embodiment, with continuing reference to FIGS. 14A and 14B, the engine 48 rotates or drives the crankshaft (not shown) of the power end 176, thereby driving the reciprocating pump assembly 52. The engine 48 drives the crankshaft via the transmission 50. Plungers (not shown) of the reciprocating pump assembly 52 reciprocate, thereby pressurizing fracturing fluid or slurry, the slurry containing, for example, liquid materials, sand mixture particles, chemicals, etc. Due to the operation of the power end 176, slurry is suctioned into the fluid end 178, pressurized within the fluid end 178, and discharged out of the fluid end 178, subsequently flowing to a wellhead (not shown), which is the surface termination of a wellbore that extends within a subterranean formation; the pressurized slurry flows to the wellhead to be injected into the wellbore.

During the above-described operation of the exemplary embodiment of the hydraulic fracturing pump system 16 of FIGS. 14A and 14B, the one or more sensors 54 of the pump analysis system measure one or more physical properties associated with the reciprocating pump assembly 52. More particularly, the crankshaft rotation sensor 98 counts the number of times the crankshaft of the reciprocating pump assembly 52 rotates. In several exemplary embodiments, at least one of the crankshaft rotation sensor 98, the gateway 56, and the application server 36 determines the revolutions per minute (RPM) of the crankshaft 25. The power end triaxial accelerometer 184 measures vibration in the power end 176. In an exemplary embodiment, the power end triaxial accelerometer 184 measures displacement of the power end 176 of the reciprocating pump assembly 52.

The lubrication supply pressure sensors 186 and 188 measure the pressure of the supply lubricant in the high pressure lubrication line 180 and the low pressure lubrication line 182, respectively. The lubrication supply temperature sensors 190 and 192 measure the temperature of the supply lubricant in the high pressure lubrication line 180 and the low pressure lubrication line 182, respectively. Each of the cylinder drain pan temperature sensors 194, 196, and 198 measures the temperature of the lubricant in the drain pan to which the cylinder drain pan temperature sensor is operably coupled.

The fluid end triaxial accelerometer 200 measures vibration in the fluid end 178. In an exemplary embodiment, the fluid end triaxial accelerometer 200 measures displacement of the fluid end 178.

The suction slurry pressure sensor 202 measures the pressure of the flowing slurry before it is pressurized within the fluid end 178 by the operation of the power end 176, that is, before and/or during the suctioning of the slurry into the fluid end 178. The suction slurry temperature sensor 204 measures the temperature of the flowing slurry before it is pressurized within the fluid end 178. The discharge slurry pressure sensor 206 measures the pressure of the flowing slurry after it is pressurized within the fluid end 178 by the operation of the power end 176, that is, during and/or after the discharging of the slurry from the fluid end 178.

The operation of the remainder of the pump analysis system 24, including the gateway 56, the power source 62, and the one or more antennas 64, as well as the operation of the CAN bus 66, all of which are illustrated in FIG. 14A, have been described above in connection with the exemplary embodiments illustrated in FIG. 3 and therefore these operations will not be described in further detail with respect to FIG. 14A.

In several exemplary embodiments, the method 68 of FIG. 4 is executed using the exemplary embodiments illustrated in FIGS. 1, 2, 14A, and 14B in a manner identical to the manner in which the method 68 is executed using the exemplary embodiments illustrated in FIGS. 1-3.

In several exemplary embodiments, the step 78 of FIG. 5 is executed using the exemplary embodiments illustrated in FIGS. 1, 2, 14A, and 14B in a manner identical to the above-described manner in which the step 78 is executed using the exemplary embodiments illustrated in FIGS. 1-3.

Figure 15:
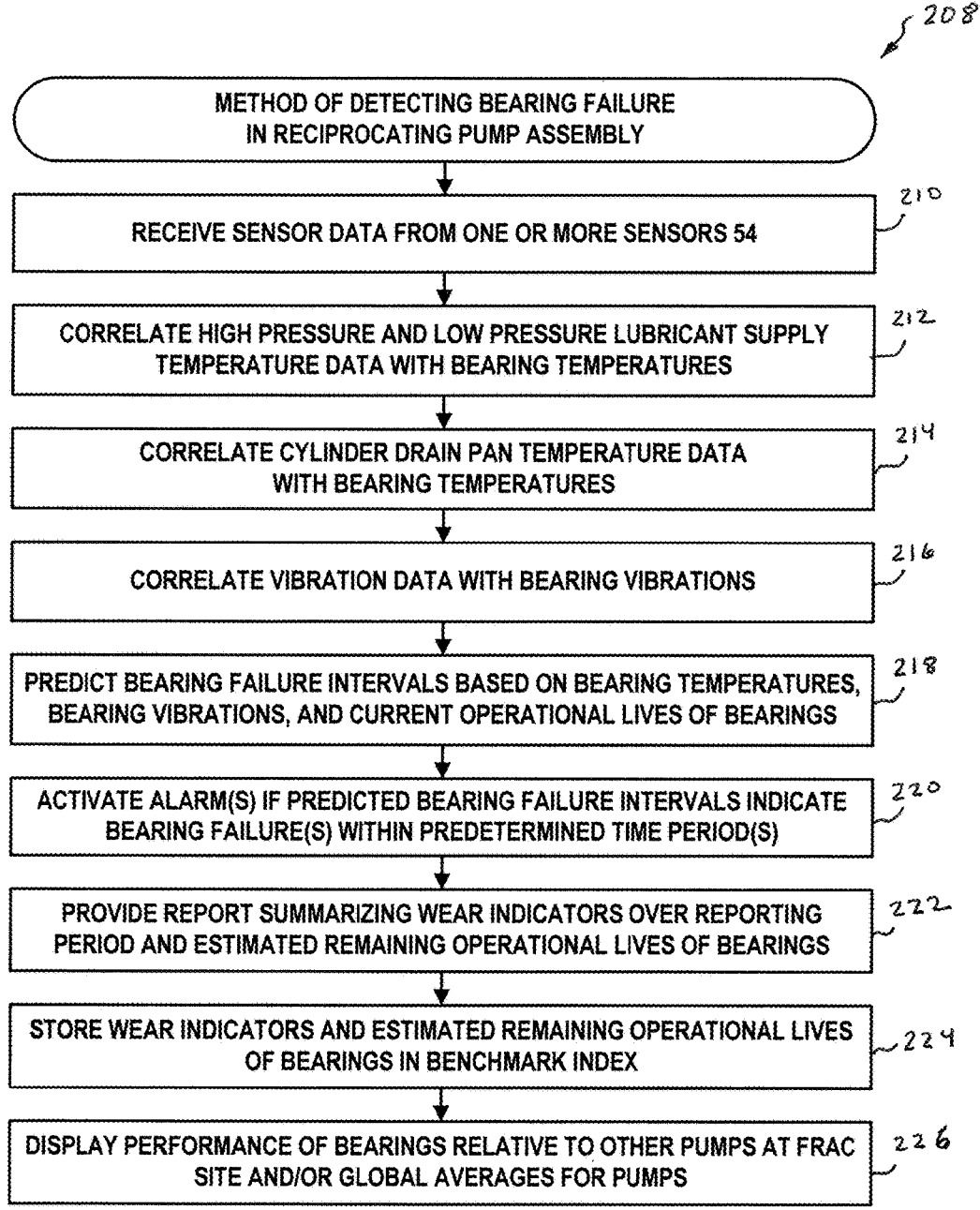
FIG. 15 is a flow chart illustration of a method of detecting bearing failure in the reciprocating pump assembly of FIGS. 14A and 14B, according to an exemplary embodiment.

In an exemplary embodiment, as illustrated in FIG. 15 with continuing reference to FIGS. 1-14B, a method of detecting bearing failure in the reciprocating pump assembly 52 of the pump system 16 is generally referred to by the reference numeral 208. In several exemplary embodiments, the method 208 is executed using the exemplary embodiments illustrated in FIGS. 1, 2, 14A, and 14B. Bearing failure in the reciprocating pump assembly 52 may occur when the bearings in the power end 176 (roller bearings, shaft pin shell bearings, shell thrust bearings, etc.) become excessively worn due to, for example, prolonged usage, contamination, abusive operation conditions, and/or any combination thereof; in several exemplary embodiments, lead indicators of bearing failure are excessive vibration and high bearing temperatures.

As shown in FIG. 15, in an exemplary embodiment, the method 208 includes: at step 210 receiving sensor data from the one or more sensors 54; at step 212 correlating high pressure and low pressure lubricant supply temperature data with bearing temperatures; at step 214 correlating cylinder drain pan temperature data with bearing temperatures; at step 216 correlating vibration data with bearing vibrations; at step 218 predicting bearing failure intervals based on the correlated bearing temperatures, correlated bearing vibrations, and current operational lives of the bearings within the reciprocating pump assembly 52; at step 220 activating alarm(s) if predicted failure intervals indicate bearing failure(s) within predetermined time period(s); at step 222 providing a report summarizing wear indicators over the reporting period and estimated remaining operational lives of bearings; at step 224 storing wear indicators and estimated remaining operational lives of bearings in a benchmark index; and at step 226 displaying performance of bearings within the reciprocating pump assembly 52 relative to other pumps at the frac site 12 (such as the hydraulic fracturing pump system 18) and/or global averages for pumps. In several exemplary embodiments, the method 208 is executed to detect failure in one or more roller bearings, shaft pin shell bearings, shell thrust bearings, other bearings, etc. within the reciprocating pump assembly 52; in several exemplary embodiments, one or more of these bearings support the crankshaft, the rotation of which is counted by the crankshaft rotation sensor 98.

In an exemplary embodiment, at the step 210, sensor data is received from at least one or more of the temperature sensors 190, 192, 194, 196, and 198, and the power end triaxial accelerometer 184, of the one or more sensors 54. In an exemplary embodiment, at the step 210, sensor data is received from at least the temperature sensors 190, 192, 194, 196, and 198, the power end triaxial accelerometer 184, and the fluid end triaxial accelerometer 200 of the one or more sensors 54. In several exemplary embodiments, the sensor data is received by the gateway 56 at the step 210. In several exemplary embodiments, at the step 210, the sensor data is received by the gateway 56 and the application server 36. In several exemplary embodiments, at the step 210, the sensor data is received by the gateway 56, the application server 36, and the remote user device 42 and/or 44.

In an exemplary embodiment, at the step 212, the high pressure and low pressure lubricant supply temperature data of one or more of the bearings within the reciprocating pump assembly 52 is correlated with bearing temperatures using heat transfer numerical solutions, finite element thermal analyses, heat transfer closed-form solutions, or any combination thereof. In several exemplary embodiments, at the step 212, the high pressure lubricant supply temperature data is correlated with bearing temperatures using historical experimental and/or operational data (empirical data recorded from past experiments and/or past pump operations). In several exemplary embodiments, at the step 212, the high pressure lubricant supply temperature data is correlated with bearing temperatures using one or more of the gateway 56, the application server 36, and the remote user device 42 and/or 44.

In an exemplary embodiment, at the step 214, the cylinder drain pan temperature data is correlated with bearing temperatures using heat transfer numerical solutions, finite element thermal analyses, heat transfer closed-form solutions, or any combination thereof. In several exemplary embodiments, at the step 214, the cylinder drain pan temperature data is correlated with bearing temperatures using historical experimental and/or operational data (empirical data recorded from past experiments and/or past pump operations). In several exemplary embodiments, at the step 214, the cylinder drain pan temperature data is correlated with bearing temperatures using one or more of the gateway 56, the application server 36, and the remote user device 42 and/or 44.

In an exemplary embodiment, at the step 216, the vibration data from the reciprocating pump assembly 52 is correlated with bearing vibrations using vibration numerical solutions, finite element dynamic analyses, vibration closed-form solutions, or any combination thereof. In several exemplary embodiments, at the step 216, the vibration data is correlated with bearing vibrations using historical experimental and/or operational data. In several exemplary embodiments, at the step 216, the vibration data is correlated with bearing vibrations using one or more of the gateway 56, the application server 36, and the remote user device 42 and/or 44.

In an exemplary embodiment, at the step 218, bearing failure intervals of one or more of the bearings within the reciprocating pump assembly 52 are predicted based on the bearing temperatures correlated at the steps 212 and 214, the bearing vibrations correlated at the step 216, and current operational lives of the bearings. In an exemplary embodiment, at the step 218, excessive oscillations outside of acceptable tolerances for bearing temperature and bearing vibration are detected, with the excessive oscillations serving as a basis for predicting the bearing failure intervals, thereby determining when one or more bearings within the reciprocating pump assembly 52 will need to be replaced or reconditioned. In several exemplary embodiments, at the step 218, the bearing failure intervals are predicted using one or more of the gateway 56, the application server 36, and the remote user device 42 and/or 44.

Figure 16:
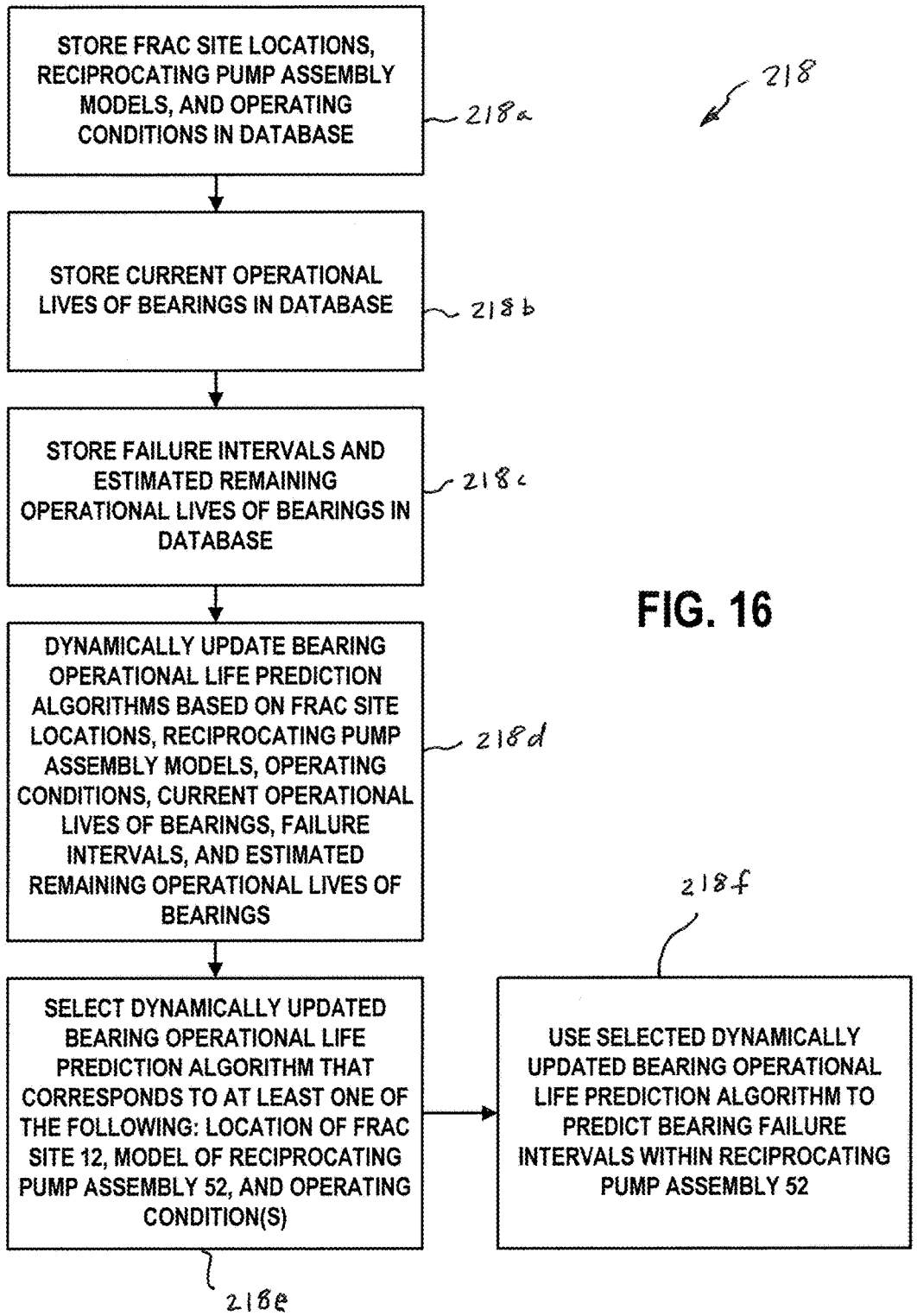
FIG. 16 is a flow chart illustration of a step of the method of FIG. 15, according to an exemplary embodiment.

In an exemplary embodiment, as illustrated in FIG. 16 with continuing reference to FIGS. 1-15, the step 218 includes at step 218a storing data sets in the database 41, with the data sets including data associated with respective frac site locations, reciprocating pump assembly models at the frac site locations, and operating conditions of the models at the frac site locations. In several exemplary embodiments, regarding the step 218a, the operating conditions with which the stored data sets are associated include bearing temperatures, bearing vibrations, the working pressures of the reciprocating pump assemblies, the applications for which the reciprocating pump assemblies are being used, the ambient temperatures surrounding the subject reciprocating pump assemblies, high pressure lubricant supply temperatures as measured by the respective temperature sensors 190 of different analysis systems each of which is substantially similar to the pump analysis system 24 of FIGS. 14A and 14B, low pressure lubricant supply temperatures as measured by the respective temperature sensors 192 of different analysis systems each of which is substantially similar to the pump analysis system 24 of FIGS. 14A and 14B, cylinder drain pan temperatures as measured by the respective sensors 194 of different analysis systems each of which is substantially similar to the pump analysis system 24 of FIGS. 14A and 14B, cylinder drain pan temperatures as measured by the respective sensors 196 of different analysis systems each of which is substantially similar to the pump analysis system 24 of FIGS. 14A and 14B, cylinder drain pan temperatures as measured by the respective sensors 198 of different analysis systems each of which is substantially similar to the pump analysis system 24 of FIGS. 14A and 14B, vibration data measured by the respective power end triaxial accelerometers 184 of different analysis systems each of which is substantially similar to the pump analysis system 24 of FIGS. 14A and 14B, vibration data measured by the respective fluid end triaxial accelerometers 200 of different analysis systems each of which is substantially similar to the pump analysis system 24 of FIGS. 14A and 14B, etc., or any combination thereof. At step 218b, stored in the database 41 are data sets associated with the current operational lives of bearings of the respective reciprocating pump assemblies 52 of different pump systems each of which is substantially similar to the pump system 16 of FIGS. 14A and 14B. At step 218c, stored in the database 41 are data sets associated with failure intervals and estimated remaining operational lives of bearings of the respective reciprocating pump assemblies 52 of different pump systems each of which is substantially similar to the pump system 16 of FIGS. 14A and 14B.

In several exemplary embodiments, the data sets stored at the steps 218a, 218b, and 218c are associated with respective ones of the reciprocating pump assemblies 52 located at frac sites throughout the world, throughout a continent such as North America, throughout a region such as the American States under which the Marcellus Shale Formation is found, throughout a state such as Texas, or any combination thereof. In several exemplary embodiments, instead of, or in addition to the reciprocating pump assembly 52 of the pump system 16, the data sets stored at the steps 218a, 218b, and 218c are associated with reciprocating pump assemblies other than the reciprocating pump assembly 52 of the pump system 16. In several exemplary embodiments, the data sets stored at the steps 218a, 218b, and 218c are associated with one or more of the respective reciprocating pump assemblies 52 of the hydraulic fracturing pump systems 18, 20, and 22.

In several exemplary embodiments, instead of, or in addition to the database 41, the data sets stored at the steps 218a-218c are stored in another portion of the computer readable medium 40, the remote user device 42, the remote user device 44, the computer readable medium 60, another computer readable medium, or a combination thereof.

At step 218d, bearing operational life prediction algorithms are dynamically updated based on the data sets stored at the steps 218a, 218b, and 218c. At step 218e, at least one of the dynamically updated bearing operational life prediction algorithms is selected, the selected algorithm corresponding to at least one of the following parameters associated with the reciprocating pump assembly 52 of the pump system 16: the location of the frac site 12 (or the frac site 12 itself); the particular model of the reciprocating pump assembly 52; and the operating conditions of the reciprocating pump assembly 52 (bearing temperatures within the reciprocating pump assembly 52, bearing vibrations within the reciprocating pump assembly 52, the working pressure of the reciprocating pump assembly 52, the application for which the reciprocating pump assembly 52 is being used, the ambient temperature surrounding the reciprocating pump assembly 52, high pressure lubricant supply temperature, low pressure lubricant supply temperature, power end vibration, cylinder drain pan temperature, etc.). For example, the dynamically updated algorithm selected at the step 218d is applicable to a reciprocating pump assembly being located at the frac site 12, a reciprocating pump assembly model that is the same as model of the reciprocating pump assembly 52 of the pump system 16, and having one or more operating conditions that match one or more of the operating conditions of the reciprocating pump assembly 52 of the pump system 16.

At step 218f, the dynamically updated bearing operational life prediction algorithm selected at the step 218e is used to predict bearing failure intervals of bearings within the reciprocating pump assembly 52 and thus the remaining operational lives of the bearings.

In several exemplary embodiments, the step 218 enables dynamic algorithm updates to the location where processing and data analysis are occurring, enabling machine learning; for example, the repeated execution of the step 218 with different reciprocating pump assemblies reveals that a certain equipment model is susceptible to a particular condition and subsequent executions of the step 218 are aware of that susceptibility and account for that susceptibility when predicting bearing failure intervals and remaining operational lives of bearings.

In several exemplary embodiments, the steps 218a, 218b, and 218c are not specific to any particular reciprocating pump assembly, whereas the steps 218d and 218e are specific to a particular reciprocating pump assembly, which in the case of the present description is the reciprocating pump assembly 52 of the pump system 16.

At the step 220, one or more alarms are activated if at the step 218d it is determined that remaining operational lives of one or more bearings within the reciprocating pump assembly 52 are less than or equal to a predetermined time period such as, for example, 1 day, 6 hours, 1 hour, etc. In an exemplary embodiment, the step 220 includes graphically depicting an alarm on the remote user devices 42 and/or 44, the alarm indicating the existence of a potential bearing failure within the reciprocating pump assembly 52. As a result, the users of the remote user devices 42 and/or 44 are alerted to the existence of the potential bearing failure. In an exemplary embodiment, the step 118 includes graphically depicting an alarm on another output device that is in communication with the gateway 56 and/or the application server 36, such as a display screen in a control van located at the frac site 12. As a result, an operator in the control van is alerted to the bearing failure potential. In an exemplary embodiment, the step 118 includes the gateway 56, the application server 36, the remote user device 42, or the remote user device 44 sending one or more email messages, one or more text messages, one or more other messages, or any combination thereof; the one or messages indicate the potential bearing failure and the location thereof. In an exemplary embodiment, the step 118 includes the gateway 56, the application server 36, the remote user device 42, or the remote user device 44 flagging the potential bearing failure for immediate notification, and/or flagging the potential bearing failure and storing the flagging for notification at a later time.

As indicated above, at the step 222, a report is generated summarizing wear indicators over the reporting period and estimated remaining operational lives of bearings within the reciprocating pump assembly 52.

At the step 224, in an exemplary embodiment, the wear indicators and estimated remaining operational lives of the bearings within the reciprocating pump assembly 52 are stored in a benchmark index in, for example, the database 41. At the step 226, the performance of the bearings within the reciprocating pump assembly 52 of the pump system 16 is displayed on, for example, the remote user device 42 or 44; at the step 226, in several exemplary embodiments, performance data of these bearings are compared to performance data of other bearings for other reciprocating pump assemblies located at the frac site 12, and/or global averages, which performance data and global averages are stored in the benchmark index referenced at the step 224.

Figure 17:
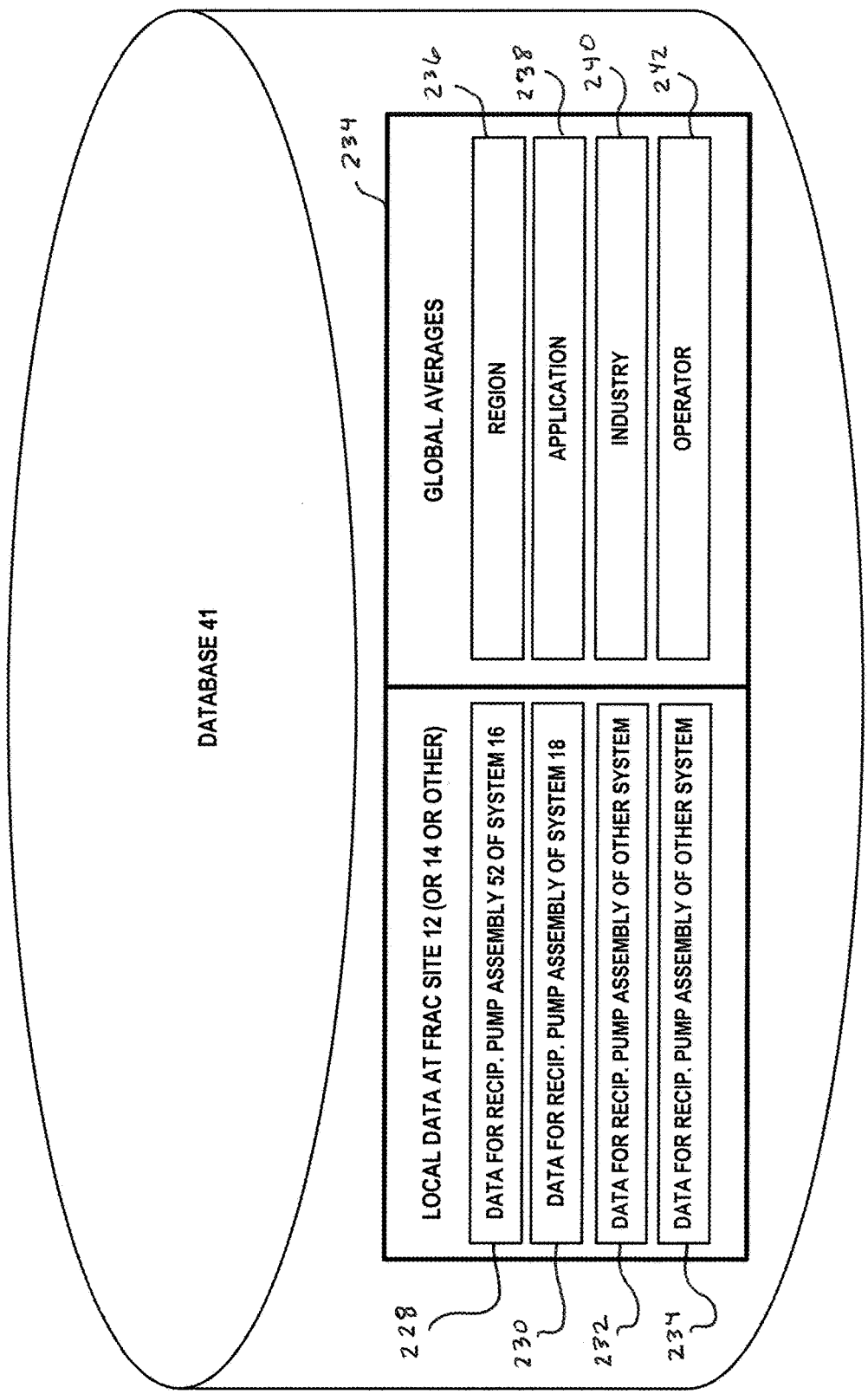
FIG. 17 is a diagrammatic illustration of a database accessed during the execution of the method of FIG. 15, according to an exemplary embodiment.

In an exemplary embodiment, as illustrated in FIG. 17 with continuing reference to FIGS. 1-16, there is provided a diagrammatic illustration of the benchmark index referenced at the steps 224 and 226. In FIG. 17, reference numeral 228 is used to refer to benchmark data stored in the database 41 and associated with the wear indictors and estimated remaining operational lives of the bearings within the reciprocating pump assembly 52 of the pump system 16, the benchmark data 228 being so stored at the step 224. At the step 226, performance data of the bearings of the reciprocating pump assembly 52 are compared to benchmark data 230 of the performance of the bearings of the reciprocating pump assembly of the hydraulic fracturing pump system 18 located at the frac site 12, benchmark data 232 of a reciprocating pump assembly of another hydraulic fracturing pump system located at the frac site 12, benchmark data 234 of a reciprocating pump assembly of yet another hydraulic fracturing pump system located at the frac site 12, or a combination thereof. Instead of, or in addition to, a local comparison, at the step 226 the performance data of the bearings of the reciprocating pump assembly 52 are compared to global averages 234. In several exemplary embodiments, the global averages 234 may be segmented by region 236, application 238, industry 240, and operator 242 of the reciprocating pump assembly 52.

In several exemplary embodiments, one or more of the correlation steps 212, 214, and 216 are omitted from the method 208 and, at the step 218. In several exemplary embodiments, the correlation steps 212, 214, and 216 are omitted from the method 208 and, at the step 218, the bearing failure intervals are predicted based on one or more of the high pressure lubricant supply temperature data received at the step 210, the low pressure lubricant supply temperature data received at the step 210, the cylinder drain pan temperature data received at the step 210, and the vibration data received at the step 210; in several exemplary embodiments, these predictions are made based upon historical experimental and/or operational data (empirical data recorded from past experiments and/or past pump operations) with such data indicating, for example, that when the power end 176 undergoes certain vibrations, the supply temperature(s) are too hot for too long, and/or the cylinder drain pan temperature(s) are too hot for too long, bearings fail within a certain time period. In several exemplary embodiments, the correlation steps 212, 214, and 216 are omitted from the method 208 and, at the step 218, the operating conditions do not include either correlated bearing temperatures or correlated bearing vibrations.

Figure 18:
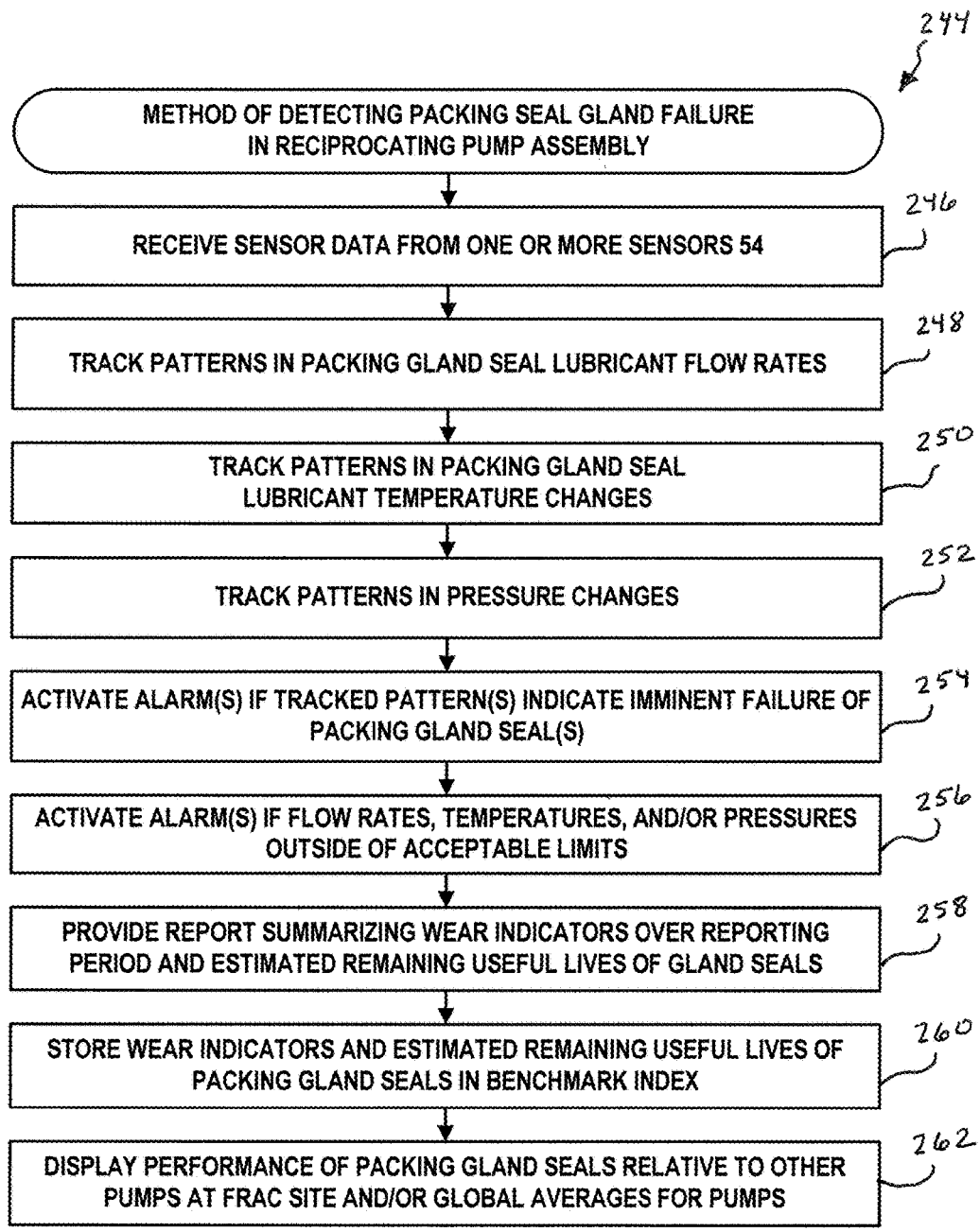
FIG. 18 is a flow chart illustration of a method of detecting packing gland seal failure in the reciprocating pump assembly of FIGS. 14A and 14B, according to an exemplary embodiment.

In an exemplary embodiment, as illustrated in FIG. 18 with continuing reference to FIGS. 1-17, a method of detecting packing seal gland failure within the reciprocating pump assembly 52 of the pump system 16 is generally referred to by the reference numeral 244. In several exemplary embodiments, the method 244 is executed using the exemplary embodiments illustrated in FIGS. 1, 2, 14A, and 14B. As discussed above, the power end 176 operates to cause plungers to reciprocate, thereby pressurizing fracturing fluid or slurry, the slurry containing, for example, liquid materials, sand mixture particles, chemicals, etc. Due to the operation of the power end 176, slurry is suctioned into the fluid end 178, pressurized within the fluid end 178, and discharged out of the fluid end 178. Respective packings surround the plungers at the fluid end 178, with packing seal glands sealing the respective interfaces between the plungers and the fluid end 178. An exemplary embodiment of a packing arrangement is described and illustrated in U.S. application Ser. No. 13/755,884, filed Jan. 31, 2013, the entire disclosure of which is hereby incorporated herein by reference.

As shown in FIG. 18, in an exemplary embodiment, the method 244 includes: at step 246 receiving sensor data from the one or more sensors 54; at step 248 tracking patterns in packing gland seal lubricant flow rates; at step 250 tracking patterns in packing gland seal lubricant temperature changes; at step 252 tracking patterns in pressure changes; at step 254 activating alarm(s) if tracked pattern(s) indicate imminent failure of packing gland seal(s); at step 256 activating alarm(s) if flow rates, temperatures, and/or pressures are outside of acceptable limits; at step 258 providing a report summarizing wear indicators over the reporting period and estimated remaining useful lives of packing gland seals; at step 260 storing wear indicators and estimated remaining useful lives of packing gland seals in a benchmark index; and at step 262 displaying performance of packing gland seals within the reciprocating pump assembly 52 relative to other pumps at the frac site 12 (such as the hydraulic fracturing pump system 18) and/or global averages for pumps.

In an exemplary embodiment, at the step 246, sensor data is received from at least one or more of the temperature sensors 190, 192, 194, 196, 198, and 204, and the pressure sensors 186, 188, 202, and 206, of the one or more sensors 54. In several exemplary embodiments, the sensor data is received by the gateway 56 at the step 246. In several exemplary embodiments, at the step 246, the sensor data is received by the gateway 56 and the application server 36. In several exemplary embodiments, at the step 246, the sensor data is received by the gateway 56, the application server 36, and the remote user device 42 and/or 44.

In an exemplary embodiment, at the step 248, the packing gland seal lubricant flow rates are calculated based on at least the pressure measurements as measured by the pressure sensors 186 and 188. In an exemplary embodiment, the reciprocating pump assembly 52 includes the filter 174 (shown in FIG. 12) and the sensor 186 includes two sensors, one upstream of the filter 174 and the other downstream of the filter 174; at the step 248, the lubricant flow rate is calculated based on the pressure drop across the filter 174 and changes in this flow rate are tracked. In an exemplary embodiment, the reciprocating pump assembly 52 includes another filter similar to the filter 174 and the sensor 188 includes two sensors, one upstream of the another filter and the other downstream of the another filter; at the step 248, the lubricant flow rate is calculated based on the pressure drop across the another filter and changes in this flow rate are tracked. In an exemplary embodiment, the reciprocating pump assembly 52 includes the filter 174 (shown in FIG. 12) and another filter similar to the filter 174, the sensor 186 includes two sensors, one upstream of the filter 174 and the other downstream of the filter 174, and the sensor 188 includes two sensors, one upstream of the another filter and the other downstream of the another filter; at the step 248, lubricant flow rates are calculated based on the respective pressure drops across the filter 174 and the another filter and changes in the packing gland lubricant flow rates are tracked.

In an exemplary embodiment, at the step 250, patterns in the packing gland seal lubricant temperature changes are tracked using at least the temperature measurements as measured by the lubrication supply temperature sensors 190 and 192. In an exemplary embodiment, at the step 250, patterns in the packing gland seal lubricant temperature changes are tracked using at least the temperature measurements as measured by the lubrication supply temperature sensors 190 and 192, and the cylinder drain pan temperature sensors 194, 196, and 198.

In an exemplary embodiment, at the step 252, patterns in pressure changes are tracked using at least the pressure measurements as measured by the lubrication supply pressure sensors 186 and 188. In an exemplary embodiment, at the step 252, patterns in pressure changes are tracked using at least the pressure measurements as measured by the lubrication supply pressure sensors 186 and 188, and one or both of the discharge slurry pressure sensor 206 and the suction slurry pressure sensor 202.

In an exemplary embodiment, at the step 254, alarm(s) are activated if the patterns tracked in one or more of the steps 248, 250, and 252 indicate imminent failure of packing gland seal(s) within the reciprocating pump assembly 52. In an exemplary embodiment, at the step 254, alarm(s) are activated if it is determined that the rate of change of the packing gland seal lubricant flow rate is too high or too low. In an exemplary embodiment, at the step 254, alarm(s) are activated if it is determined that the rate of change of the lubricant temperature is too high or too low. In an exemplary embodiment, at the step 254, alarm(s) are activated if it is determined that the rate of change of pressure is too high or too low, with the pressure being the lubricant supply pressure, the suction slurry pressure, the discharge slurry pressure, or a combination thereof. In several exemplary embodiments, the manners in which the alarm(s) are activated at the step 254 are similar to the above-described manners in which the alarm(s) are activated at the step 220. In several exemplary embodiments, at the step 254, the alarm(s) are activated using one or more of the gateway 56, the application server 36, and the remote user device 42 and/or 44. In several exemplary embodiments, at the step 254, algorithms are dynamically updated to enable machine learning with respect to tracking patterns and identifying cases of imminent packing gland seal failure; for example, the repeated execution of the step 254 with different reciprocating pump assemblies reveals that a certain equipment model is susceptible to a particular condition and subsequent executions of the step 254 are aware of that susceptibility and account for that susceptibility when predicting imminent packing gland seal failures and remaining useful lives of packing gland seals.

In an exemplary embodiment, at the step 256, if the packing gland seal lubricant flow rate exceeds a predetermined threshold, or falls below a predetermined threshold, alarm(s) are activated. In an exemplary embodiment, at the step 256, if the packing gland seal lubricant supply temperature exceeds a predetermined threshold, or falls below a predetermined threshold, alarm(s) are activated. In an exemplary embodiment, at the step 256, if the packing gland seal lubricant supply pressure exceeds a predetermined threshold, or falls below a predetermined threshold, alarm(s) are activated. In an exemplary embodiment, at the step 256, if the suction slurry pressure exceeds a predetermined threshold, or falls below a predetermined threshold, alarm(s) are activated. In an exemplary embodiment, at the step 256, if the discharge slurry pressure exceeds a predetermined threshold, or falls below a predetermined threshold, alarm(s) are activated. In several exemplary embodiments, the manners in which the alarm(s) are activated at the step 256 are similar to the above-described manners in which the alarm(s) are activated at the step 220. In several exemplary embodiments, at the step 256, the alarm(s) are activated using one or more of the gateway 56, the application server 36, and the remote user device 42 and/or 44.

In several exemplary embodiments, the steps 258, 260, and 262 are similar to the steps 222, 224, and 226, respectively; therefore, the steps 258, 260, and 262 will not be described in further detail.

In several exemplary embodiments, execution of the method 244 enables the detection of precursors to packing land seal failure due to, for example: excessive corrosion in sealing components such as lantern rings, gland packing, and plungers; excessive erosion/wear in sealing components such as lantern rings, gland packing, and plungers; and excessive friction between packing and plungers. In several exemplary embodiments, execution of the method 244 provides an early warning system that notifies personnel of imminent failure of packing gland seal(s) by tracking patterns in packing gland seal lubricant flow rate, temperature and pressure changes/deterioration.

Figure 19:
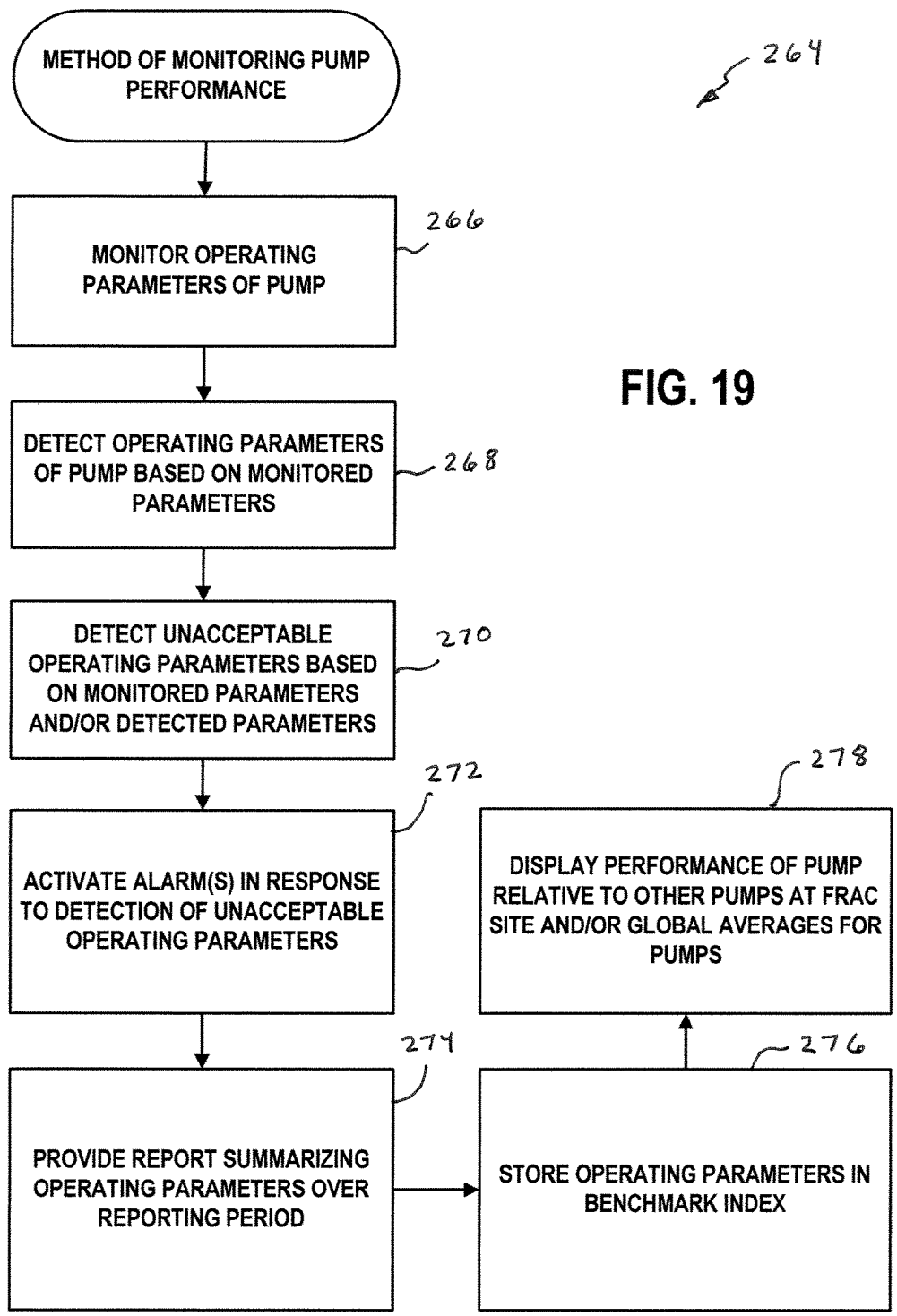
FIG. 19 is a flow chart illustration of a method of monitoring pump performance, according to an exemplary embodiment.

In an exemplary embodiment, as illustrated in FIG. 19 with continuing reference to FIGS. 1-18, a method of monitoring pump performance is generally referred to by the reference numeral 264 and includes: at step 266 monitoring operating parameters of the reciprocating pump assembly 52 of the pump system 16; at step 268 detecting operating parameters of the reciprocating pump assembly 52; at step 270 detecting unacceptable operating parameters of the reciprocating pump assembly 52 based on the parameters monitored at the step 266 and/or detected at the step 268; at step 272 activating alarm(s) in response to detecting unacceptable operating parameters at the step 270; at step 274 providing a report summarizing operating parameters over the reporting period; at step 276 storing operating parameters in a benchmark index; and at step 278 displaying operating parameters of the reciprocating pump assembly 52 relative to other pumps at the frac site 12 (such as the hydraulic fracturing pump system 18) and/or global averages for pumps.

In an exemplary embodiment, at the step 266, the monitored operating parameters include one or more of the following: vibrations in the power end 176 as measured by the power end triaxial accelerometer 184, lubrication supply pressure in the high pressure lubrication line 180 as measured by the sensor 186, lubrication supply pressure in the low pressure lubrication line 182 as measured by the sensor 188, lubrication supply temperature in the high pressure lubrication line 180 as measured by the sensor 190, lubrication supply temperature in the low pressure lubrication line 182 as measured by the sensor 192, cylinder drain pan lubricant temperatures in the power end 176 as measured by the sensors 194, 196, and 198, vibrations in the fluid end 178 as measured by the fluid end triaxial accelerometer 200, suction slurry pressure on the low pressure side of the fluid end 178 as measured by the sensor 202, suction slurry temperature at the low pressure side of the fluid end 178 as measured by the sensor 204, discharge slurry pressure at the high pressure side of the fluid end 178 as measured by the sensor 206, and lubricant quality as measured by the sensor 92.

In an exemplary embodiment, at the step 268, the detected operating parameters include one or more of the following: flow rate, rod load, shock load, pump operating speed, and pump power (calculated horsepower).

In an exemplary embodiment, at the step 270, precursors to cavitation are detected, including suction/discharge line blockages and incorrect valve positions. In an exemplary embodiment, at the step 270, excessive oscillations outside of acceptable tolerances are detected in the monitored/detected vibration data on one or both of the following: the drive side of the power end 176 near the pump gearing (gear box, drive shaft, pinion and bull gear, etc.) and cross heads, etc.; and the fluid end 178. In an exemplary embodiment, at the step 270, unacceptable variances are detected in or more of the following: pump suction pressure, pump discharge pressure, flow rate, and operating speed; in several exemplary embodiments, such unacceptable variances indicate potential deterioration of pump performance, and/or potential pump failure. In several exemplary embodiments, at the step 270, the detected unacceptable operating parameters (e.g., unacceptable variances in monitored and/or detected pump operating parameters) indicate pump performance deterioration caused by one or more of the following: cavitation; excessive damage on one or more pump parts such as valves, seats, fluid end, bearings, etc.; blockage in suction and/or discharge flow lines; and operating points that have moved away from the pump duty cycle.

In several exemplary embodiments, the manners in which the alarm(s) are activated at the step 272 are similar to the above-described manners in which the alarm(s) are activated at the step 220. In several exemplary embodiments, at the step 272, the alarm(s) are activated using one or more of the gateway 56, the application server 36, and the remote user device 42 and/or 44. In several exemplary embodiments, the steps 274, 276, and 278 are similar to the steps 222, 224, and 226, respectively; therefore, the steps 274, 276, and 278 will not be described in further detail.

Figure 20:
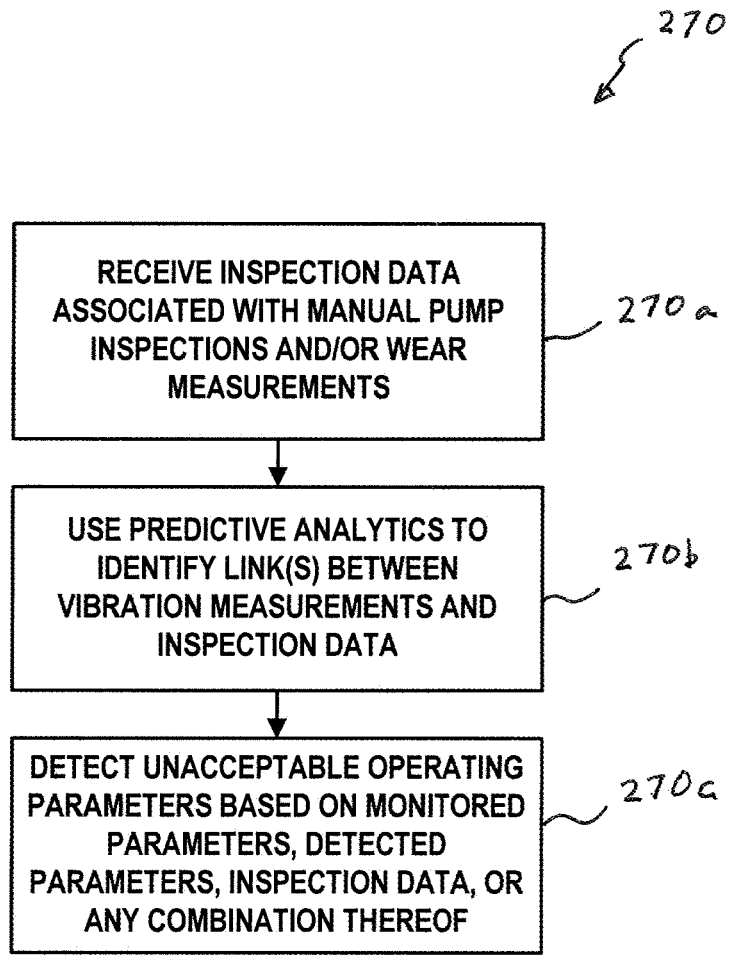
FIG. 20 is a flow chart illustration of a step of the method of FIG. 19, according to an exemplary embodiment.

In an exemplary embodiment, as illustrated in FIG. 20 with continuing reference to FIGS. 1-19, the step 270 includes: at step 270a receiving inspection data associated with manual pump inspections and/or wear measurements; at step 270b using predictive analytics to identify link(s) between vibration measurements and the inspection data received at the step 270a; and at step 270c detecting unacceptable operating parameters of the reciprocating pump assembly 52 based on the parameters monitored at the step 266, the parameters detected at the step 268, the inspection data received at the step 270a, or any combination thereof. In an exemplary embodiment, at the step 270b, the inspection data received at the step 270a is analyzed with respect to the vibration measurements made by the accelerometers 184 and/or 200, and link(s) between the data and the measurements are identified. In several exemplary embodiments, at the step 270, algorithms are dynamically updated to enable machine learning with respect to detecting unacceptable pump operating parameters; for example, the repeated execution of the step 270 with different reciprocating pump assemblies reveals that a certain equipment model is susceptible to a particular condition and subsequent executions of the step 270 are aware of that susceptibility and account for that susceptibility when determining that operating parameters of a particular pump are unacceptable.

Figure 21:
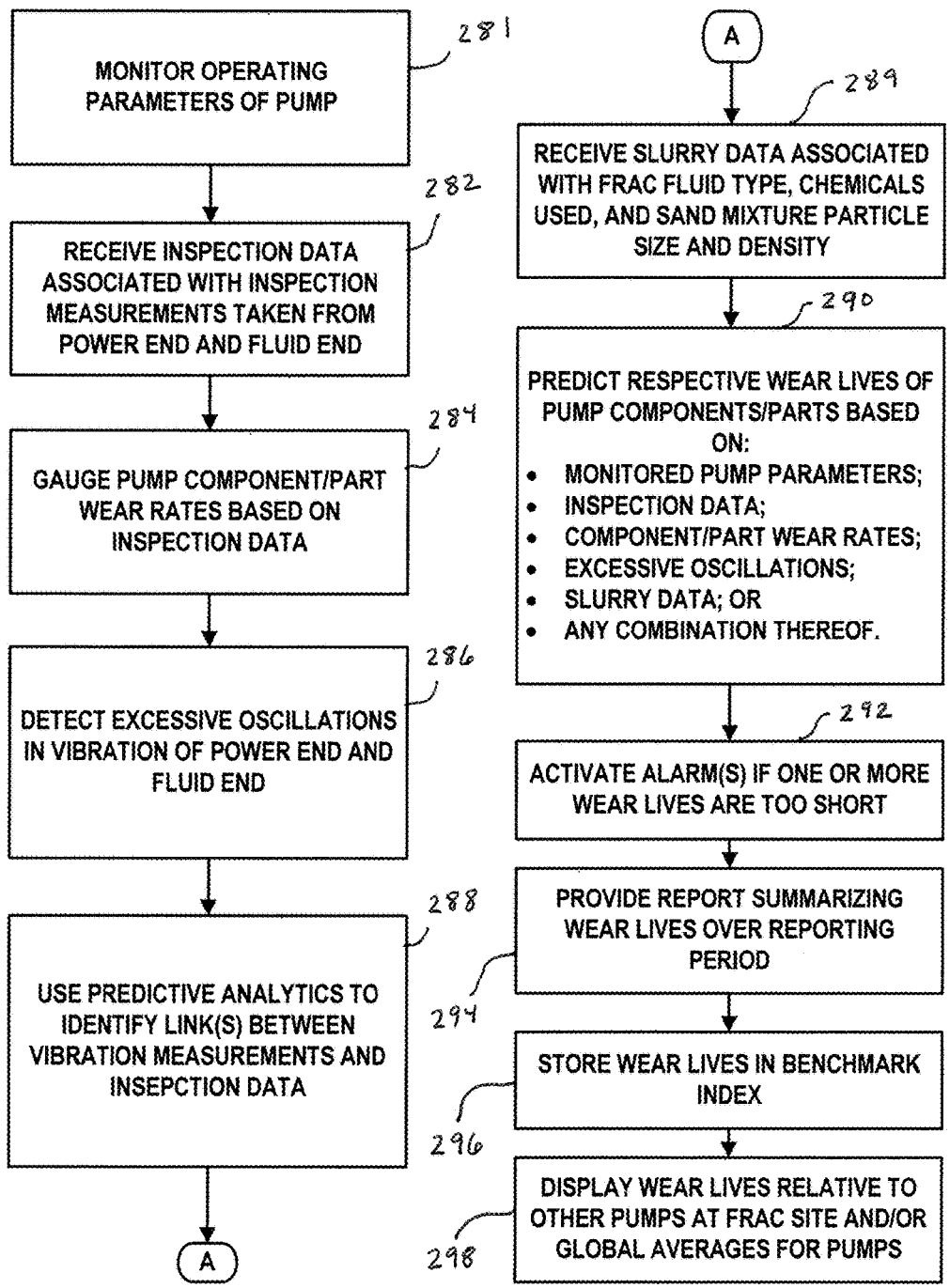
FIG. 21 is a flow chart illustration of a method of monitoring wear in a pump, according to an exemplary embodiment.

In an exemplary embodiment, as illustrated in FIG. 21 with continuing reference to FIGS. 1-20, a method of monitoring wear in the reciprocating pump assembly 52 of the pump system 16 is generally referred to by the reference numeral 280 and includes: at step 281 monitoring operating parameters of the pump; at step 282 receiving inspection data associated with inspection measurements taken from the power end 176 and/or the fluid end 178, thereby capturing, for example, pump part damage and/or wear measurements; at step 284 gauging pump component wear rates based on the inspection data received at the step 282; at step 286 detecting excessive oscillations outside of acceptable tolerances in the vibration of the power end 176 and/or the fluid end 178; at step 288 using predictive analytics to identify link(s) between vibration measurements and the inspection data received at the step 270*a*; at step 289 receiving slurry data associated with the frac fluid type in the slurry, the chemicals used in the slurry, and the sand mixture particle size and density in the slurry; at step 290 predicting respective wear lives, i.e., the respective remaining operational lives, of various parts/components of the reciprocating pump assembly 52 based on the operating parameters monitored at the step 281, the inspection data received at the step 282, the pump component wear rates gauged at the step 284, the excessive oscillations detected at the step 286, the link(s) identified at the step 288, and the slurry data received at the step 289, or any combination thereof; at step 292 activating alarm(s) if one or more wear lives are too short; at step 294 providing reports summarizing wear lives over the reporting period; at step 296 storing wear lives in a benchmark index; and at step 298 displaying respective wear lives of certain components/parts of the reciprocating pump assembly 52 of the pump system 16 relative to other pumps at the frac site 12 (such as the hydraulic fracturing pump system 18) and/or global averages for pumps.

In several exemplary embodiments, at the step 290, algorithms are dynamically updated to enable machine learning with respect to predicting respective wear lives; for example, the repeated execution of the step 290 with different reciprocating pump assemblies reveals that a certain equipment model is susceptible to a particular condition and subsequent executions of the step 290 are aware of that susceptibility and account for that susceptibility when predicting respective wear lives.

In several exemplary embodiments, the manners in which the alarm(s) are activated at the step 292 are similar to the above-described manners in which the alarm(s) are activated at the step 220. In several exemplary embodiments, at the step 292, the alarm(s) are activated using one or more of the gateway 56, the application server 36, and the remote user device 42 and/or 44. In several exemplary embodiments, the steps 294, 296, and 298 are similar to the steps 222, 224, and 226, respectively.

Figure 22:
FIG. 22 is a diagrammatic illustration of a report provided at a step of the method of FIG. 21, according to an exemplary embodiment.

In an exemplary embodiment, as illustrated in FIG. 22 with continuing reference to FIGS. 1-21, the report provided at the step 294 includes a set of component/part identifier fields 300, a corresponding set of remaining part life fields 302, a corresponding set of expected change out date fields 304 (setting forth dates on which the components/parts should be changed out or replaced), and a corresponding set of part lead time fields 306. In several exemplary embodiments, the fields 306 may be populated by lead time-related data fed directly from a manufacturer's enterprise resource planning (ERP) system. In several exemplary embodiments, the fields 306 may be populated by lead time-related data fed directly from a manufacturer's SAP ERP system.

In several exemplary embodiments, execution of at least the method 280 detects excessive wear in the reciprocating pump assembly 52 of the pump system 16 in order to eliminate, reduce the severity of, and/or reduce the extent of, one or more of the following: excessive power consumption, reduced pump flow, decrease in pump head, and early pump failure.

In several exemplary embodiments, execution of at least the method 280 detects excessive wear due to large abrasive particles being pumped through the fluid end 178, and the high/shock loading experienced by the power end 176, during operation of the hydraulic fracturing pump system 16 of which the reciprocating pump assembly 52 is a part. In several exemplary embodiments, the pump components/parts of which respective wear lives are predicted at the step 290 include one or more of the following: the fluid end 178, valves and seats within the fluid end 178, plungers driven by the power end 176, packing and seals, and bearings and bearing surfaces.

Figure 23:
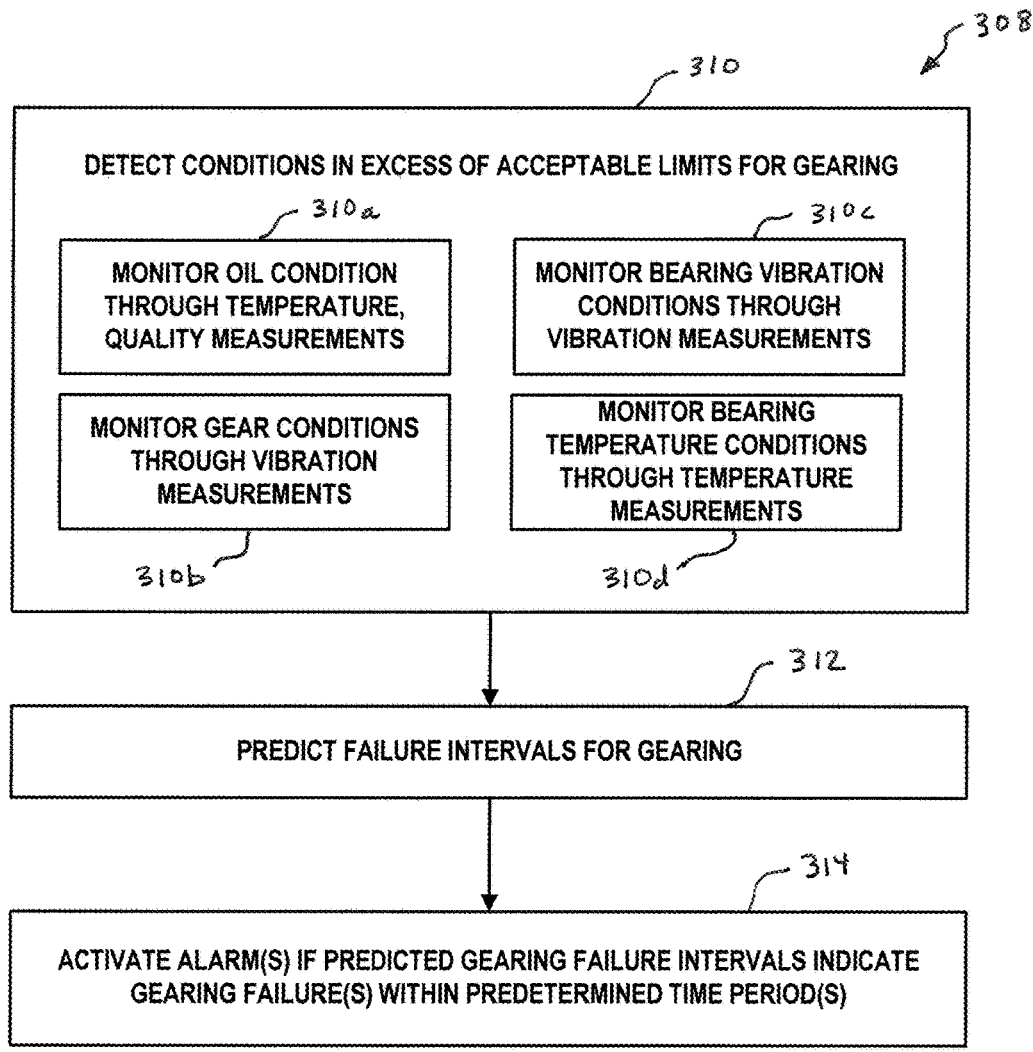
FIG. 23 is a flow chart illustration of a method of monitoring gearing in a pump, according to an exemplary embodiment.

In an exemplary embodiment, as illustrated in FIG. 23 with continuing reference to FIGS. 1-22, a method of monitoring gearing (e.g., gearbox, bull gears, pinion, etc.) in the reciprocating pump assembly 52 of the pump system 16 is generally referred to by the reference numeral 308. The method 308 includes: at step 310 detecting conditions in excess of acceptable limits for the gearing; at step 312 predicting failure interval(s) for the gearing; and at step 314 activating alarm(s) if gearing failure interval(s) indicate gearing failure(s) within predetermined time periods(s).

In an exemplary embodiment, as shown in FIG. 23, the step 310 includes a step 310*a*, at which oil or lubricant condition is monitored through temperature and/or quality measurements. At the step 310*a*, in an exemplary embodiment, the lubricant condition is monitored using the measurements taken by the sensors 92, 190, and 192. At step 310*b*, gear conditions are monitored through vibration measurements taken by, for example, the accelerometer 184. In several exemplary embodiments, at the step 310*b*, gear vibration conditions are monitored through vibration measurements taken by the accelerometers 184 and 200. At step 310*c*, bearing vibration conditions are monitored through vibration measurements taken by, for example, the accelerometer 184. In several exemplary embodiments, at the step 310*c*, bearing vibration conditions are monitored through vibration measurements taken by the accelerometers 184 and 200. At step 310*d*, bearing temperatures are monitored. In an exemplary embodiment, the step 310*d* includes the step 212 of the method 208. In an exemplary embodiment, the step 310*d* includes the step 214 of the method 208. In an exemplary embodiment, the step 310*d* includes the steps 212 and 214 of the method 208. In several exemplary embodiments, at the step 310, the conditions in excess of acceptable limits for gearing include unacceptable lubricant conditions (temperature, viscosity, contamination, water content, etc.), unacceptable bearing vibration conditions, unacceptable bearing temperature conditions, unacceptable gearing vibration conditions, or any combination thereof.

In an exemplary embodiment, at the step 310*b*, the vibration data from the reciprocating pump assembly 52 is correlated with gearing vibrations using vibration numerical solutions, finite element dynamic analyses, vibration closed-form solutions, or any combination thereof. In several exemplary embodiments, at the step 310*b*, the vibration data is correlated with gearing vibrations using historical experimental and/or operational data. In several exemplary embodiments, at the step 310*b*, the vibration data is correlated with gearing vibrations using one or more of the gateway 56, the application server 36, and the remote user device 42 and/or 44.

In an exemplary embodiment, at the step 312, gearing failure intervals within the reciprocating pump assembly 52 of the pump system 16 are predicted based on the unacceptable conditions detected at the step 310, thereby determining when one or more gearing components within the reciprocating pump assembly 52 will need to be replaced or reconditioned. In several exemplary embodiments, at the step 312, gearing failure intervals are predicted using one or more of the gateway 56, the application server 36, and the remote user device 42 and/or 44.

Figure 24:
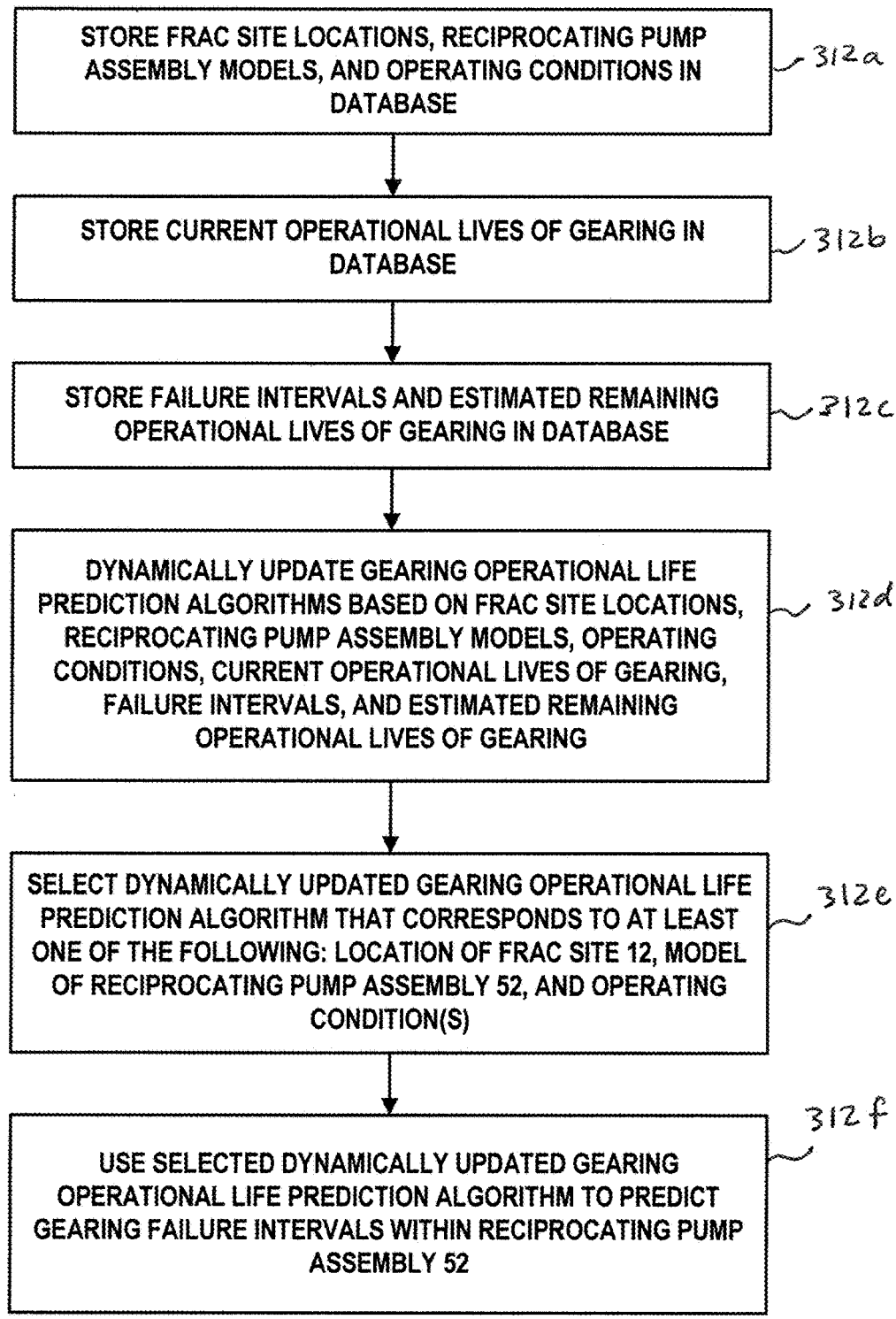
FIG. 24 is a flow chart illustration of a step of the method of FIG. 23, according to an exemplary embodiment.

In an exemplary embodiment, as illustrated in FIG. 24 with continuing reference to FIGS. 1-23, the step 312 includes at step 312a storing data sets in the database 41, with the data sets including data associated with respective frac site locations, reciprocating pump assembly models at the frac site locations, and operating conditions of the models at the frac site locations. In several exemplary embodiments, regarding the step 312a, the operating conditions with which the stored data sets are associated include bearing temperatures, bearing vibrations, the working pressures of the reciprocating pump assemblies, the applications for which the reciprocating pump assemblies are being used, the ambient temperatures surrounding the subject reciprocating pump assemblies, high pressure lubricant supply temperatures as measured by the respective temperature sensors 190 of different analysis systems each of which is substantially similar to the pump analysis system 24 of FIGS. 14A and 14B, low pressure lubricant supply temperatures as measured by the respective temperature sensors 192 of different analysis systems each of which is substantially similar to the pump analysis system 24 of FIGS. 14A and 14B, cylinder drain pan temperatures as measured by the respective sensors 194 of different analysis systems each of which is substantially similar to the pump analysis system 24 of FIGS. 14A and 14B, cylinder drain pan temperatures as measured by the respective sensors 196 of different analysis systems each of which is substantially similar to the pump analysis system 24 of FIGS. 14A and 14B, cylinder drain pan temperatures as measured by the respective sensors 198 of different analysis systems each of which is substantially similar to the pump analysis system 24 of FIGS. 14A and 14B, vibration data measured by the respective power end triaxial accelerometers 184 of different analysis systems each of which is substantially similar to the pump analysis system 24 of FIGS. 14A and 14B, vibration data measured by the respective fluid end triaxial accelerometers 200 of different analysis systems each of which is substantially similar to the pump analysis system 24 of FIGS. 14A and 14B, etc., or any combination thereof. At step 218b, stored in the database 41 are data sets associated with the current operational lives of bearings of the respective reciprocating pump assemblies 52 of different pump systems each of which is substantially similar to the pump system 16 of FIGS. 14A and 14B. At step 218c, stored in the database 41 are data sets associated with failure intervals and estimated remaining operational lives of bearings of the respective reciprocating pump assemblies 52 of different pump systems each of which is substantially similar to the pump system 16 of FIGS. 14A and 14B, etc., or any combination thereof. At step 312b, data sets associated with the current operational lives of gearing are stored in the database 41. At step 312c, data sets associated with failure intervals and estimated remaining operational lives of gearing are stored in the database 41.

In several exemplary embodiments, the data sets stored at the steps 312a, 312b, and 312c are associated with respective ones of the reciprocating pump assemblies 52 located at frac sites throughout the world, throughout a continent such as North America, throughout a region such as the American States under which the Marcellus Shale Formation is found, throughout a state such as Texas, or any combination thereof. In several exemplary embodiments, instead of, or in addition to the reciprocating pump assembly 52 of the pump system 16, the data sets stored at the steps 312a, 312b, and 312c are associated with reciprocating pump assemblies other than the reciprocating pump assembly 52 of the pump system 16. In several exemplary embodiments, the data sets stored at the steps 312a, 312b, and 312c are associated with one or more of the respective reciprocating pump assemblies 52 of the hydraulic fracturing pump systems 18, 20, and 22.

In several exemplary embodiments, instead of, or in addition to the database 41, the data sets stored at the steps 312a-312c are stored in another portion of the computer readable medium 40, the remote user device 42, the remote user device 44, the computer readable medium 60, another computer readable medium, or a combination thereof.

At step 312d, gearing operational life prediction algorithms are dynamically updated based on the data sets stored at the steps 312a, 312b, and 312c. At step 312e, at least one of the dynamically updated gearing operational life prediction algorithms is selected, the selected algorithm corresponding to at least one of the following parameters associated with the reciprocating pump assembly 52 of the pump 16: the location of the frac site 12 (or the frac site 12 itself); the particular model of the reciprocating pump assembly 52; and the operating conditions of the reciprocating pump assembly 52 (bearing temperatures within the reciprocating pump assembly 52, bearing vibrations within the reciprocating pump assembly 52, gearing vibrations within the reciprocating pump assembly 52, the working pressure of the reciprocating pump assembly 52, the application for which the reciprocating pump assembly 52 is being used, the ambient temperature surrounding the reciprocating pump assembly 52, high pressure lubricant supply temperature, low pressure lubricant supply temperature, power end vibration, cylinder drain pan temperature, etc.). For example, the dynamically updated algorithm selected at the step 312d is applicable to a reciprocating pump assembly being located at the frac site 12, a reciprocating pump assembly model that is the same as model of the reciprocating pump assembly 52 of the pump system 16, and having one or more operating conditions that match one or more of the operating conditions of the reciprocating pump assembly 52 of the pump 16.

At step 312f, the dynamically updated gearing operational life prediction algorithm selected at the step 312e is used to predict gearing failure interval(s) of the gearing within the reciprocating pump assembly 52 and thus the remaining operational live(s) of the gearing and/or components thereof.

In several exemplary embodiments, the step 312 enables dynamic algorithm updates to the location where processing and data analysis are occurring, enabling machine learning; for example, the repeated execution of the step 312 with different reciprocating pump assemblies reveals that a certain equipment model is susceptible to a particular condition and subsequent executions of the step 312 are aware of that susceptibility and account for that susceptibility when predicting gearing failure intervals and remaining operational lives of gearing.

In several exemplary embodiments, the steps 312a, 312b, and 312c are not specific to any particular reciprocating pump assembly, whereas the steps 312d and 312e are specific to a particular reciprocating pump assembly, which in the case of the present description is the reciprocating pump assembly 52 of the pump system 16.

At the step 314, one or more alarms are activated if at the step 312d it is determined that remaining operational live(s)

of gearing within the reciprocating pump assembly 52 are less than or equal to a predetermined time period such as, for example, 1 day, 6 hours, 1 hour, etc. In an exemplary embodiment, the step 314 includes graphically depicting an alarm on the remote user devices 42 and/or 44, the alarm indicating the existence of a potential gearing failure within the reciprocating pump assembly 52. As a result, the users of the remote user devices 42 and/or 44 are alerted to the existence of the potential gearing failure. In an exemplary embodiment, the step 314 includes graphically depicting an alarm on another output device that is in communication with the gateway 56 and/or the application server 36, such as a display screen in a control van located at the frac site 12. As a result, an operator in the control van is alerted to the gearing failure potential. In an exemplary embodiment, the step 314 includes the gateway 56, the application server 36, the remote user device 42, or the remote user device 44 sending one or more email messages, one or more text messages, one or more other messages, or any combination thereof; the one or messages indicate the potential gearing failure and the location thereof. In an exemplary embodiment, the step 314 includes the gateway 56, the application server 36, the remote user device 42, or the remote user device 44 flagging the potential gearing failure for immediate notification, and/or flagging the potential gearing failure and storing the flagging for notification at a later time.

In several exemplary embodiments, the method 308 includes a step at which a report is generated summarizing wear indicators over the reporting period and estimated remaining operational lives of gearing within the reciprocating pump assembly 52. In several exemplary embodiments, the method 308 includes a step at which the wear indicators and estimated remaining operational lives of the gearing within the reciprocating pump assembly 52 are stored in a benchmark index in, for example, the database 41. In several exemplary embodiments, the method includes a step at which the performance of the gearing within the reciprocating pump assembly 52 is displayed on, for example, the remote user device 42 or 44, and, in several exemplary embodiments, performance data of the gearing are compared to performance data of other gearing for other reciprocating pump assemblies located at the frac site 12, and/or global averages, which performance data and global averages.

In several exemplary embodiments, each of the methods 68, 78, 112, 208, 244, 264, 280, and 308 may be executed using the hydraulic fracturing pump system 16 and the pump analysis system 24 illustrated in FIGS. 14A and 14B; each of the methods 68, 78, 112, 208, 244, 264, 280, and 308 may also be executed using one of the pump analysis systems 26, 28, and 30, which pump analysis system may be substantially identical to the exemplary embodiment of the pump analysis system 24 illustrated in FIGS. 14A and 14B, as well as using the corresponding one of the hydraulic fracturing pump systems 18, 20, and 22. In several exemplary embodiments, one or more of the methods 68, 78, 112, 208, 244, 264, 280, and 308 may be executed, in whole or in part, using the pump analysis system 24 and the hydraulic fracturing system 16 illustrated in FIG. 3. In several exemplary embodiments, one or more of the methods 68, 78, 112, 208, 244, 264, 280, and 308 may be executed, in whole or in part, using: the exemplary embodiments illustrated in at least FIG. 3; the exemplary embodiments illustrated in at least FIG. 6; the exemplary embodiments illustrated in at least FIG. 12; the exemplary embodiments illustrated in at least FIGS. 14A and 14B; or any combination thereof.

In several exemplary embodiments, each of the methods 68, 78, 112, 208, 244, 264, 280, and 308 is executed in whole or in part using one or more of the following: the system 10, the pump analysis system 24 according to the exemplary embodiment illustrated in FIG. 3, the pump analysis system 24 according to the exemplary embodiment illustrated in FIG. 6, the pump analysis system 24 according to the exemplary embodiment illustrated in FIGS. 14A and 14B, the pump analysis system 26, the pump analysis system 28, the pump analysis system 30, and the remote central monitoring system 32. In several exemplary embodiments, during the operation of the system 10 or portion(s) thereof, one or more of the methods 68, 78, 112, 208, 244, 264, 280, and 308 are executed before, during, or after the execution of one or more other ones of the methods 68, 78, 112, 208, 244, 264, 280, and 308. In several exemplary embodiments, the gateway 56 is programmed to execute one or more of the methods 68, 78, 112, 208, 244, 264, 280, and 308. In several exemplary embodiments, the gateway 56 is programmed to execute one or more of the methods 68, 78, 112, 208, 244, 264, 280, and 308 before, during, or after the execution of one or more other ones of the methods 68, 78, 112, 208, 244, 264, 280, and 308. In several exemplary embodiments, the gateway 56, the application server 36, the remote user device 42, the remote user device 44, or any combination thereof, is programmed to execute one or more of the methods 68, 78, 112, 208, 244, 264, 280, and 308. In several exemplary embodiments, the gateway 56, the application server 36, the remote user device 42, the remote user device 44, or any combination thereof, is programmed to execute one or more of the methods 68, 78, 112, 208, 244, 264, 280, and 308 before, during, or after the execution of one or more other ones of the methods 68, 78, 112, 208, 244, 264, 280, and 308.

In several exemplary embodiments, a plurality of instructions, or computer program(s), are stored on a non-transitory computer readable medium, the instructions or computer program(s) being accessible to, and executable by, one or more processors. In several exemplary embodiments, the one or more processors execute the plurality of instructions (or computer program(s)) to operate in whole or in part the above-described exemplary embodiments. In several exemplary embodiments, the one or more processors are part of the communication server 34, the application server 36, the remote user device 42, the remote user device 44, the gateway 56, the controller 80, the controller 82, one or more other computing devices, or any combination thereof. In several exemplary embodiments, the non-transitory computer readable medium includes the non-transitory computer readable medium 40 and/or 60, and/or is part of the communication server 34, the application server 36, the remote user device 42, the remote user device 44, the gateway 56, the controller 80, the controller 82, one or more other computing devices, or any combination thereof.

In several exemplary embodiments, the system 10 includes a computer readable medium and a plurality of instructions stored thereon and executable by one or more processors, the plurality of instructions being specific to a pump such as, for example, the reciprocating pump assembly 52, the plurality of instructions comprising instructions to detect: pump operation (idle, running, speed, etc.); bearing overheating (temperatures exceeding warning/alarm thresholds); excessive bearing vibration (overall vibration exceeding warning/alarm thresholds, and/or energy at specific frequencies exceeding warning/alarm thresholds); cavitation detection (algorithmic calculation determining conditions in which cavitation occurs); lifetime counters (hours of operation of a pump and its components); wear rate monitoring/remaining useful life (RUL) (algorithmic calculations to identify wear rate and calculate RUL of main pump components such as, for example, the power end 176, the fluid end 178, gear box, etc.); wear rate monitoring/remaining useful life (RUL) (algorithmic calculations to identify wear rate and calculate RUL of pump expendable components such as, for example, valves, valve seats, packing, etc.); pump runs (to record frac stages) (information on pump runs—e.g., start time, duration, run number); pump runs (to record stages) (maximum/minimum/average summaries of certain tags such as, for example, max rod load, average speed, etc.); health and performance measurement including parameters that affect overall health and performance of the system; and seals leaking.

In several exemplary embodiments, the system 10 includes a computer readable medium and a plurality of instructions stored thereon and executable by one or more processors, the plurality of instructions being common to the pumps in the system 10, the plurality of instructions including the following features/functions: providing web interface with remote login capability; capturing events and sending them to Enterprise; integrating into customer supervisory and controls systems, e.g., a data van; providing configuration tool, fixes, and enhancements; providing raw value of each analog input and other diagnostic functions; providing graphic rework; recording pump sensor and calculation tag locally on the gateway and uploading to Enterprise; recording high frequency values of pump sensors locally for limited period of time; providing device to device communication; providing manual and over-the-air direct data interface; providing on-demand communication capable of identifying pump position/location (GPS); providing J1939 communication capabilities on a frac truck; recording the internal temperature of the gateway; and providing general software diagnostic functions, e.g., authorization and data forwarding stats, error log, etc.

In several exemplary embodiments, the above-described exemplary embodiments of the system 10 and/or exemplary embodiments of one or more portions of the system 10, provide: a real-time system monitor to assist in alerting operators of pump malfunctions in a timely manner; accurate measurement of the charge pressure for each pump to assist in quickly identifying problems in the pump system(s); indicator(s) of abnormalities in pump operation such as, for example, discharge valve failures, suction valve failures, cavitation, high rod load, etc., each of which is difficult to detect visually; an event monitor that displays the current status on all of the pumps in a system and details any failures and their solutions; a minimization of the risk of costly damage to the pump; and an improvement in the longevity of the pump.

Figure 25:
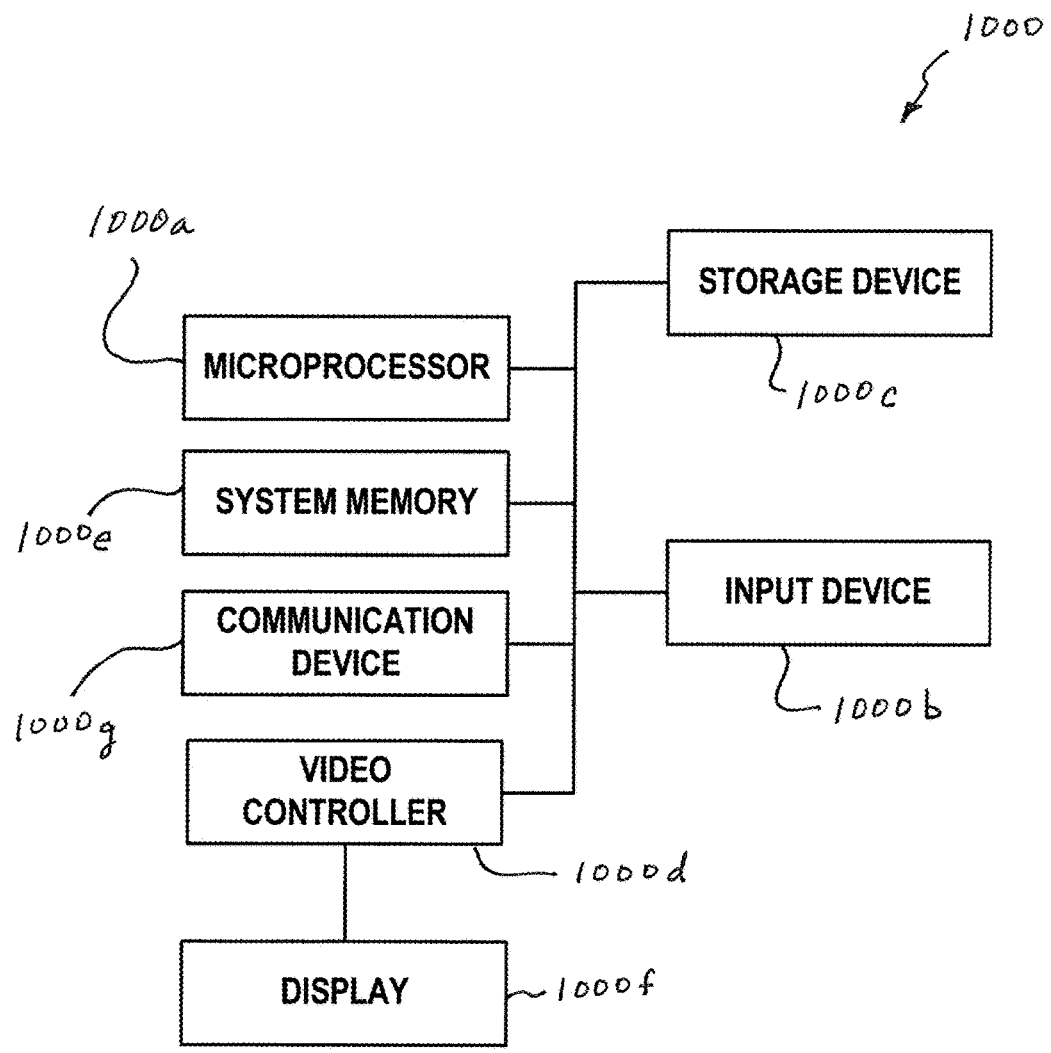
FIG. 25 is a diagrammatic illustration of a computing device for implementing one or more exemplary embodiments of the present disclosure, according to an exemplary embodiment.

In an exemplary embodiment, as illustrated in FIG. 25 with continuing reference to FIGS. 1-24, an illustrative computing device 1000 for implementing one or more embodiments of one or more of the above-described networks, elements, methods and/or steps, and/or any combination thereof, is depicted. The computing device 1000 includes a microprocessor 1000*a*, an input device 1000*b*, a storage device 1000*c*, a video controller 1000*d*, a system memory 1000*e*, a display 1000*f*, and a communication device 1000*g* all interconnected by one or more buses 1000*h*. In several exemplary embodiments, the storage device 1000*c* may include a floppy drive, hard drive, CD-ROM, optical drive, any other form of storage device and/or any combination thereof. In several exemplary embodiments, the storage device 1000*c* may include, and/or be capable of receiving, a floppy disk, CD-ROM, DVD-ROM, or any other form of computer-readable medium that may contain executable instructions. In several exemplary embodiments, the communication device 1000*g* may include a modem, network card, or any other device to enable the computing device to communicate with other computing devices. In several exemplary embodiments, any computing device represents a plurality of interconnected (whether by intranet or Internet) computer systems, including without limitation, personal computers, mainframes, PDAs, smartphones and cell phones.

In several exemplary embodiments, one or more of the components of the above-described exemplary embodiments include at least the computing device 1000 and/or components thereof, and/or one or more computing devices that are substantially similar to the computing device 1000 and/or components thereof. In several exemplary embodiments, one or more of the above-described components of the computing device 1000 include respective pluralities of same components.

In several exemplary embodiments, a computer system typically includes at least hardware capable of executing machine readable instructions, as well as the software for executing acts (typically machine-readable instructions) that produce a desired result. In several exemplary embodiments, a computer system may include hybrids of hardware and software, as well as computer sub-systems.

In several exemplary embodiments, hardware generally includes at least processor-capable platforms, such as client-machines (also known as personal computers or servers), and hand-held processing devices (such as smart phones, tablet computers, personal digital assistants (PDAs), or personal computing devices (PCDs), for example). In several exemplary embodiments, hardware may include any physical device that is capable of storing machine-readable instructions, such as memory or other data storage devices. In several exemplary embodiments, other forms of hardware include hardware sub-systems, including transfer devices such as modems, modem cards, ports, and port cards, for example.

In several exemplary embodiments, software includes any machine code stored in any memory medium, such as RAM or ROM, and machine code stored on other devices (such as floppy disks, flash memory, or a CD ROM, for example). In several exemplary embodiments, software may include source or object code. In several exemplary embodiments, software encompasses any set of instructions capable of being executed on a computing device such as, for example, on a client machine or server.

In several exemplary embodiments, combinations of software and hardware could also be used for providing enhanced functionality and performance for certain embodiments of the present disclosure. In an exemplary embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several exemplary embodiments, non-transitory computer readable mediums include, for example, passive data storage, such as a random access memory (RAM) as well as semi-permanent data storage such as a compact disk read only memory (CD-ROM). One or more exemplary embodiments of the present disclosure may be embodied in the RAM of a computer to transform a standard computer into a new specific computing machine. In several exemplary embodiments, data structures are defined organizations of data that may enable an embodiment of the present disclosure. In an exemplary embodiment, a data structure may provide an organization of data, or an organization of executable code.

In several exemplary embodiments, any networks and/or one or more portions thereof, may be designed to work on any specific architecture. In an exemplary embodiment, one or more portions of any networks may be executed on a single computer, local area networks, client-server networks, wide area networks, internets, hand-held and other portable and wireless devices and networks.

In several exemplary embodiments, a database may be any standard or proprietary database software. In several exemplary embodiments, the database may have fields, records, data, and other database elements that may be associated through database specific software. In several exemplary embodiments, data may be mapped. In several exemplary embodiments, mapping is the process of associating one data entry with another data entry. In an exemplary embodiment, the data contained in the location of a character file can be mapped to a field in a second table. In several exemplary embodiments, the physical location of the database is not limiting, and the database may be distributed. In an exemplary embodiment, the database may exist remotely from the server, and run on a separate platform. In an exemplary embodiment, the database may be accessible across the Internet. In several exemplary embodiments, more than one database may be implemented.

In several exemplary embodiments, a plurality of instructions stored on a non-transitory computer readable medium may be executed by one or more processors to cause the one or more processors to carry out or implement in whole or in part the above-described operation of each of the above-described exemplary embodiments, and/or any combination thereof. In several exemplary embodiments, such a processor may include one or more of the microprocessor 1000a, the one or more processors 38, the one or more processors 58, and/or any combination thereof, and such a non-transitory computer readable medium may include the computer readable medium 40, the computer readable medium 60, and/or may be distributed among one or more components of the system 10. In several exemplary embodiments, such a processor may execute the plurality of instructions in connection with a virtual computer system. In several exemplary embodiments, such a plurality of instructions may communicate directly with the one or more processors, and/or may interact with one or more operating systems, middleware, firmware, other applications, and/or any combination thereof, to cause the one or more processors to execute the instructions.

In several exemplary embodiments, one or more exemplary embodiments of the present disclosure are described and/or illustrated in whole or in part in U.S. application Ser. No. 13/866,121, filed Apr. 19, 2013, the entire disclosure of which is hereby incorporated herein by reference.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In several exemplary embodiments, the elements and teachings of the various illustrative exemplary embodiments may be combined in whole or in part in some or all of the illustrative exemplary embodiments. In addition, one or more of the elements, steps, and teachings of the various illustrative embodiments may be omitted, at least in part, and/or combined, at least in part, with one or more of the other elements and teachings of the various illustrative embodiments.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, invention(s) have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention(s). Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A monitoring apparatus adapted to monitor lubricant in a hydraulic fracturing pump system, the monitoring apparatus comprising:
   a gateway, comprising one or more processors and a non-transitory computer readable medium operably coupled thereto;
   one or more sensors configured to be in communication with the gateway;
      wherein the one or more sensors are configured to measure:
         a quality of the lubricant;
         a pressure of the lubricant; and
         a temperature of the lubricant;
      wherein the gateway is configured to receive, from the one or more sensors, sensor data associated with the quality of the lubricant, the pressure of the lubricant, and the temperature of the lubricant;
      wherein, to monitor the lubricant, the gateway is configured to: store the sensor data on the non-transitory computer readable medium; transmit to another computing device the sensor data and/or representative data based on the sensor data; visually indicate a status of the quality of the lubricant; visually indicate a status of the pressure of the lubricant; visually indicate a status of the temperature of the lubricant; or any combination thereof; and
      wherein the hydraulic fracturing pump system comprises:
         an engine,
         a transmission operably coupled to the engine, and
         a reciprocating pump assembly operably coupled to the transmission, the reciprocating pump assembly comprising a crankshaft via which the transmission is operably coupled to the reciprocating pump so that the engine is configured to rotate the crankshaft, via the transmission, to drive the reciprocating pump assembly;

a crankshaft rotation sensor configured to be in communication with the gateway; and an element configured to rotate along with the crankshaft and defining first and second outer-diameter transition regions;

wherein the crankshaft rotation sensor is configured to count a number of times the crankshaft rotates;

wherein the crankshaft rotation sensor comprises a proximity sensor, the proximity sensor comprising a distal end configured to be proximate the element when the element rotates along with the crankshaft;

wherein the first and second outer-diameter transition regions are circumferentially spaced; and wherein the proximity sensor is configured to detect each of the two outer-diameter transition regions as it rotates past the distal end of the proximity sensor.

2. The monitoring apparatus of claim 1, wherein the hydraulic fracturing pump system further comprises a lubricant source and a fluid line via which the reciprocating pump assembly is in fluid communication with the lubricant source; and wherein the quality, pressure, and temperature of the lubricant is the quality, pressure, and temperature, respectively, of the lubricant when the lubricant is in the fluid line.

3. The monitoring apparatus of claim 1, wherein the one or more sensors comprise:

a first sensor configured to measure the quality of the lubricant;

a second sensor configured to measure the pressure of the lubricant; and a third sensor configured to measure the temperature of the lubricant;

wherein each of the first, second, and third sensors is configured to be in communication with the gateway.

4. The monitoring apparatus of claim 3, wherein the apparatus further comprises a sensor connector, the sensor connector comprising:

a body, the body defining a longitudinally-extending flow passage through which the lubricant is configured to flow; and a plurality of radially-extending openings formed in the body;

wherein the first, second, and third sensors are configured to be connected to the body via respective ones of the radially-extending openings.

5. The monitoring apparatus of claim 1, wherein the element comprises a collar, the collar comprising first and second arcuate sections defining first and second outer diameters, respectively;

wherein the first and second diameters are different in that the first outer diameter is greater than the second outer diameter; and wherein the difference between the first and second outer diameters defines the first and second outer-diameter transition regions.

6. The monitoring apparatus of claim 1, wherein the first and second outer-diameter transition regions are circumferentially spaced by about 180 degrees.

7. The monitoring apparatus of claim 1, further comprising:

a GPS antenna configured to be operably coupled to the gateway; and one or more antennas configured to be operably coupled to the gateway;

wherein the gateway is configured to:
  interpret GPS location coordinates received via the GPS antenna; and
  send information identifying the location of the hydraulic fracturing pump system to another computing device via the one or more other antennas.

8. The monitoring apparatus of claim 7, wherein the one or more antennas comprise at least one of a cellular antenna and a satellite antenna.

9. The monitoring apparatus of claim 1, wherein the gateway is configured to visually indicate the status of the quality of the lubricant by activating one of a plurality of LED states.

10. A method of monitoring lubricant in a hydraulic fracturing pump system positioned at a location, the hydraulic fracturing pump system comprising an engine, a transmission operably coupled to the engine, and a reciprocating pump assembly operably coupled to the transmission, the reciprocating pump assembly comprising a crankshaft via which the transmission is operably coupled to the reciprocating pump so that the engine is configured to rotate the crankshaft, via the transmission, to drive the reciprocating pump assembly, and an element configured to rotate along with the crankshaft, the element defining first and second outer-diameter transition regions spaced circumferentially, the method comprising:

detecting, using a gateway and a proximity sensor comprising a distal end proximate the element when the element rotates along with the crankshaft, the two outer-diameter transition regions as the element rotates past the distal end of the proximity sensor to determine a RPM of the crankshaft;

detecting, using the gateway and the RPM of the crankshaft, one or more events associated with the lubricant in the hydraulic fracturing pump system, wherein the detected one or more events comprise at least one of the following:
  a temperature of the lubricant has exceeded a first threshold;
  the temperature of the lubricant has not reached a second threshold;
  a pressure of the lubricant pressure has exceeded a third threshold;
  the pressure of the lubricant has not reached a fourth threshold; and
  the quality of the lubricant has changed; and activating, using the gateway and/or a computing device in communication therewith, one or more alarms to indicate the existence of the detected one or more events.

11. The method of claim 10, wherein detecting the one or more events comprises:

measuring, using one or more sensors operably coupled to the gateway, one or more physical properties associated with the reciprocating pump assembly;

sending sensor data associated with the one or more physical properties from the one or more sensors to the gateway; and comparing, using the gateway or a computing device in communication therewith, the sensor data or representative data based thereon with one or more thresholds.

12. The method of claim 10, further comprising identifying, using a GPS antenna operably coupled to the gateway, the location of the hydraulic fracturing pump system;
- wherein the one or more alarms also indicate the location of the detected one or more events; and
- wherein identifying the location of the hydraulic fracturing pump system comprises:
  - interpreting, using the gateway, GPS location coordinates received via the GPS antenna; and
  - sending information identifying the location of the hydraulic fracturing pump system to another computing device via one or more other antennas that are operably coupled to the gateway.

13. The method of claim 10, wherein the hydraulic fracturing pump system further comprises a lubricant source and a fluid line via which the reciprocating pump assembly is in fluid communication with the lubricant source; and
- wherein the quality, pressure, and temperature of the lubricant is the quality, pressure, and temperature, respectively, of the lubricant when the lubricant is in the fluid line.

14. The method of claim 13, wherein detecting the one or more events comprises:
- connecting a sensor connector to the fluid line so that the sensor connector is in fluid communication with the fluid line;
- connecting one or more sensors to the sensor connector, wherein the one or more sensors comprise at least one of the following: a pressure sensor, a temperature sensor, and an oil quality sensor;
- wherein the one or more sensors are in communication with the gateway.

15. The method of claim 10, wherein the detected one or more events comprise at least one of the following:
- the reciprocating pump assembly has become active;
- the reciprocating pump assembly has become inactive; and
- the operational life of the reciprocating pump assembly has reached or exceeded a fifth threshold.

16. The method of claim 10, wherein the element comprises a collar, the collar comprising first and second arcuate sections defining first and second outer diameters, respectively;
- wherein the first and second diameters are different in that the first outer diameter is greater than the second outer diameter; and
- wherein the difference between the first and second outer diameters defines the first and second outer-diameter transition regions.

17. The method of claim 10, wherein the first and second outer-diameter transition regions are circumferentially spaced by about 180 degrees.

18. A monitoring apparatus adapted to monitor a hydraulic fracturing pump system comprising an engine, a transmission operably coupled to the engine, and a reciprocating pump assembly operably coupled to the transmission, the reciprocating pump assembly comprising a crankshaft via which the transmission is operably coupled to the reciprocating pump so that the engine is configured to rotate the crankshaft, via the transmission, to drive the reciprocating pump assembly, the monitoring apparatus comprising:
- an element configured to rotate along with the crankshaft;
  - wherein the element defines first and second outer-diameter transition regions; and
  - wherein the first and second outer-diameter transition regions are circumferentially spaced by about 180 degrees; and
- a proximity sensor comprising a distal end configured to be proximate the element when the element rotates along with the crankshaft;
  - wherein the proximity sensor is configured to detect each of the two outer-diameter transition regions as it rotates past the distal end of the proximity sensor to count a number of times the crankshaft rotates.

19. The monitoring apparatus of claim 18, wherein the element comprises a collar, the collar comprising first and second arcuate sections defining first and second outer diameters, respectively;
- wherein the first and second diameters are different in that the first outer diameter is greater than the second outer diameter; and
- wherein the difference between the first and second outer diameters defines the first and second outer-diameter transition regions.

20. The monitoring apparatus of claim 18, further comprising the hydraulic fracturing pump system.

* * * * *